US009687466B2

(12) United States Patent
Bacha et al.

(10) Patent No.: US 9,687,466 B2
(45) Date of Patent: *Jun. 27, 2017

(54) USE OF DIANHYDROGALACTITOL AND ANALOGS AND DERIVATIVES THEREOF TO TREAT GLIOBLASTOMA MULTIFORME

(71) Applicant: DELMAR PHARMACEUTICALS, INC., Vancouver (CA)

(72) Inventors: Jeffrey A. Bacha, Vancouver (CA); Dennis Brown, Menlo Park, CA (US); Sandra Dunn, Vancouver (CA); Anne Steinø, Vancouver (CA)

(73) Assignee: DELMAR PHARMACEUTICALS, INC., Vancouver (CA)

( * ) Notice: Subject to any disclaimer, the term of this patent is extended or adjusted under 35 U.S.C. 154(b) by 12 days.

This patent is subject to a terminal disclaimer.

(21) Appl. No.: 14/245,738

(22) Filed: Apr. 4, 2014

(65) Prior Publication Data

US 2014/0221442 A1  Aug. 7, 2014

Related U.S. Application Data

(63) Continuation-in-part of application No. PCT/US2013/022505, filed on Jan. 22, 2013.

(60) Provisional application No. 61/589,029, filed on Jan. 20, 212.

(51) Int. Cl.
| | |
|---|---|
| A61K 31/045 | (2006.01) |
| A61K 31/336 | (2006.01) |
| C12Q 1/68 | (2006.01) |
| A61K 31/4188 | (2006.01) |
| A61K 45/06 | (2006.01) |
| A61K 47/48 | (2006.01) |
| A61K 31/495 | (2006.01) |
| A61K 31/047 | (2006.01) |
| A61N 5/10 | (2006.01) |

(52) U.S. Cl.
CPC .......... *A61K 31/336* (2013.01); *A61K 31/047* (2013.01); *A61K 31/4188* (2013.01); *A61K 31/495* (2013.01); *A61K 45/06* (2013.01); *A61K 47/482* (2013.01); *A61K 47/48038* (2013.01); *A61K 47/48238* (2013.01); *A61N 5/1007* (2013.01); *C12Q 1/6886* (2013.01); *A61N 5/10* (2013.01); *A61N 2005/1024* (2013.01); *A61N 2005/1098* (2013.01); *C12Q 2600/106* (2013.01); *C12Q 2600/154* (2013.01); *C12Q 2600/156* (2013.01); *C12Q 2600/158* (2013.01)

(58) Field of Classification Search
CPC ... A61K 31/045; A61K 31/047; A61K 31/165
USPC ........................................................ 514/724
See application file for complete search history.

(56) References Cited

U.S. PATENT DOCUMENTS

| | | | |
|---|---|---|---|
| 4,801,575 | A | 1/1989 | Pardridge |
| 5,035,878 | A | 7/1991 | Borch et al. |
| 5,294,430 | A | 3/1994 | Borch et al. |
| 5,789,000 | A | 8/1998 | Hausheer et al. |
| 6,287,792 | B1 | 9/2001 | Pardridge et al. |
| 6,372,250 | B1 | 4/2002 | Pardridge |
| 6,443,898 | B1 | 9/2002 | Unger et al. |
| 6,573,292 | B1 | 6/2003 | Nardella |
| 6,921,772 | B2 | 7/2005 | Nardella |
| 7,101,576 | B2 | 9/2006 | Hovey et al. |
| 7,314,886 | B2 | 1/2008 | Chao et al. |
| 7,318,931 | B2 | 1/2008 | Okumu et al. |
| 7,388,079 | B2 | 6/2008 | Pardridge et al. |
| 7,446,122 | B2 | 11/2008 | Chao et al. |
| 7,619,005 | B2 | 11/2009 | Epstein et al. |
| 7,728,042 | B2 | 6/2010 | Eros et al. |
| 7,825,129 | B2 | 11/2010 | Pellicciari et al. |
| 7,879,896 | B2 | 2/2011 | Allegretti et al. |
| 7,928,105 | B2 | 4/2011 | Gangloff et al. |
| 7,956,064 | B2 | 6/2011 | Chua et al. |
| 8,008,491 | B2 | 8/2011 | Jiang et al. |
| 8,012,976 | B2 | 9/2011 | Wang et al. |
| 8,058,275 | B2 | 11/2011 | Xu et al. |
| 8,088,760 | B2 | 1/2012 | Chu et al. |
| 8,119,654 | B2 | 2/2012 | Jagtap et al. |
| 8,124,095 | B2 | 2/2012 | Pardridge et al. |
| 8,183,250 | B2 | 5/2012 | Penning et al. |
| 8,188,103 | B2 | 5/2012 | Van Der Aa et al. |
| 8,217,070 | B2 | 7/2012 | Zhu et al. |

(Continued)

FOREIGN PATENT DOCUMENTS

| | | |
|---|---|---|
| EP | 1332755 A1 | 8/2003 |
| EP | 1462119 A1 | 9/2004 |

(Continued)

OTHER PUBLICATIONS

Zhou et al., "Research Progress in New Anti-Cancer Drugs with Hexitols," Chin. J. Cancer 12: 257-260 (1993), 10 pages.

(Continued)

*Primary Examiner* — Kevin E Weddington
(74) *Attorney, Agent, or Firm* — Ditthavong & Steiner, P.C.

(57) ABSTRACT

The use of dianhydrogalactitol provides a novel therapeutic modality for the treatment of glioblastoma multiforme. Dianhydrogalactitol acts as an alkylating agent on DNA that creates $N^7$ methylation. Dianhydrogalactitol is effective in suppressing the growth of cancer stem cells and is active against tumors that are refractory to temozolomide; the drug acts independently of the MGMT repair mechanism.

42 Claims, 12 Drawing Sheets

(56) References Cited

U.S. PATENT DOCUMENTS

| | | |
|---|---|---|
| 8,247,416 B2 | 8/2012 | Menear et al. |
| 8,268,827 B2 | 9/2012 | Branca et al. |
| 8,277,807 B2 | 10/2012 | Gallagher et al. |
| 8,299,088 B2 | 10/2012 | Matteucci et al. |
| 8,299,256 B2 | 10/2012 | Vialard et al. |
| 8,309,573 B2 | 11/2012 | Fujio et al. |
| 8,324,282 B2 | 12/2012 | Gerson et al. |
| 8,338,477 B2 | 12/2012 | Duncan et al. |
| 8,344,162 B2 | 1/2013 | Jung et al. |
| 2002/0037328 A1 | 3/2002 | Brown |
| 2004/0023290 A1 | 2/2004 | Griffin et al. |
| 2005/0085419 A1 | 4/2005 | Morrison et al. |
| 2005/0181385 A1 | 8/2005 | Linsley et al. |
| 2005/0245508 A1 | 11/2005 | Weller et al. |
| 2007/0207952 A1 | 9/2007 | Silva et al. |
| 2008/0176923 A1 | 7/2008 | Salama |
| 2008/0207657 A1 | 8/2008 | Black et al. |
| 2009/0149397 A1 | 6/2009 | Ossovskaya et al. |
| 2009/0318561 A1 | 12/2009 | Davis et al. |
| 2010/0068303 A1 | 3/2010 | Yu |
| 2010/0158931 A1 | 6/2010 | Weinschenk et al. |
| 2010/0167939 A1 | 7/2010 | Aldape et al. |
| 2010/0178368 A1 | 7/2010 | Kreuter |
| 2010/0221754 A1 | 9/2010 | Ford et al. |
| 2011/0092960 A1 | 4/2011 | Shachar et al. |
| 2011/0190311 A1 | 8/2011 | Ciomei et al. |

FOREIGN PATENT DOCUMENTS

| | | | |
|---|---|---|---|
| WO | WO 0191741 A2 * | 12/2001 | ............ A61K 31/70 |
| WO | 03/070823 A2 | 8/2003 | |
| WO | 2014081405 A2 | 5/2014 | |

OTHER PUBLICATIONS

B. Calabretta et al., "Altered Expression of G1-Specific Genes in Human Malignant Myeloid Cells," Proc. Natl. Acad. Sci. USA 83: 1495-1498 (1986).

J.G. Paez et al., "EGFR Mutations in Lung Cancer: Correlation with Clinical Response to Gefitinib," Science 304: 1497-1500 (2004).

S.B. Vuyyuri et al., "Evaluation of D-Methionine as a Novel Oral Radiation Protector for Prevention of Mucositis," Clin. Cancer Res. 14: 2161-2170 (2008).

C. Aghajanian et al., "A Phase I Trial of the Novel Proteasome Inhibitor PS341 in Advanced Solid Tumor Malignancies," Clin. Cancer Res. 8: 2505-2511 (2002).

A.M. Martelli et al., "Phosphoinositide Signaling in Nuclei of Friend Cells: Phospholipase C [BETA] Downregulation Is Related to Cell Differentiation," Cancer Res. 54: 2536-2540 (1994).

T. Hideshima et al., "The Proteasome Inhibitor PS-341 Inhibits Growth, Induces Apoptosis, and Overcomes Drug Resistance in Human Multiple Myeloma Cells," Cancer Res. 61: 3071-3076 (2001).

C.A. Learn et al., "Resistance to Tyrosine Kinase Inhibition by Mutant Epidermal Growth Factor Variant III Contributes to the Neoplastic Phenotype of Glioblastoma Multiforme," Clin. Cancer Res. 10: 3216-3224 (2004).

M.E. Hegi et al., "Correlation of O6-Methylguanine Methyltransferase (MGMT) Promoter Methylation With Clinical Outcomes in Glioblastoma and Clinical Strategies to Modulate MGMT Activity," J. Clin. Oncol. 25: 4189-4199 (2008).

M. Gao et al., "Differential and Antagonistic Effects of v-Jun and c-Jun," Cancer Res. 56: 4229-4235 (1996).

A.L. Seynhaeve et al., "Tumor Necrosis Factor [ALPHA] Mediates Homogeneous Distribution of Liposomes in Murine Melanoma that Contributes to a Better Tumor Response," Cancer Res. 67: 9455-9462 (2007).

N. Osherov et al., "Selective Inhibition of the Epidermal Growth Factor and HER2/neu Receptors by Tyrphostins," J. Biol. Chem. 268: 11134-11142 (1993).

S. Kerpel-Fronius et al., Relation Between Dose, Plasma Concentration and Toxicity in a Phase I Trial Usuing High Dose Intermittent Administration of an Alkylating Agent, Diacetyldianhydrogalactitol (DADAG), Cancer Chemother. Pharmacol. 16: 264-268 (1986).

A.V. Lee et al., "New Mechanisms of Signal Transduction Inhibitor Action: Receptor Tyrosine Kinase Down-Regulation and Blockade of Signal Transactivation," Clin. Cancer Res. 9: 516s-523s (2003).

W.M. Pardridge, "The Blood-Brain Barrier: Bottleneck in Brain Drug Development," NeuroRx 2: 3-14 (2005).

S. Pejawar-Gaddy & O. J. Finn, "Cancer Vaccines: Accomplishments and Challenges," Crit. Rev. Oncol. Hematol. 67: 93-102 (2008).

Eagan et al., "Phase I Study of a Five-Day Intermittent Schedule for 1,2:5,6-Dianhydrogalactitol (NSC-132313)", Journal of the National Cancer Institute, Jan. 1976, vol. 56, No. 1, 4 Pages.

Levin et al., "Phase II Evaluation of Dibromodulcitol in the Treatment of Recurrent Medulloblastoma, Ependymoma, and Malignant Astrocytoma", Journal of Neurosurgery, Dec. 1984, vol. 61, 8 Pages.

Minniti et al., "Chemotherapy for Glioblastoma: Current Treatment and Future Perspectives for Cytotoxic and Targeted Agents", Anticancer Research, Dec. 2009, 16 Pages.

Tachibana et al., "Genetic Classifications in Glioblastomas: Biological and Clinical Significance of Genetic Alterations in Glioblastomas", Journal of Kanazawa Medical University, Dec. 2005, with English-language summary, 7 Pages.

Musaka et al., "IDG Genetic Mutation in Malignant Glioma", Japanese Journal of Cancer and Chemotherapy, Jun. 2011, vol. 38, No. 6, 10 Pages.

Nagane et al., "Latest Topics regarding the New Glioma Therapeutic Agent Temozolomide (TMZ, Temodar ®)", Medical Online, 2009, vol. 12, No. 1, 13 Pages.

* cited by examiner

Table 1. Summary of GBM models and their response to VAL083

* GBM stem cell line from patients

| | | | |
|---|---|---|---|
| SF188 | methylated | No | Yes |
| U251 | methylated | Yes (IC50=) | |
| T98G | unmethylated | No | Yes |
| U87 | methylated | Yes (IC50=) | |
| BT74* | unmethylated | No | Yes |
| GBM4* | | | |
| GBM8* | | | |
| L0* | ? | | |
| L1* | ? | | |
| L2* | ? | | |
| L3* | ? | | |

|        | TMZ resistance | MGMT status | MGMT |
|--------|---------------|-------------|------|
| SF188  | ++            | −           | Actin |
| U251   | +             | −           | MGMT / Actin |
| T98G   | +++           | +           | MGMT / Actin |

FIG. 3

USE OF DIANHYDROGALACTITOL AND ANALOGS AND DERIVATIVES THEREOF TO TREAT GLIOBLASTOMA MULTIFORME

CROSS-REFERENCES

This application is a continuation-in-part of PCT Patent Application Serial No. PCT/US2013/022505 by J. Bacha et al., filed on Jan. 22, 2013 and entitled "Use of Dianhydrogalactitol to Treat Glioblastoma Multiforme and Medulloblastoma," which in turn claimed the benefit of U.S. Provisional Application Ser. No. 61/589,029 by J. Bacha et al., filed on Jan. 20, 2012, and entitled "Use of Dianhydrogalactitol to Treat Glioblastoma Multiforme and Medulloblastoma," the contents of which are incorporated herein in their entirety by this reference.

FIELD OF THE INVENTION

This application is directed to the use of dianhydrogalactitol (DAG) and analogs and derivatives thereof to treat glioblastoma multiforme (GBM), as well as pharmaceutical compositions suitable for such use.

BACKGROUND OF THE INVENTION

Glioblastoma multiforme (GBM) is the most common and aggressive malignant primary brain tumor occurring in humans. GBM involves glial cells; it accounts for 52% of all functional tissue brain tumor cases and 20% of all intracranial tumors. Its estimated frequency of occurrence is 2-3 cases per 100,000 people in Europe and North America.

GBM has an extremely poor prognosis, despite various treatment methods including open craniotomy with surgical resection of as much of the tumor as possible, followed by sequential or concurrent chemoradiotherapy, antiangiogenic therapy with bevacizumab, gamma knife radiosurgery, and symptomatic management with corticosteroids. The median survival time for GBM is only 14 months.

Common symptoms of GBM include seizures, nausea, vomiting, headache, and hemiparesis. However, the single most prevalent symptom of GBM is progressive memory, personality, or neurological deficit due to involvement of the temporal or frontal lobe of the brain. The kind of symptoms produced by GBM depends highly on the location of the tumor and less on its exact pathology. The tumor can start producing symptoms quickly, but occasionally is asymptomatic until it reaches an extremely large size.

The etiology of GBM is largely unknown. For unknown reasons, GBM occurs more frequently in males. Most glioblastoma tumors appear to be sporadic, without any significant genetic predisposition. No links have been found between GBM, and several known carcinogenic risk factors, including diet, smoking, and exposure to electromagnetic fields. There have been some suggestions of a viral etiology, possibly SV40 or cytomegalovirus. There may also be some association between exposure to ionizing radiation and GBM. Additionally, it has been proposed that there is a link between polyvinyl chloride exposure and GBM; lead exposure in the workplace has also been suggested as a possible cause. There is an association of brain tumor incidence and malaria, suggesting that the anopheles mosquito, the carrier of malaria, might transmit a virus or other causative agent of GBM.

GBM is also relatively more common in people over 50 years of age, in Caucasians or Asians, and in patients that have already developed a low-grade astrocytoma which can develop into a higher grade tumor. Additionally, having one of the following genetic disorders is associated with an increased incidence of GBM: neurofibromatosis, tuberous sclerosis, Von Hippel-Lindau disease, Li-Fraumeni syndrome, or Turcot syndrome.

GBM tumors are typically characterized by the presence of small areas of necrotizing tissue that are surrounded by anaplastic cells. These characteristics, together with the presence of hyperplastic blood vessels, differentiate these malignancies from Grade 3 astrocytomas, which do not have these features.

There are four subtypes of glioblastoma. An extremely large fraction (97%) of tumors in the so-called "classical" subtype carry extra copies of the epidermal growth factor receptor (EGFR) gene and most of these tumors have higher than normal expression of EGFR, whereas the gene TP53, a tumor suppressor gene that has a number of anticancer activities, and which is often mutated in glioblastoma, is rarely mutated in this subtype. In contrast, the proneural subtype often has high rates of alteration in TP53 and in PDGFRA, the gene encoding the α-type platelet-derived growth factor receptor, as well as in IDH1, the gene encoding isocitrate dehydrogenase-1. The mesenchymal subtype is characterized by high rates of mutations or alterations in NF1, the gene encoding Neurofibromin type 1 and fewer alterations in the EGFR gene and less expression of EGFR than the other subtypes.

GBM usually forms in the cerebral white matter, grows quickly, and can become very large before producing symptoms. Less than 10% of GBMs form more slowly following degeneration of low-grade astrocytoma or anaplastic astrocytoma; such tumors are called secondary GBMs and are relatively more common in younger patients. The tumor may extend into the meninges or the ventricular wall leading to abnormally high protein content in the cerebrospinal fluid (CSF) (>100 mg/dL), as well as an occasional pleocytosis of 10 to 100 cells, mostly lymphocytes. Malignant cells present in the CSF can rarely spread to the spinal cord or cause meningeal gliomatosis; however, metastasis of GBM beyond the central nervous system is extremely unusual. About 50% of GBM tumors occupy more than one lobe of a hemisphere or are bilateral. Tumors of this type usually arise from the cerebrum and may rarely exhibit the classic infiltration across the corpus callosum, producing a bilateral ("butterfly") glioma. The tumor can take on a variety of appearances, depending on the amount of hemorrhage or necrosis present or the age of the tumor. A CT scan of a GBM tumor will usually show an inhomogeneous mass with a hypodense center and a variable ring of enhancement surrounded by edema. The mass effect from the tumor and the surrounding edema may compress the ventricles and cause hydrocephalus.

Cancer cells with stem-cell-like properties have been found in glioblastomas. This may be one cause of their resistance to conventional treatments and their high recurrence rate.

GBM often presents typical features on MRI, but these features are not specific for GBM and may be caused by other conditions. Specifically, when viewed with MRI, GBMs often appear as ring-enhancing lesions. However, other lesions such as abscesses, metastases of malignancies arising outside the central nervous system, tumefactive multiple sclerosis, or other conditions may have a similar appearance. The definitive diagnosis of a suspected GBM on CT or MRI requires a stereotactic biopsy or a craniotomy with tumor resection and pathologic confirmation. Because the grade of the tumor is based on the most malignant portion of the tumor, biopsy or subtotal tumor resection can result in undergrading of the tumor. Imaging of tumor blood flow using perfusion MRI and measuring tumor metabolite concentration with MR spectroscopy may add value to standard MRI, but pathology remains the gold standard for GBM diagnosis.

The treatment of GBM is extremely difficult due to several factors: (1) the tumor cells are very resistant to conventional therapies; (2) the brain is susceptible to damage using conventional therapy; (3) the brain has a very limited capacity for self-repair; and (4) many therapeutic drugs cannot cross the blood-brain barrier to act on the tumor. Symptomatic therapy, including the use of corticosteroids and anticonvulsant agents, focuses on relieving symptoms and improving the patient's neurologic function. However, such symptomatic therapy does nothing to slow the progression of the tumor, and, in the case of administration of phenytoin concurrently with radiation therapy, can result in substantial side effects including erythema multiforme and Steven-Johnson syndrome.

Palliative therapy usually is conducted to improve quality of life and to achieve a longer survival time. Palliative therapy can include surgery, radiation therapy, and chemotherapy. A maximally feasible resection with maximally tumor-free margins is generally performed along with external beam radiation and chemotherapy. Gross total resection of tumor is associated with better prognoses.

Surgery is the first stage of treatment of glioblastoma. An average GBM tumor contains $10^{11}$ cells, which is on average reduced to $10^9$ cells after surgery (a reduction of 99%). Surgery is used to take a section for a pathological diagnosis, to remove some of the symptoms of a large mass pressing against the brain, to remove disease before secondary resistance to radiotherapy and chemotherapy, and to prolong survival. The greater the extent of tumor removal, the better is the outcome. Removal of 98% or more of the tumor has been associated with a significantly longer and healthier survival time than if less than 98% of the tumor is removed. The chances of near-complete initial removal of the tumor can be greatly increased if the surgery is guided by a fluorescent dye known as 5-aminolevulinic acid. GBM cells are widely infiltrative through the brain at diagnosis, and so despite a "total resection" of all obvious tumor, most people with GBM later develop recurrent tumors either near the original site or at more distant "satellite lesions" within the brain. Other modalities, including radiation, are used after surgery in an effort to suppress and slow recurrent disease.

After surgery, radiotherapy is the mainstay of treatment for people with glioblastoma. A pivotal clinical trial carried out in the early 1970s showed that among 303 GBM patients randomized to radiation or nonradiation therapy, those who received radiation had a median survival more than double those who did not. Subsequent clinical research has attempted to build on the backbone of surgery followed by radiation. On average, radiotherapy after surgery can reduce the tumor size to $10^7$ cells. Whole brain radiotherapy does not improve the results when compared to the more precise and targeted three-dimensional conformal radiotherapy. A total radiation dose of 60-65 Gy has been found to be optimal for treatment.

The use of chemotherapy in GBM in addition to radiation has thus far only resulted in marginal improvements in survival as compared with radiation alone. In the treatment of other malignancies, the addition of chemotherapy to radiation has resulted in substantial improvements in survival, but this has not yet proven to be the case for GBM. One drug that does show results in connection with radiation is temozolomide (TMZ). TMZ plus radiation is now standard for most cases of GBM. TMZ seems to work by sensitizing the tumor cells to radiation.

However, TMZ is often ineffective due to drug resistance as the result of the catalytic activity of the enzyme $O^6$-methylguanine-DNA methyltransferase (MGMT), which results in repair of the lesion at $O^6$ of the guanine of DNA molecules. Chemoresistance to TMZ as a result of the activity of MGMT is frequently associated with poor outcomes in TMZ-treated patients, and patients in whom TMZ or bevacizumab is ineffective are left with few if any treatment options.

Additionally, cancer stem cells (CSC) are a subpopulation of the tumor that resist therapy and give rise to relapse.

Another therapeutic approach involves the use of the monoclonal antibody bevacizumab, which is a humanized monoclonal antibody that inhibits vascular endothelial growth factor A (VEGF-A) and thus acts as an angiogenesis inhibitor. Although bevacizumab may retard the progression of the disease, the first-line use of bevacizumab does not improve overall survival in patients with newly diagnosed GBM (M. R. Gilbert et al., "A Randomized Trial of Bevacizumab for Newly Diagnosed Glioblastoma," New Engl. J. Med. 370: 699-708 (2014), incorporated herein by this reference). Additionally, unlike some other malignancies in which the use of bevacizumab results in a potentiation of chemotherapy, in GBM, the addition of chemotherapy to bevacizumab did not improve on results from bevacizumab alone. Bevacizumab reduces brain edema and consequent symptoms, and it may be that the benefit from this drug is due to its action against edema rather than any action against the tumor itself. Some patients with brain edema do not actually have any active tumor remaining, but rather develop the edema as a late effect of prior radiation treatment. This type of edema is difficult to distinguish from that due to tumor, and both may coexist. Both respond to bevacizumab. However, patients in which both temozolomide and bevacizumab have been ineffective have few if any treatment options.

Another approach that has been proposed is gene transfer. Although gene transfer therapy has the potential to kill cancer cells while leaving healthy cells unharmed, this approach has been beset with many difficulties in other diseases, including the possibility for induction of other types of malignancies and interference with the functioning of the immune system.

Still other treatment modalities have been proposed for GBM, including the use of protein therapeutics, including the soluble CD95-Fc fusion protein APG101, immunotherapy with tumor vaccines, alternating electrical fields, and metabolic therapy. The value of these treatment modalities remains to be determined.

In GBM, the median survival time from the time of diagnosis without any treatment is 3 months, but with treatment survival of 1-2 years is common. Increasing age (>60 years of age) carries a worse prognostic risk. Death is usually due to cerebral edema or increased intracranial pressure.

A good initial Karnofsky Performance Score (KPS) and methylation of the promoter of the $O^6$-methylguanine-DNA methyltransferase (MGMT) gene are associated with longer survival. A DNA test can be carried out on glioblastomas to determine whether the promoter of the MGMT gene is methylated. Even in patients less than 50 years of age with a Karnofsky Performance Score (KPS) of equal to or greater than 90%, the 5-year survival rate is only 14%.

Therefore, there is a need for improved therapies for glioblastoma multiforme that provide improved survival with reduced side effects and impairment of function in surviving patients.

There is a particular need for therapeutic modalities that can cross the blood-brain barrier (BBB), that can suppress the growth and division of cancer stem cells (CSC), and that can avoid inactivation by $O^6$-methylguanine-DNA methyltransferase (MGMT). There is also a particular need for therapeutic modalities that yield increased response rates and improved quality of life for patients with these malignancies. There is also a particular need for therapeutic modalities that are effective in patients in which either or both of temozolomide and bevacizumab have proven ineffective.

SUMMARY OF THE INVENTION

The use of a substituted hexitol derivative to treat glioblastoma multiforme (GBM) provides an improved therapy for GBM that yields increased survival and is substantially free of side effects. In general, the substituted hexitols usable in methods and compositions according to the present invention include galactitols, substituted galacitols, dulcitols, and substituted dulcitols. Typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. A particularly preferred substituted hexitol derivative is dianhydrogalactitol (DAG). The substituted hexitol derivative can be employed together with other therapeutic modalities for these malignancies. Dianhydrogalactitol is particularly suited for the treatment of these malignancies because it crosses the blood-brain barrier, because it can suppress the growth of cancer stem cells (CSC), and because it is resistant to drug inactivation by $O^6$-methylguanine-DNA methyltransferase (MGMT). The substituted hexitol derivative yields increased response rates and improved quality of life for patients with GBM.

Dianhydrogalactitol is a novel alkylating agent that creates $N^7$-alkylation in DNA. Specifically, the principal mechanism of action is attributed to bi-functional $N^7$ DNA alkylation, via actual or derived epoxide groups, which cross-links across DNA strands at the $N^7$ position of guanine residues in DNA.

Accordingly, one aspect of the present invention is a method to improve the efficacy and/or reduce the side effects of the administration of a substituted hexitol derivative for treatment of GBM comprising the steps of:

(1) identifying at least one factor or parameter associated with the efficacy and/or occurrence of side effects of the administration of the substituted hexitol derivative for treatment of GBM; and (2) modifying the factor or parameter to improve the efficacy and/or reduce the side effects of the administration of the substituted hexitol derivative for treatment of GBM.

Typically, the factor or parameter is selected from the group consisting of:

(1) dose modification;
(2) route of administration;
(3) schedule of administration;
(4) indications for use;
(5) selection of disease stage;
(6) other indications;
(7) patient selection;
(8) patient/disease phenotype;
(9) patient/disease genotype;
(10) pre/post-treatment preparation
(11) toxicity management;
(12) pharmacokinetic/pharmacodynamic monitoring;
(13) drug combinations;
(14) chemosensitization;
(15) chemopotentiation;
(16) post-treatment patient management;
(17) alternative medicine/therapeutic support;
(18) bulk drug product improvements;
(19) diluent systems;
(20) solvent systems;
(21) excipients;
(22) dosage forms;
(23) dosage kits and packaging;
(24) drug delivery systems;
(25) drug conjugate forms;
(26) compound analogs;
(27) prodrugs;
(28) multiple drug systems;
(29) biotherapeutic enhancement;
(30) biotherapeutic resistance modulation;
(31) radiation therapy enhancement;
(32) novel mechanisms of action;
(33) selective target cell population therapeutics;
(34) use with ionizing radiation;
(35) use with an agent that counteracts myelosuppression; and
(36) use with an agent that increases the ability of the substituted hexitol to pass through the blood-brain barrier.

As detailed above, typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the substituted hexitol derivative is dianhydrogalactitol.

Another aspect of the present invention is a composition to improve the efficacy and/or reduce the side effects of suboptimally administered drug therapy employing a substituted hexitol derivative for the treatment of GBM comprising an alternative selected from the group consisting of:

(i) a therapeutically effective quantity of a modified substituted hexitol derivative or a derivative, analog, or prodrug of a substituted hexitol derivative or a modified substituted hexitol derivative, wherein the modified substituted hexitol derivative or the derivative, analog or prodrug of the substituted hexitol derivative or modified substituted hexitol derivative possesses increased therapeutic efficacy or reduced side effects for treatment of GBM as compared with an unmodified substituted hexitol derivative;

(ii) a composition comprising:

(a) a therapeutically effective quantity of a substituted hexitol derivative, a modified substituted hexitol derivative, or a derivative, analog, or prodrug of a substituted hexitol derivative or a modified substituted hexitol derivative; and (b) at least one additional therapeutic agent, therapeutic agent subject to chemosensitization, therapeutic agent subject to chemopotentiation, diluent, excipient, solvent system, drug delivery system, agent to counteract myelosuppression, or agent that increases the ability of the substituted hexitol to pass through the blood-brain barrier, wherein the composition possesses increased therapeutic efficacy or reduced side effects for treatment of GBM as compared with an unmodified substituted hexitol derivative;

(iii) a therapeutically effective quantity of a substituted hexitol derivative, a modified substituted hexitol derivative or a derivative, analog, or prodrug of a substituted hexitol derivative or a modified substituted hexitol derivative that is incorporated into a dosage form, wherein the substituted hexitol derivative, the modified substituted hexitol derivative or the derivative, analog, or prodrug of a substituted hexitol derivative or a modified substituted hexitol derivative incorporated into the dosage form possesses increased therapeutic efficacy or reduced side effects for treatment of GBM as compared with an unmodified substituted hexitol derivative;

(iv) a therapeutically effective quantity of a substituted hexitol derivative, a modified substituted hexitol derivative or a derivative, analog, or prodrug of a substituted hexitol derivative or a modified substituted hexitol derivative that is incorporated into a dosage kit and packaging, wherein the substituted hexitol derivative, the modified substituted hexitol derivative or the derivative, analog, or prodrug of a substituted hexitol derivative or a modified substituted hexitol derivative incorporated into the dosage kit and packaging possesses increased therapeutic efficacy or reduced side effects for treatment of GBM as compared with an unmodified substituted hexitol derivative; and (v) a therapeutically effective quantity of a substituted hexitol derivative, a modified substituted hexitol derivative or a derivative, analog, or prodrug of a substituted hexitol derivative or a modified substituted hexitol derivative that is subjected to a bulk drug product improvement, wherein substituted hexitol derivative, a modified substituted hexitol derivative or a derivative, analog, or prodrug of a substituted hexitol derivative or a modified substituted hexitol derivative subjected to the bulk drug product improvement possesses increased therapeutic efficacy or reduced side effects for treatment of GBM as compared with an unmodified substituted hexitol derivative.

As detailed above, typically the unmodified substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the unmodified substituted hexitol derivative is dianhydrogalactitol.

Another aspect of the present invention is a method of treating glioblastoma multiforme comprising the step of administering a therapeutically effective quantity of a substituted hexitol derivative to a patient suffering from the malignancy. As detailed above, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the substituted hexitol derivative is dianhydrogalactitol.

Typically, when the substituted hexitol derivative is dianhydrogalactitol, the therapeutically effective quantity of dianhydrogalactitol is a dosage from about 1 mg/m$^2$ to about 40 mg/m$^2$. Preferably, the therapeutically effective quantity of dianhydrogalactitol is a dosage from about 5 mg/m$^2$ to about 25 mg/m$^2$. Other dosages are described below.

Typically, the substituted hexitol derivative, such as dianhydrogalactitol, is administered by a route selected from the group consisting of intravenous and oral. Other potential routes of administration are described below.

The method can further comprise the step of administering a therapeutically effective dose of ionizing radiation. The method can further comprise the step of administering a therapeutically effective quantity of temozolomide, bevacizumab, or a corticosteroid.

The method can further comprise the administration of a therapeutically effective quantity of a tyrosine kinase inhibitor as described below.

The method can further comprise the administration of a therapeutically effective quantity of an epidermal growth factor receptor (EGFR) inhibitor as described below. The EGFR inhibitor can affect either wild-type binding sites or mutated binding sites, including Variant III, as described below.

BRIEF DESCRIPTION OF THE DRAWINGS

The following invention will become better understood with reference to the specification, appended claims, and accompanying drawings, where:

FIG. 1 is a chart showing three GBM cell lines used and showing their degree of temozolomide (TMZ) resistance and the status of methylation of the promoter of the O-6-methylguanine-DNA methyltransferase (MGMT) gene.

In FIG. 2A, (♦) represents TMZ results and (■) represents DAG results.

In FIG. 2B, (♦) represents TMZ results and (■) represents DAG results.

In FIG. 2C, (♦) represents TMZ results and (■) represents DAG results.

FIG. 3 is a chart showing the three cell lines used in FIGS. 2A, 2B, and 2C, indicating TMZ resistance and MGMT status.

DETAILED DESCRIPTION OF THE INVENTION

Figure 2:
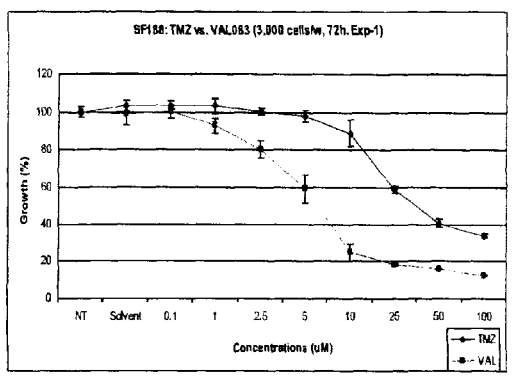
FIG. 2A is a graph showing the inhibition of growth of the GBM cell line SF188 with increasing concentrations of TMZ and dianhydrogalactitol (DAG) (shown as "VAL" in the figures) (two experiments each).
FIG. 2B is a graph showing the inhibition of growth of the GBM cell line U251 with increasing concentrations of TMZ and DAG (two experiments each).
FIG. 2C is a graph showing the inhibition of growth of the GBM cell line T98G with increasing concentrations of TMZ and DAG (two experiments each).
Figure 2:
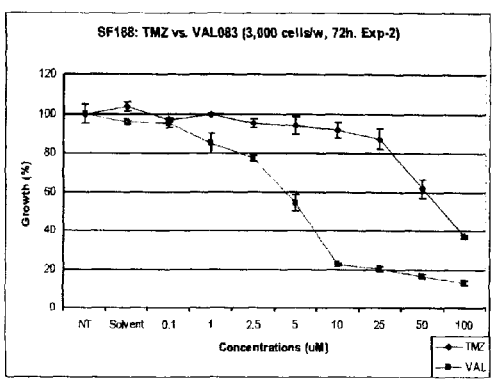
Figure 2:
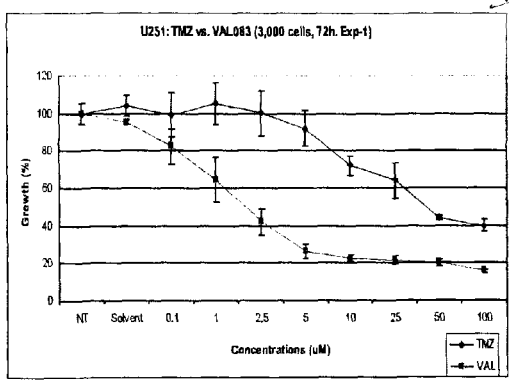
Figure 2:
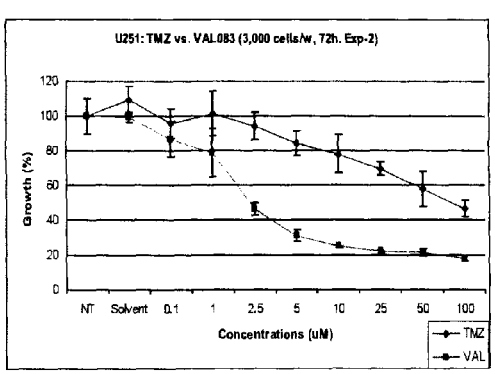
Figure 2:
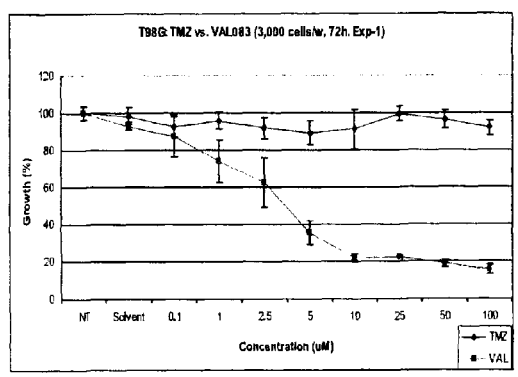
Figure 2:
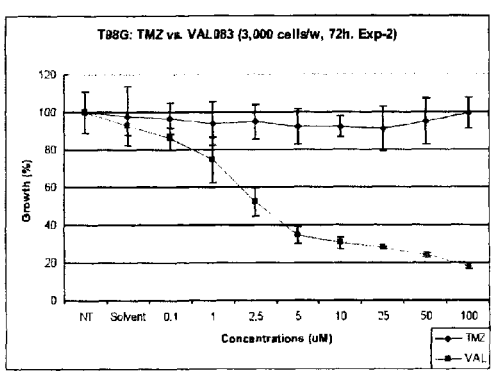

The compound dianhydrogalactitol (DAG) has been shown to have substantial efficacy in inhibiting the growth of glioblastoma multiforme (GBM) cells. In the case of GBM, DAG has proven to be more effective in suppressing the growth of GBM cells than temozolomide (TMZ), the current chemotherapy of choice for GBM. As detailed below, DAG can effectively cross the blood-brain barrier and can effectively suppress the growth of cancer stem cells (CSCs). DAG acts independently of the MGMT repair mechanism.

The structure of dianhydrogalactitol (DAG) is shown in Formula (I), below.

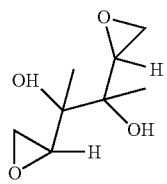

(I)

As detailed below, other substituted hexitols can be used in methods and compositions according to the present invention. In general, the substituted hexitols usable in methods and compositions according to the present invention include galactitols, substituted galacitols, dulcitols, and substituted dulcitols, including dianhydrogalactitol, diacetyldianhydrogalactitol, dibromodulcitol, and derivatives and analogs thereof. Typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the substituted hexitol derivative is dianhydrogalactitol.

These galactitols, substituted galacitols, dulcitols, and substituted dulcitols are either alkylating agents or prodrugs of alkylating agents, as discussed further below.

Also within the scope of the invention are derivatives of dianhydrogalactitol that, for example, have one or both hydrogens of the two hydroxyl groups of dianhydrogalactitol replaced with lower alkyl, have one or more of the hydrogens attached to the two epoxide rings replaced with lower alkyl, or have the methyl groups present in dianhydrogalactitol and that are attached to the same carbons that bear the hydroxyl groups replaced with $C_2$-$C_6$ lower alkyl or substituted with, for example, halo groups by replacing a hydrogen of the methyl group with, for example a halo group. As used herein, the term "halo group," without further limitation, refers to one of fluoro, chloro, bromo, or iodo. As used herein, the term "lower alkyl," without further limitation, refers to $C_1$-$C_6$ groups and includes methyl. The term "lower alkyl" can be further limited, such as "$C_2$-$C_6$ lower alkyl," which excludes methyl. The term "lower alkyl", unless further limited, refers to both straight-chain and branched alkyl groups. These groups can, optionally, be further substituted, as described below.

The structure of diacetyldianhydrogalactitol is shown in Formula (II), below.

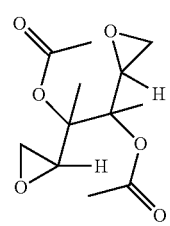

(II)

Also within the scope of the invention are derivatives of diacetyldianhydrogalactitol that, for example, have one or both of the methyl groups that are part of the acetyl moieties replaced with $C_2$-$C_6$ lower alkyl, have one or both of the hydrogens attached to the epoxide ring replaced with lower alkyl, or have the methyl groups attached to the same carbons that bear the acetyl groups replaced with lower alkyl or substituted with, for example, halo groups by replacing a hydrogen with, for example, a halo group.

The structure of dibromodulcitol is shown in Formula (III), below. Dibromodulcitol can be produced by the reaction of dulcitol with hydrobromic acid at elevated temperatures, followed by crystallization of the dibromodulcitol. Some of the properties of dibromodulcitol are described in N. E. Mischler et al., "Dibromoducitol," *Cancer Treat. Rev.* 6: 191-204 (1979), incorporated herein by this reference. In particular, dibromodulcitol, as an α,ω-dibrominated hexitol, dibromodulcitol shares many of the biochemical and biological properties of similar drugs such as dibromomannitol and mannitol myleran. Activation of dibromodulcitol to the diepoxide dianhydrogalactitol occurs in vivo, and dianhydrogalactitol may represent a major active form of the drug; this means that dibromogalactitol has many of the properties of a prodrug. Absorption of dibromodulcitol by the oral route is rapid and fairly complete. Dibromodulcitol has known activity in melanoma, breast lymphoma (both Hodgkins and non-Hodgkins), colorectal cancer, acute lymphoblastic leukemia and has been shown to lower the incidence of central nervous system leukemia, non-small cell lung cancer, cervical carcinoma, bladder carcinoma, and metastatic hemangiopericytoma.

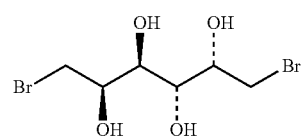

(III)

Also within the scope of the invention are derivatives of dibromodulcitol that, for example, have one or more hydrogens of the hydroxyl groups replaced with lower alkyl, or have one or both of the bromo groups replaced with another halo group such as chloro, fluoro, or iodo.

In general, for optional substituents at saturated carbon atoms such as those that are part of the structures of dianhydrogalactitol, derivatives of dianhydrogalactitol, diacetyldianhydrogalactitol, derivatives of diacetyldianhydrogalactitol, dibromodulcitol, and derivatives of dibromodulcitol, the following substituents can be employed: $C_6$-$C_{10}$ aryl, heteroaryl containing 1-4 heteroatoms selected from N, O, and S, $C_1$-$C_{10}$ alkyl, $C_1$-$C_{10}$ alkoxy, cycloalkyl, F, amino ($NR^1R^2$), nitro, —SR, —S(O)R, —S($O_2$)R, —S($O_2$)$NR^1R^2$, and —$CONR^1R^2$, which can in turn be optionally substituted. Further descriptions of potential optional substituents are provided below.

Optional substituents as described above that are within the scope of the present invention do not substantially affect the activity of the derivative or the stability of the derivative, particularly the stability of the derivative in aqueous solution. Definitions for a number of common groups that can be used as optional substituents are provided below; however, the omission of any group from these definitions cannot be taken to mean that such a group cannot be used as an optional substituent as long as the chemical and pharmacological requirements for an optional substituent are satisfied.

As used herein, the term "alkyl" refers to an unbranched, branched, or cyclic saturated hydrocarbyl residue, or a combination thereof, of from 1 to 12 carbon atoms that can be optionally substituted; the alkyl residues contain only C and H when unsubstituted. Typically, the unbranched or branched saturated hydrocarbyl residue is from 1 to 6 carbon atoms, which is referred to herein as "lower alkyl." When the alkyl residue is cyclic and includes a ring, it is understood that the hydrocarbyl residue includes at least three carbon atoms, which is the minimum number to form a ring. As used herein, the term "alkenyl" refers to an unbranched, branched or cyclic hydrocarbyl residue having one or more carbon-carbon double bonds. As used herein, the term "alkynyl" refers to an unbranched, branched, or cyclic hydrocarbyl residue having one or more carbon-carbon triple bonds; the residue can also include one or more double bonds. With respect to the use of "alkenyl" or "alkynyl," the presence of multiple double bonds cannot produce an aromatic ring. As used herein, the terms "hydroxyalkyl," "hydroxyalkenyl," and "hydroxyalkynyl," respectively, refer to an alkyl, alkenyl, or alkynyl group including one or more hydroxyl groups as substituents; as detailed below, further substituents can be optionally included. As used herein, the term "aryl" refers to a monocyclic or fused bicyclic moiety having the well-known characteristics of aromaticity; examples include phenyl and naphthyl, which can be optionally substituted. As used herein, the term "hydroxyaryl" refers to an aryl group including one or more hydroxyl groups as substituents; as further detailed below, further substituents can be optionally included. As used herein, the term "heteroaryl" refers to monocyclic or fused bicylic ring systems that have the characteristics of aromaticity and include one or more heteroatoms selected from O, S, and N. The inclusion of a heteroatom permits aromaticity in 5-membered rings as well as in 6-membered rings. Typical heteroaromatic systems include monocyclic $C_5$-$C_6$ heteroaromatic groups such as pyridyl, pyrimidyl, pyrazinyl, thienyl, furanyl, pyrrolyl, pyrazolyl, thiazolyl, oxazolyl, triazolyl, triazinyl, tetrazolyl, tetrazinyl, and imidazolyl, as well as the fused bicyclic moieties formed by fusing one of these monocyclic heteroaromatic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolylpyridyl, quinazolinyl, quinoxalinyl, cinnolinyl, and other ring systems known in the art. Any monocyclic or fused ring bicyclic system that has the characteristics of aromaticity in terms of delocalized electron distribution throughout the ring system is included in this definition. This definition also includes bicyclic groups where at least the ring that is directly attached to the remainder of the molecule has the characteristics of aromaticity, including the delocalized electron distribution that is characteristic of aromaticity. Typically the ring systems contain 5 to 12 ring member atoms and up to four heteroatoms, wherein the heteroatoms are selected from the group consisting of N, O, and S. Frequently, the monocyclic heteroaryls contain 5 to 6 ring members and up to three heteroatoms selected from the group consisting of N, O, and S; frequently, the bicyclic heteroaryls contain 8 to 10 ring members and up to four heteroatoms selected from the group consisting of N, O, and S. The number and placement of heteroatoms in heteroaryl ring structures is in accordance with the well-known limitations of aromaticity and stability, where stability requires the heteroaromatic group to be stable enough to be exposed to water at physiological temperatures without rapid degradation. As used herein, the term "hydroxheteroaryl" refers to a heteroaryl group including one or more hydroxyl groups as substituents; as further detailed below, further substituents can be optionally included. As used herein, the terms "haloaryl" and "haloheteroaryl" refer to aryl and heteroaryl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included. As used herein, the terms "haloalkyl," "haloalkenyl," and "haloalkynyl" refer to alkyl, alkenyl, and alkynyl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included.

As used herein, the term "optionally substituted" indicates that the particular group or groups referred to as optionally substituted may have no non-hydrogen substituents, or the group or groups may have one or more non-hydrogen substituents consistent with the chemistry and pharmacological activity of the resulting molecule. If not otherwise specified, the total number of such substituents that may be present is equal to the total number of hydrogen atoms present on the unsubstituted form of the group being described; fewer than the maximum number of such substituents may be present. Where an optional substituent is attached via a double bond, such as a carbonyl oxygen (C=O), the group takes up two available valences on the carbon atom to which the optional substituent is attached, so the total number of substituents that may be included is reduced according to the number of available valiences. As used herein, the term "substituted," whether used as part of "optionally substituted" or otherwise, when used to modify a specific group, moiety, or radical, means that one or more hydrogen atoms are, each, independently of each other, replaced with the same or different substituent or substituents.

Substituent groups useful for substituting saturated carbon atoms in the specified group, moiety, or radical include, but are not limited to, —$Z^a$, =O, —$OZ^b$, —$SZ^b$, =$S^-$, —$NZ^cZ^c$, =$NZ^b$, =N—$OZ^b$, trihalomethyl, —$CF_3$, —ON, —OCN, —SON, —NO, —$NO_2$, =$N_2$, —$N_3$, —S(O)$_2Z^b$, —S(O)$_2NZ^b$, —S($O_2$)$O^-$, —S($O_2$)$OZ^b$, —OS($O_2$)$OZ^b$, —OS($O_2$)$O^-$, —OS($O_2$)$OZ^b$, —P(O)($O^-$)$_2$, —P(O)($OZ^b$)($O^-$), —P(O)($OZ^b$)($OZ^b$), —C(O)$Z^b$, —C(S)$Z^b$, —C(N$Z^b$)$Z^b$, —C(O)$O^-$, —C(O)$OZ^b$, —C(S)$OZ^b$, —C(O)N$Z^cZ^c$, —C(N$Z^b$)N$Z^cZ^c$, —OC(O)$Z^b$, —OC(S)$Z^b$, —OC(O)$O^-$, —OC(O)$OZ^b$, —OC(S)$OZ^b$, —N$Z^b$C(O)$Z^b$, —N$Z^b$C(S)$Z^b$, —N$Z^b$C(O)$O^-$, —N$Z^b$C(O)$OZ^b$, —N$Z^b$C(S)$OZ^b$, —N$Z^b$C (O)NZ$^c$Z$^c$, —NZ$^b$C(NZ$^b$)Z$^b$, —NZ$^b$C(NZ$^b$)NZ$^c$Z$^c$, wherein Z$^a$ is selected from the group consisting of alkyl, cycloalkyl, heteroalkyl, cycloheteroalkyl, aryl, arylalkyl, heteroaryl and heteroarylalkyl; each Z$^b$ is independently hydrogen or Z$^a$; and each Z$^c$ is independently Z$^b$ or, alternatively, the two Z$^c$'s may be taken together with the nitrogen atom to which they are bonded to form a 4-, 5-, 6-, or 7-membered cycloheteroalkyl ring structure which may optionally include from 1 to 4 of the same or different heteroatoms selected from the group consisting of N, O, and S. As specific examples, —NZ$^c$Z$^c$ is meant to include —NH$_2$, —NH-alkyl, —N-pyrrolidinyl, and —N-morpholinyl, but is not limited to those specific alternatives and includes other alternatives known in the art. Similarly, as another specific example, a substituted alkyl is meant to include -alkylene-O-alkyl, -alkylene-heteroaryl, -alkylene-cycloheteroaryl, -alkylene-C(O)OZ$^b$, -alkylene-C(O)NZ$^b$Z$^b$, and —CH$_2$—CH$_2$—C(O)—CH$_{33}$ but is not limited to those specific alternatives and includes other alternatives known in the art. The one or more substituent groups, together with the atoms to which they are bonded, may form a cyclic ring, including, but not limited to, cycloalkyl and cycloheteroalkyl.

Similarly, substituent groups useful for substituting unsaturated carbon atoms in the specified group, moiety, or radical include, but are not limited to, —Z$^a$, halo, —O$^-$, —OZ$^b$, —SZ$^b$, —S$^-$, —NZ$^c$Z$^c$, trihalomethyl, —CF$_3$, —ON, —OCN, —SCN, —NO, —NO$_2$, —N$_3$, —S(O)$_2$Z$^b$, —S(O$_2$)O$^-$, —S(O$_2$)OZ$^b$, —OS(O$_2$)OZ$^b$, —OS(O$_2$)O$^-$, —P(O)(O$^-$)$_2$, —P(O)(OZ$^b$)(O$^-$), —P(O)(OZ$^b$)(OZ$^b$), —C(O)Z$^b$, —C(S)Z$^b$, —C(NZ$^b$)Z$^b$, —C(O)O$^-$, —C(O)OZ$^b$, —C(S)OZ$^b$, —C(O)NZ$^c$Z$^c$, —C(NZ$^b$)NZ$^c$Z$^c$, —OC(O)Z$^b$, —OC(S)Z$^b$, —OC(O)O$^-$, —OC(O)OZ$^b$, —OC(S)OZ$^b$, —NZ$^b$C(O)OZ$^b$, —NZ$^b$C(S)OZ$^b$, —NZ$^b$C(O)NZ$^c$Z$^c$, —NZ$^b$C(NZ$^b$)Z$^b$, and —NZ$^b$C(NZ$^b$)NZ$^c$Z$^c$, wherein Z$^a$, Z$^b$, and Z$^c$ are as defined above.

Similarly, substituent groups useful for substituting nitrogen atoms in heteroalkyl and cycloheteroalkyl groups include, but are not limited to, —Z$^a$, halo, —O$^-$, —OZ$^b$, —SZ$^b$, —S$^-$, —NZ$^c$Z$^c$, trihalomethyl, —CF$_3$, —CN, —OCN, —SCN, —NO, —NO$_2$, —S(O)$_2$Z$^b$, —S(O$_2$)O$^-$, —S(O$_2$)OZ$^b$, —OS(O$_2$)OZ$^b$, —OS(O$_2$)O$^-$, —P(O)(O$^-$)$_2$, —P(O)(OZ$^b$)(O$^-$), —P(O)(OZ$^b$)(OZ$^b$), —C(O)Z$^b$, —C(S)Z$^b$, —C(NZ$^b$)Z$^b$, —C(O)OZ$^b$, —C(S)OZ$^b$, —C(O)NZ$^c$Z$^c$, —C(NZ$^b$)NZ$^c$Z$^c$, —OC(O)Z$^b$, —OC(S)Z$^b$, —OC(O)OZ$^b$, —OC(S)OZ$^b$, —NZ$^b$C(O)Z$^b$, —NZ$^b$C(S)Z$^b$, —NZ$^b$C(O)OZ$^b$, —NZ$^b$C(S)OZ$^b$, —NZ$^b$C(O)NZ$^c$Z$^c$, —NZ$^b$C(NZ$^b$)Z$^b$, and —NZ$^b$C(NZ$^b$)NZ$^c$Z$^c$, wherein Z$^a$, Z$^b$, and Z$^c$ are as defined above.

The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and other alternatives for stereoisomers) as well as mixtures of stereoisomers in varying degrees of chiral purity or percentage of E and Z, including racemic mixtures, mixtures of diastereomers, and mixtures of E and Z isomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted isomer. When the chemical name does not specify the isomeric form of the compound, it denotes any one of the possible isomeric forms or mixtures of those isomeric forms of the compound.

The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein refers to isomers that change into one another with great ease so that they can exist together in equilibrium; the equilibrium may strongly favor one of the tautomers, depending on stability considerations. For example, ketone and enol are two tautomeric forms of one compound.

As used herein, the term "solvate" means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate." Examples of hydrate include, but are not limited to, hemihydrate, monohydrate, dihydrate, trihydrate, hexahydrate, and other water-containing species. It should be understood by one of ordinary skill in the art that the pharmaceutically acceptable salt, and/or prodrug of the present compound may also exist in a solvate form. The solvate is typically formed via hydration which is either part of the preparation of the present compound or through natural absorption of moisture by the anhydrous compound of the present invention.

As used herein, the term "ester" means any ester of a present compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The hydrolysable esters of the present compounds are the compounds whose carboxyls are present in the form of hydrolysable ester groups. That is, these esters are pharmaceutically acceptable and can be hydrolyzed to the corresponding carboxyl acid in vivo.

In addition to the substituents described above, alkyl, alkenyl and alkynyl groups can alternatively or in addition be substituted by $C_1$-$C_8$ acyl, $C_2$-$C_8$ heteroacyl, $C_6$-$C_{10}$ aryl, $C_3$-$C_8$ cycloalkyl, $C_3$-$C_8$ heterocyclyl, or $C_5$-$C_{10}$ heteroaryl, each of which can be optionally substituted. Also, in addition, when two groups capable of forming a ring having 5 to 8 ring members are present on the same or adjacent atoms, the two groups can optionally be taken together with the atom or atoms in the substituent groups to which they are attached to form such a ring.

"Heteroalkyl," "heteroalkenyl," and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form, respectively, a heteroalkyl, heteroalkenyl, or heteroalkynyl group. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker.

Similarly, "heterocyclyl" may be used to describe a non-aromatic cyclic group that contains at least one heteroatom (typically selected from N, O and S) as a ring member and that is connected to the molecule via a ring atom, which may be C (carbon-linked) or N (nitrogen-linked); and "heterocyclylalkyl" may be used to describe such a group that is connected to another molecule through a linker. The heterocyclyl can be fully saturated or partially saturated, but non-aromatic. The sizes and substituents that are suitable for the cycloalkyl, cycloalkylalkyl, heterocyclyl, and heterocyclylalkyl groups are the same as those described above for alkyl groups. The heterocyclyl groups typically contain 1, 2 or 3 heteroatoms, selected from N, O and S as ring members; and the N or S can be substituted with the groups commonly found on these atoms in heterocyclic systems. As used herein, these terms also include rings that contain a double bond or two, as long as the ring that is attached is not aromatic. The substituted cycloalkyl and heterocyclyl groups also include cycloalkyl or heterocyclic rings fused to an aromatic ring or heteroaromatic ring, provided the point of attachment of the group is to the cycloalkyl or heterocyclyl ring rather than to the aromatic/heteroaromatic ring.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S.

Acyl and heteroacyl groups are bonded to any group or molecule to which they are attached through the open valence of the carbonyl carbon atom. Typically, they are $C_1$-$C_8$ acyl groups, which include formyl, acetyl, pivaloyl, and benzoyl, and $C_2$-$C_8$ heteroacyl groups, which include methoxyacetyl, ethoxycarbonyl, and 4-pyridinoyl.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is $C_1$-$C_8$ alkyl. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a $C_1$-$C_4$ alkylene that is unsubstituted or is substituted with one or two $C_1$-$C_4$ alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a $C_5$-$C_6$ monocyclic heteroaryl group that is optionally substituted with the groups described above as substituents typical on aryl groups and a $C_1$-$C_4$ alkylene that is unsubstituted or is substituted with one or two $C_1$-$C_4$ alkyl groups or heteroalkyl groups, or it includes an optionally substituted phenyl ring or $C_5$-$C_6$ monocyclic heteroaryl and a $C_1$-$C_4$ heteroalkylene that is unsubstituted or is substituted with one or two $C_1$-$C_4$ alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain.

In general, any alkyl, alkenyl, alkynyl, acyl, or aryl or arylalkyl group that is contained in a substituent may itself optionally be substituted by additional substituents. The nature of these substituents is similar to those recited with regard to the primary substituents themselves if the substituents are not otherwise described.

"Amino" as used herein refers to —$NH_2$, but where an amino is described as "substituted" or "optionally substituted", the term includes NR'R" wherein each R' and R" is independently H, or is an alkyl, alkenyl, alkynyl, acyl, aryl, or arylalkyl group, and each of the alkyl, alkenyl, alkynyl, acyl, aryl, or arylalkyl groups is optionally substituted with the substituents described herein as suitable for the corresponding group; the R' and R" groups and the nitrogen atom to which they are attached can optionally form a 3- to 8-membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle," "carbocyclyl," or "carbocyclic" refers to a cyclic ring containing only carbon atoms in the ring, whereas the term "heterocycle" or "heterocyclic" refers to a ring comprising a heteroatom. The carbocyclyl can be fully saturated or partially saturated, but non-aromatic. For example, the carbocyclyl encompasses cycloalkyl. The carbocyclic and heterocyclic structures encompass compounds having monocyclic, bicyclic or multiple ring systems; and such systems may mix aromatic, heterocyclic, and carbocyclic rings. Mixed ring systems are described according to the ring that is attached to the rest of the compound being described.

As used herein, the term "heteroatom" refers to any atom that is not carbon or hydrogen, such as nitrogen, oxygen or sulfur. When it is part of the backbone or skeleton of a chain or ring, a heteroatom must be at least divalent, and will typically be selected from N, O, P, and S.

As used herein, the term "alkanoyl" refers to an alkyl group covalently linked to a carbonyl (C=O) group. The term "lower alkanoyl" refers to an alkanoyl group in which the alkyl portion of the alkanoyl group is $C_1$-$C_6$. The alkyl portion of the alkanoyl group can be optionally substituted as described above. The term "alkylcarbonyl" can alternatively be used. Similarly, the terms "alkenylcarbonyl" and "alkynylcarbonyl" refer to an alkenyl or alkynyl group, respectively, linked to a carbonyl group.

As used herein, the term "alkoxy" refers to an alkyl group covalently linked to an oxygen atom; the alkyl group can be considered as replacing the hydrogen atom of a hydroxyl group. The term "lower alkoxy" refers to an alkoxy group in which the alkyl portion of the alkoxy group is $C_1$-$C_6$. The alkyl portion of the alkoxy group can be optionally substituted as described above. As used herein, the term "haloalkoxy" refers to an alkoxy group in which the alkyl portion is substituted with one or more halo groups.

As used herein, the term "sulfo" refers to a sulfonic acid (—$SO_3H$) substituent.

As used herein, the term "sulfamoyl" refers to a substituent with the structure —$S(O_2)NH_2$, wherein the nitrogen of the $NH_2$ portion of the group can be optionally substituted as described above.

As used herein, the term "carboxyl" refers to a group of the structure —$C(O_2)H$.

As used herein, the term "carbamyl" refers to a group of the structure —$C(O_2)NH_2$, wherein the nitrogen of the $NH_2$ portion of the group can be optionally substituted as described above.

As used herein, the terms "monoalkylaminoalkyl" and "dialkylaminoalkyl" refer to groups of the structure -$Alk_1$-NH-$Alk_2$ and -$Alk_1$-N($Alk_2$)($Alk_3$), wherein $Alk_1$, $Alk_2$, and $Alk_3$ refer to alkyl groups as described above.

As used herein, the term "alkylsulfonyl" refers to a group of the structure —$S(O)_2$-Alk wherein Alk refers to an alkyl group as described above. The terms "alkenylsulfonyl" and "alkynylsulfonyl" refer analogously to sulfonyl groups covalently bound to alkenyl and alkynyl groups, respectively. The term "arylsulfonyl" refers to a group of the structure —$S(O)_2$—Ar wherein Ar refers to an aryl group as described above. The term "aryloxyalkylsulfonyl" refers to a group of the structure —$S(O)_2$-Alk-O—Ar, where Alk is an alkyl group as described above and Ar is an aryl group as described above. The term "arylalkylsulfonyl" refers to a group of the structure —$S(O)_2$-AlkAr, where Alk is an alkyl group as described above and Ar is an aryl group as described above.

As used herein, the term "alkyloxycarbonyl" refers to an ester substituent including an alkyl group wherein the carbonyl carbon is the point of attachment to the molecule. An example is ethoxycarbonyl, which is $CH_3CH_2OC(O)$—. Similarly, the terms "alkenyloxycarbonyl," "alkynyloxycarbonyl," and "cycloalkylcarbonyl" refer to similar ester substituents including an alkenyl group, alkenyl group, or cycloalkyl group respectively. Similarly, the term "aryloxycarbonyl" refers to an ester substituent including an aryl group wherein the carbonyl carbon is the point of attachment to the molecule. Similarly, the term "aryloxyalkylcarbonyl" refers to an ester substituent including an alkyl group wherein the alkyl group is itself substituted by an aryloxy group.

Other combinations of substituents are known in the art and, are described, for example, in U.S. Pat. No. 8,344,162 to Jung et al., incorporated herein by this reference. For example, the term "thiocarbonyl" and combinations of substituents including "thiocarbonyl" include a carbonyl group in which a double-bonded sulfur replaces the normal double-bonded oxygen in the group. The term "alkylidene" and similar terminology refer to an alkyl group, alkenyl group, alkynyl group, or cycloalkyl group, as specified, that has two hydrogen atoms removed from a single carbon atom so that the group is double-bonded to the remainder of the structure.

For the aspects described below relating to improvement in the therapeutic employment of a substituted hexitol derivative, typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol, unless otherwise specified. Preferably, the substituted hexitol derivative is dianhydrogalactitol, unless otherwise specified. In some cases, derivatives of dianhydrogalactitol such as compound analogs or prodrugs are preferred, as stated below.

One aspect of the present invention is an improvement in the therapeutic employment of a substituted hexitol derivative such as dianhydrogalactitol for treatment of GBM made by alterations to the time that the compound is administered, the use of dose-modifying agents that control the rate of metabolism of the compound, normal tissue protective agents, and other alterations. General examples include: variations of infusion schedules (e.g., bolus i.v. versus continuous infusion), the use of lymphokines (e.g., G-CSF, GM-CSF, EPO) to increase leukocyte count for improved immune response or for preventing anemia caused by myelosuppressive agents, or the use of rescue agents such as leucovorin for 5-FU or thiosulfate for cisplatin treatment. Specific inventive examples for a substituted hexitol derivative such as dianhydrogalactitol for treatment of GBM include: continuous i.v. infusion for hours to days; biweekly administration; doses greater than 5 mg/m$^2$/day; progressive escalation of dosing from 1 mg/m$^2$/day based on patient tolerance; doses less than 1 mg/m$^2$ for greater than 14 days; use of caffeine to modulate metabolism; use of isoniazid to modulate metabolism; single and multiple doses escalating from 5 mg/m$^2$/day via bolus; oral doses below 30 or above 130 mg/m$^2$; oral dosages up to 40 mg/m$^2$ for 3 days and then a nadir/recovery period of 18-21 days; dosing at a lower level for an extended period (e.g., 21 days); dosing at a higher level; dosing with a nadir/recovery period longer than 21 days; dosing at a level to achieve a concentration of the substituted hexitol derivative such as dianhydrogalactitol in the cerebrospinal fluid (CSF) of equal to or greater than 5 μM; dosing at a level to achieve a cytotoxic concentration in the CSF; the use of a substituted hexitol derivative such as dianhydrogalactitol as a single cytotoxic agent; administration on a 33-day cycle with a cumulative dose of about 9 mg/m$^2$; administration on a 33-day cycle with a cumulative dose of about 10 mg/m$^2$; administration on a 33-day cycle with a cumulative dose of about 20 mg/m$^2$; administration on a 33-day cycle with a cumulative dose of about 40 mg/m$^2$; administration on a 33-day cycle with a cumulative dose of about 80 mg/m$^2$; administration on a 33-day cycle with a cumulative dose of about 160 mg/m$^2$; administration on a 33-day cycle with a cumulative dose of about 240 mg/m$^2$; administration so that the plasma half-life is about 1-2 hours; administration so that the C$_{max}$ is <200 ng/ml; and administration so that the substituted hexitol derivative has a half life of >20 hours in the cerebrospinal fluid.

Another aspect of the invention is an improvement in the therapeutic employment of a substituted hexitol derivative such as dianhydrogalactitol for treatment of GBM made by alterations in the route by which the compound is administered. General examples include: changing route from oral to intravenous administration and vice versa; or the use of specialized routes such as subcutaneous, intramuscular, intraarterial, intraperitoneal, intralesional, intralymphatic, intratumoral, intrathecal, intravesicular, intracranial. Specific inventive examples for a substituted hexitol derivative such as dianhydrogalactitol for treatment of GBM include: topical administration; oral administration; slow-release oral delivery; intrathecal administration; intraarterial administration; continuous infusion; intermittent infusion; intravenous administration; administration through a longer infusion; administration through IV push; and administration to maximize the concentration of the substituted hexitol derivative in the CSF.

Yet another aspect of the invention is an improvement in the therapeutic employment of a substituted hexitol derivative such as dianhydrogalactitol made by changes in the schedule of administration. General examples include: daily administration, biweekly administration, or weekly administration. Specific inventive examples for a substituted hexitol derivative such as dianhydrogalactitol for treatment of GBM include: daily administration; weekly administration; weekly administration for three weeks; biweekly administration; biweekly administration for three weeks with a 1-2 week rest period; intermittent boost dose administration; daily administration for one week for multiple weeks; or administration on days 1, 2, and 3 of a 33-day cycle.

Yet another aspect of the invention is an improvement in the therapeutic employment of a substituted hexitol derivative such as dianhydrogalactitol for treatment of GBM made by alterations in the stage of disease at diagnosis/progression that the compound is administered. General examples include: the use of chemotherapy for non-resectable local disease, prophylactic use to prevent metastatic spread or inhibit disease progression or conversion to more malignant stages. Specific inventive examples for a substituted hexitol derivative such as dianhydrogalactitol for treatment of GBM include: use in an appropriate disease stage for GBM; use of the substituted hexitol derivative such as dianhydrogalactitol with angiogenesis inhibitors such as Avastin, a VEGF inhibitor, to prevent or limit metastatic spread, especially in the central nervous system; the use of a substituted hexitol derivative such as dianhydrogalactitol for newly diagnosed disease; the use of a substituted hexitol derivative such as dianhydrogalactitol for recurrent disease; the use of a substituted hexitol derivative such as dianhydrogalactitol for resistant or refractory disease; or the use of a substituted hexitol derivative such as dianhydrogalactitol for childhood glioblastoma.

Yet another aspect of the invention is an improvement in the therapeutic employment of a substituted hexitol derivative such as dianhydrogalactitol for treatment of GBM made by alterations to the type of patient that would best tolerate or benefit from the use of the compound. General examples include: use of pediatric doses for elderly patients, altered doses for obese patients; exploitation of co-morbid disease conditions such as diabetes, cirrhosis, or other conditions that may uniquely exploit a feature of the compound. Specific inventive examples for a substituted hexitol derivative such as dianhydrogalactitol for treatment of GBM include: patients with a disease condition characterized by a high level of a metabolic enzyme selected from the group consisting of histone deacetylase and ornithine decarboxylase; patients with a low or high susceptibility to a condition selected from the group consisting of thrombocytopenia and neutropenia; patients intolerant of GI toxicities; patients characterized by over- or under-expression of a gene selected from the group consisting of c-Jun, a GPCR, a signal transduction protein, VEGF, a prostate-specific gene, and a protein kinase; prostate-specific gene, and a protein kinase; patients characterized by carrying extra copies of the EGFR gene for GBM; patients characterized by mutations in at least one gene selected from the group consisting of TP53, PDGFRA, IDH1, and NF1 for GBM; patients characterized by methylation or lack of methylation of the promoter of the MGMT gene; patients characterized by the existence of an IDH1 mutation; patients characterized by the presence of IDH1 wild-type gene; patients characterized by the presence of 1p/19q co-deletion; patients characterized by a high expression of MGMT; patients characterized by a low expression of MGMT; or patients characterized by a mutation in EGFR including, but not limited to, EGFR Variant III.

Yet another aspect of the invention is an improvement in the therapeutic employment of a substituted hexitol derivative such as dianhydrogalactitol for treatment of GBM made by more precise identification of a patient's ability to tolerate, metabolize and exploit the use of the compound as associated with a particular phenotype of the patient. General examples include: use of diagnostic tools and kits to better characterize a patient's ability to process/metabolize a chemotherapeutic agent or the susceptibility of the patient to toxicity caused by potential specialized cellular, metabolic, or organ system phenotypes. Specific inventive examples for a substituted hexitol derivative such as dianhydrogalactitol for treatment of GBM include: use of a diagnostic tool, a diagnostic technique, a diagnostic kit, or a diagnostic assay to confirm a patient's particular phenotype; use of a method for measurement of a marker selected from the group consisting of histone deacetylase, ornithine decarboxylase, VEGF, a protein that is a gene product of jun, and a protein kinase; surrogate compound testing; or low dose pre-testing for enzymatic status.

Yet another aspect of the invention is an improvement in the therapeutic employment of a substituted hexitol derivative such as dianhydrogalactitol for treatment of GBM made by more precise identification of a patient's ability to tolerate, metabolize and exploit the use of the compound as associated with a particular genotype of the patient. General examples include: biopsy samples of tumors or normal tissues (e.g., glial cells or other cells of the central nervous system) that may also be taken and analyzed to specifically tailor or monitor the use of a particular drug against a gene target; studies of unique tumor gene expression patterns; or analysis of SNP's (single nucleotide polymorphisms), to enhance efficacy or to avoid particular drug-sensitive normal tissue toxicities. Specific inventive examples for a substituted hexitol derivative such as dianhydrogalactitol for treatment of GBM include: diagnostic tools, techniques, kits and assays to confirm a patient's particular genotype; gene/protein expression chips and analysis; Single Nucleotide Polymorphisms (SNP's) assessment; SNP's for histone deacetylase, ornithine decarboxylase, GPCR's, protein kinases, telomerase, or jun; identification and measurement of metabolism enzymes and metabolites; determination of mutation of PDGFRA gene; determination of mutation of IDH1 gene; determination of mutation of NF1 gene; determination of copy number of the EGFR gene; determination of status of methylation of promoter of MGMT gene; use for disease characterized by an IDH1 mutation; use for disease characterized by IDH1 wild-type; use for disease characterized by 1p/19q co-deletion; use for disease where the 1p/19q co-deletion is not present; use for disease characterized by an unmethylated promoter region of the MGMT gene; use for disease characterized by a methylated promoter region of the MGMT gene; use for disease characterized by high expression of MGMT; or use for disease characterized by low expression of MGMT.

Yet another aspect of the invention is an improvement in the therapeutic employment of a substituted hexitol derivative such as dianhydrogalactitol for treatment of GBM made by specialized preparation of a patient prior to or after the use of a chemotherapeutic agent. General examples include: induction or inhibition of metabolizing enzymes, specific protection of sensitive normal tissues or organ systems. Specific inventive examples for a substituted hexitol derivative such as dianhydrogalactitol for treatment of GBM include: the use of colchicine or analogs; use of diuretics such as probenecid; use of a uricosuric; use of uricase; non-oral use of nicotinamide; sustained release forms of nicotinamide; use of inhibitors of poly (ADP ribose) polymerase; use of caffeine; leucovorin rescue; infection control; antihypertensives.

Yet another aspect of the invention is an improvement in the therapeutic employment of a substituted hexitol derivative such as dianhydrogalactitol for treatment of GBM made by use of additional drugs or procedures to prevent or reduce potential side-effects or toxicities. General examples include: the use of anti-emetics, anti-nausea, hematological support agents to limit or prevent neutropenia, anemia, thrombocytopenia, vitamins, antidepressants, treatments for sexual dysfunction, and other supportive techniques. Specific inventive examples for a substituted hexitol derivative such as dianhydrogalactitol for treatment of GBM include: the use of colchicine or analogs; use of diuretics such as probenecid; use of a uricosuric; use of uricase; non-oral use of nicotinamide; use of sustained release forms of nicotinamide; use of inhibitors of poly ADP-ribose polymerase; use of caffeine; leucovorin rescue; use of sustained release allopurinol; non-oral use of allopurinol; use of bone marrow transplants; use of a blood cell stimulant; use of blood or platelet infusions; use of filgrastim, G-CSF, or GM-CSF; use of pain management techniques; use of anti-inflammatories; use of fluids; use of corticosteroids; use of insulin control medications; use of antipyretics; use of anti-nausea treatments; use of anti-diarrheal treatment; use of N-acetylcysteine; or use of antihistamines.

Yet another aspect of the invention is an improvement in the therapeutic employment of a substituted hexitol derivative such as dianhydrogalactitol for treatment of GBM made by the use of monitoring drug levels after dosing in an effort to maximize a patient's drug plasma level, to monitor the generation of toxic metabolites, monitoring of ancillary medicines that could be beneficial or harmful in terms of drug-drug interactions. General examples include: the monitoring of drug plasma protein binding, and monitoring of other pharmacokinetic or pharmacodynamic variables. Specific inventive examples for a substituted hexitol derivative such as dianhydrogalactitol for treatment of GBM include: multiple determinations of drug plasma levels; or multiple determinations of metabolites in the blood or urine.

Yet another aspect of the invention is an improvement in the therapeutic employment of a substituted hexitol derivative such as dianhydrogalactitol for treatment of GBM made by exploiting unique drug combinations that may provide a more than additive or synergistic improvement in efficacy or side-effect management. Specific inventive examples for a substituted hexitol derivative such as dianhydrogalactitol for treatment of GBM include: use with topoisomerase inhibitors; use with fraudulent nucleosides; use with fraudulent nucleotides; use with thymidylate synthetase inhibitors; use with signal transduction inhibitors; use with cisplatin or platinum analogs; use with alkylating agents such as the nitrosoureas (BCNU, Gliadel wafers, CCNU, nimustine (ACNU), bendamustine (Treanda)); use with alkylating agents that damage DNA at a different place than does DAG (TMZ, BCNU, CCNU, and other alkylating agents all damage DNA at $O^6$ of guanine, whereas DAG cross-links at $N^7$); use with a monofunctional alkylating agent; use with a bifunctional alkylating agent; use with anti-tubulin agents; use with antimetabolites; use with berberine; use with apigenin; use with amonafide; use with colchicine or analogs; use with genistein; use with etoposide; use with cytarabine; use with camptothecins; use with vinca alkaloids; use with topoisomerase inhibitors; use with 5-fluorouracil; use with curcumin; use with NF-κB inhibitors; use with rosmarinic acid; use with mitoguazone; use with tetrandrine; use with temozolomide (TMZ); use with biological therapies such as antibodies such as Avastin (a VEGF inhibitor), Rituxan, Herceptin, Erbitux; use with epidermal growth factor receptor (EGFR) inhibitors; use with tyrosine kinase inhibitors; use with poly (ADP-ribose) polymerase (PARP) inhibitors; or use with cancer vaccine therapy.

Yet another aspect of the invention is an improvement in the therapeutic employment of a substituted hexitol derivative such as dianhydrogalactitol for treatment of GBM made by exploiting the substituted hexitol derivative such as dianhydrogalactitol as a chemosensitizer where no measureable activity is observed when used alone but in combination with other therapeutics a more than additive or synergistic improvement in efficacy is observed. Specific inventive examples for a substituted hexitol derivative such as dianhydrogalactitol for treatment of GBM include: as a chemosensitizer in combination with topoisomerase inhibitors; as a chemosensitizer in combination with fraudulent nucleosides; as a chemosensitizer in combination with fraudulent nucleotides; as a chemosensitizer in combination with thymidylate synthetase inhibitors; as a chemosensitizer in combination with signal transduction inhibitors; as a chemosensitizer in combination with cisplatin or platinum analogs; as a chemosensitizer in combination with alkylating agents such as BCNU, BCNU wafers, Gliadel, CCNU, bendamustine (Treanda), or Temozolomide (Temodar); as a chemosensitizer in combination with anti-tubulin agents; as a chemosensitizer in combination with antimetabolites; as a chemosensitizer in combination with berberine; as a chemosensitizer in combination with apigenin; as a chemosensitizer in combination with amonafide; as a chemosensitizer in combination with colchicine or analogs; as a chemosensitizer in combination with genistein; as a chemosensitizer in combination with etoposide; as a chemosensitizer in combination with cytarabine; as a chemosensitizer in combination with camptothecins; as a chemosensitizer in combination with vinca alkaloids; as a chemosensitizer in combination with topoisomerase inhibitors; as a chemosensitizer in combination with 5-fluorouracil; as a chemosensitizer in combination with curcumin; as a chemosensitizer in combination with NF-κB inhibitors; as a chemosensitizer in combination with rosmarinic acid; as a chemosensitizer in combination with mitoguazone; as a chemosensitizer in combination with tetrandrine; as a chemosensitizer in combination with a tyrosine kinase inhibitor; as a chemosensitizer in combination with an EGFR inhibitor; or as a chemosensitizer in combination with an inhibitor of poly (ADP-ribose) polymerase (PARP).

Yet another aspect of the invention is an improvement in the therapeutic employment of a substituted hexitol derivative such as dianhydrogalactitol for treatment of GBM made by exploiting the substituted hexitol derivative such as dianhydrogalactitol as a chemopotentiator where minimal therapeutic activity is observed alone but in combination with other therapeutics a more than additive or synergistic improvement in efficacy is observed. Specific inventive examples for a substituted hexitol derivative such as dianhydrogalactitol for treatment of GBM include: as a chemopotentiator in combination with topoisomerase inhibitors; as a chemopotentiator in combination with fraudulent nucleosides; as a chemopotentiator in combination with thymidylate synthetase inhibitors; as a chemopotentiator in combination with signal transduction inhibitors; as a chemopotentiator in combination with cisplatin or platinum analogs; as a chemopotentiator in combination with use with alkylating agents such as BCNU, BCNU wafers, Gliadel, or bendamustine (Treanda); as a chemopotentiator in combination with anti-tubulin agents; as a chemopotentiator in combination with antimetabolites; as a chemopotentiator in combination with berberine; as a chemopotentiator in combination with apigenin; as a chemopotentiator in combination with amonafide; as a chemopotentiator in combination with colchicine or analogs; as a chemopotentiator in combination with genistein; as a chemopotentiator in combination with etoposide; as a chemopotentiator in combination with cytarabine; as a chemopotentiator in combination with camptothecins; as a chemopotentiator in combination with vinca alkaloids; as a chemopotentiator in combination with topoisomerase inhibitors; as a chemopotentiator in combination with 5-fluorouracil; as a chemopotentiator in combination with curcumin; as a chemopotentiator in combination with NF-κB inhibitors; as a chemopotentiator in combination with rosmarinic acid; as a chemopotentiator in combination with mitoguazone; as a chemopotentiator in combination with tetrandrine; as a chemopotentiator in combination with a tyrosine kinase inhibitor; as a chemopotentiator in combination with an EGFR inhibitor; or as a chemopotentiator in combination with an inhibitor of poly (ADP-ribose) polymerase (PARP).

Yet another aspect of the invention is an improvement in the therapeutic employment of a substituted hexitol derivative such as dianhydrogalactitol for treatment of GBM made by drugs, treatments and diagnostics to allow for the maximum benefit to patients treated with a compound. General examples include: pain management, nutritional support, anti-emetics, anti-nausea therapies, anti-anemia therapy, anti-inflammatories. Specific inventive examples for a substituted hexitol derivative such as dianhydrogalactitol for treatment of GBM include: use with therapies associated with pain management; nutritional support; anti-emetics; anti-nausea therapies; anti-anemia therapy; anti-inflammatories: antipyretics; immune stimulants.

Yet another aspect of the invention is an improvement in the therapeutic employment of a substituted hexitol derivative such as dianhydrogalactitol for treatment of GBM made by the use of complementary therapeutics or methods to enhance effectiveness or reduce side effects. Specific inventive examples for a substituted hexitol derivative such as dianhydrogalactitol for treatment of GBM include: hypnosis; acupuncture; meditation; herbal medications created either synthetically or through extraction including NF-κB inhibitors (such as parthenolide, curcumin, rosmarinic acid); natural anti-inflammatories (including rhein, parthenolide); immunostimulants (such as those found in *Echinacea*); antimicrobials (such as berberine); flavonoids, isoflavones, and flavones (such as apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin); applied kinesiology.

Yet another aspect of the invention is an improvement in the therapeutic employment of a substituted hexitol derivative such as dianhydrogalactitol for treatment of GBM made by alterations in the pharmaceutical bulk substance. General examples include: salt formation, homogeneous crystalline structure, pure isomers. Specific inventive examples for a substituted hexitol derivative such as dianhydrogalactitol for treatment of GBM include: salt formation; homogeneous crystalline structure; pure isomers; increased purity; lower residual solvents; or lower heavy metals.

Yet another aspect of the invention is an improvement in the therapeutic employment of a substituted hexitol derivative such as dianhydrogalactitol for treatment of GBM made by alterations in the diluents used to solubilize and deliver/present the compound for administration. General examples include: Cremophor-EL, cyclodextrins for poorly water soluble compounds. Specific inventive examples for a substituted hexitol derivative such as dianhydrogalactitol for treatment of GBM include: use of emulsions; dimethyl sulfoxide (DMSO); N-methylformamide (NMF); dimethylformamide (DMF); dimethylacetamide (DMA); ethanol; benzyl alcohol; dextrose containing water for injection; Cremophor; cyclodextrins; PEG.

Yet another aspect of the invention is an improvement in the therapeutic employment of a substituted hexitol derivative such as dianhydrogalactitol for treatment of GBM made by alterations in the solvents used or required to solubilize a compound for administration or for further dilution. General examples include: ethanol, dimethylacetamide (DMA). Specific inventive examples for a substituted hexitol derivative such as dianhydrogalactitol for treatment of GBM include: the use of emulsions; DMSO; NMF; DMF; DMA; ethanol; benzyl alcohol; dextrose containing water for injection; Cremophor; cyclodextrin; or PEG.

Yet another aspect of the invention is an improvement in the therapeutic employment of a substituted hexitol derivative such as dianhydrogalactitol for treatment of GBM made by alterations in the materials/excipients, buffering agents, or preservatives required to stabilize and present a chemical compound for proper administration. General examples include: mannitol, albumin, EDTA, sodium bisulfite, benzyl alcohol. Specific inventive examples for a substituted hexitol derivative such as dianhydrogalactitol for treatment of GBM include: the use of mannitol; albumin; EDTA; sodium bisulfite; benzyl alcohol; carbonate buffers; phosphate buffers.

Yet another aspect of the invention is an improvement in the therapeutic employment of a substituted hexitol derivative such as dianhydrogalactitol for treatment of GBM made by alterations in the potential dosage forms of the compound dependent on the route of administration, duration of effect, plasma levels required, exposure to side-effect normal tissues and metabolizing enzymes. General examples include: tablets, capsules, topical gels, creams, patches, suppositories. Specific inventive examples for a substituted hexitol derivative such as dianhydrogalactitol for treatment of GBM include: the use of tablets; capsules; topical gels; topical creams; patches; suppositories; lyophilized dosage fills.

Yet another aspect of the invention is an improvement in the therapeutic employment of a substituted hexitol derivative such as dianhydrogalactitol for treatment of GBM made by alterations in the dosage forms, container/closure systems, accuracy of mixing and dosage preparation and presentation. General examples include: amber vials to protect from light, stoppers with specialized coatings. Specific inventive examples for a substituted hexitol derivative such as dianhydrogalactitol for treatment of GBM include: the use of amber vials to protect from light; stoppers with specialized coatings to improve shelf-life stability.

Yet another aspect of the invention is an improvement in the therapeutic employment of a substituted hexitol derivative such as dianhydrogalactitol for treatment of GBM made by the use of delivery systems to improve the potential attributes of a pharmaceutical product such as convenience, duration of effect, reduction of toxicities. General examples include: nanocrystals, bioerodible polymers, liposomes, slow release injectable gels, microspheres. Specific inventive examples for a substituted hexitol derivative such as dianhydrogalactitol for treatment of GBM include: the use of nanocrystals; bioerodible polymers; liposomes; slow release injectable gels; microspheres.

Yet another aspect of the invention is an improvement in the therapeutic employment of a substituted hexitol derivative such as dianhydrogalactitol for treatment of GBM made by alterations to the parent molecule with covalent, ionic, or hydrogen bonded moieties to alter the efficacy, toxicity, pharmacokinetics, metabolism, or route of administration. General examples include: polymer systems such as polyethylene glycols, polylactides, polyglycolides, amino acids, peptides, or multivalent linkers. Specific inventive examples for a substituted hexitol derivative such as dianhydrogalactitol for treatment of GBM include: the use of polymer systems such as polyethylene glycols; polylactides; polyglycolides; amino acids; peptides; multivalent linkers.

Yet another aspect of the invention is an improvement in the therapeutic employment of a substituted hexitol derivative such as dianhydrogalactitol for treatment of GBM made by alterations to the molecule such that improved pharmaceutical performance is gained with a variant of the active molecule in that after introduction into the body a portion of the molecule is cleaved to reveal the preferred active molecule. General examples include: enzyme sensitive esters, dimers, Schiff bases. Specific inventive examples for a substituted hexitol derivative such as dianhydrogalactitol for treatment of GBM include: the use of enzyme sensitive esters; dimers; Schiff bases; pyridoxal complexes; caffeine complexes.

Yet another aspect of the invention is an improvement in the therapeutic employment of a substituted hexitol derivative such as dianhydrogalactitol for treatment of GBM made by the use of additional compounds, biological agents that, when administered in the proper fashion, a unique and beneficial effect can be realized. General examples include: inhibitors of multi-drug resistance, specific drug resistance inhibitors, specific inhibitors of selective enzymes, signal transduction inhibitors, repair inhibition. Specific inventive examples for a substituted hexitol derivative such as dianhydrogalactitol for treatment of GBM include: the use of inhibitors of multi-drug resistance; specific drug resistance inhibitors; specific inhibitors of selective enzymes; signal transduction inhibitors; repair inhibition; topoisomerase inhibitors with non-overlapping side effects.

Yet another aspect of the invention is an improvement in the therapeutic employment of a substituted hexitol derivative such as dianhydrogalactitol for treatment of GBM made by the use of the substituted hexitol derivative such as dianhydrogalactitol in combination as sensitizers/potentiators with biological response modifiers. General examples include: use in combination as sensitizers/potentiators with biological response modifiers, cytokines, lymphokines, therapeutic antibodies, antisense therapies, gene therapies. Specific inventive examples for a substituted hexitol derivative such as dianhydrogalactitol for treatment of GBM include: use in combination as sensitizers/potentiators with biological response modifiers; cytokines; lymphokines; therapeutic antibodies such as Avastin, Herceptin, Rituxan, and Erbitux; antisense therapies; gene therapies; ribozymes; RNA interference; or vaccines.

Yet another aspect of the invention is an improvement in the therapeutic employment of a substituted hexitol derivative such as dianhydrogalactitol for treatment of GBM made by exploiting the selective use of the substituted hexitol derivative such as dianhydrogalactitol to overcome developing or complete resistance to the efficient use of biotherapeutics. General examples include: tumors resistant to the effects of biological response modifiers, cytokines, lymphokines, therapeutic antibodies, antisense therapies, gene therapies. Specific inventive examples for a substituted hexitol derivative such as dianhydrogalactitol for treatment of GBM include: the use against tumors resistant to the effects of biological response modifiers; cytokines; lymphokines; therapeutic antibodies; antisense therapies; therapies such as Avastin, Rituxan, Herceptin, Erbitux; gene therapies; ribozymes; RNA interference; and vaccines.

Yet another aspect of the invention is an improvement in the therapeutic employment of a substituted hexitol derivative such as dianhydrogalactitol for treatment of GBM made by exploiting their use in combination with ionizing radiation, phototherapies, heat therapies, or radio-frequency generated therapies. General examples include: hypoxic cell sensitizers, radiation sensitizers/protectors, photosensitizers, radiation repair inhibitors. Specific inventive examples for a substituted hexitol derivative such as dianhydrogalactitol for treatment of GBM include: use in combination with ionizing radiation; use in combination with hypoxic cell sensitizers; use in combination with radiation sensitizers/protectors; use in combination with photosensitizers; use in combination with radiation repair inhibitors; use in combination with thiol depletion; use in combination with vaso-targeted agents; use in combination with use with radioactive seeds; use in combination with radionuclides; use in combination with radiolabeled antibodies; use in combination with brachytherapy. This is useful because radiation therapy is almost always undertaken early in the treatment of GBM and improvements in the efficacy of such radiation therapy or the ability to exert a synergistic effect by combining radiation therapy with the administration of a substituted hexitol derivative such as dianhydrogalactitol is significant.

Yet another aspect of the invention is an improvement in the therapeutic employment of a substituted hexitol derivative such as dianhydrogalactitol for treatment of GBM made by optimizing its utility by determining the various mechanisms of action, biological targets of a compound for greater understanding and precision to better exploit the utility of the molecule. Specific inventive examples for a substituted hexitol derivative such as dianhydrogalactitol for treatment of GBM include: the use with inhibitors of poly-ADP ribose polymerase; agents that effect vasculature or vasodilation; oncogenic targeted agents; signal transduction inhibitors;

EGFR inhibition; Protein Kinase C inhibition; Phospholipase C downregulation; Jun downregulation; histone genes; VEGF; ornithine decarboxylase; ubiquitin C; jun D; v-jun; GPCRs; protein kinase A; telomerase, prostate specific genes; protein kinases other than protein kinase A; histone deacetylase; and tyrosine kinase inhibitors.

Yet another aspect of the invention is an improvement in the therapeutic employment of a substituted hexitol derivative such as dianhydrogalactitol for treatment of GBM made by more precise identification and exposure of the compound to those select cell populations where the compound's effect can be maximally exploited, particularly GBM tumor cells. Specific inventive examples for a substituted hexitol derivative such as dianhydrogalactitol for treatment of GBM include: use against radiation sensitive cells; use against radiation resistant cells; or use against energy depleted cells.

Yet another aspect of the invention is an improvement in the therapeutic employment of a substituted hexitol derivative such as dianhydrogalactitol for treatment of GBM made by use of an agent that counteracts myelosuppression. Specific inventive examples for a substituted hexitol derivative such as dianhydrogalactitol for treatment of GBM include use of dithiocarbamates to counteract myelosuppression.

Yet another aspect of the invention is an improvement in the therapeutic employment of a substituted hexitol derivative such as dianhydrogalactitol for treatment of GBM made by use of an agent that increases the ability of the substituted hexitol to pass through the blood-brain barrier. Specific examples for a substituted hexitol derivative such as dianhydrogalactitol for treatment of GBM include chimeric peptides; compositions comprising either avidin or an avidin fusion protein bonded to a biotinylated substituted hexitol derivative; neutral liposomes that are pegylated and that incorporate the substituted hexitol derivative and wherein the polyethylene glycol strands are conjugated to at least one transportable peptide or targeting agent; a humanized murine antibody that binds to the human insulin receptor linked to the substituted hexitol derivative through an avidin-biotin linkage; and a fusion protein linked to the hexitol through an avidin-biotin linkage.

Accordingly, one aspect of the present invention is a method to improve the efficacy and/or reduce the side effects of the administration of a substituted hexitol derivative such as dianhydrogalactitol for treatment of GBM comprising the steps of:

(1) identifying at least one factor or parameter associated with the efficacy and/or occurrence of side effects of the administration of the substituted hexitol derivative such as dianhydrogalactitol for treatment of GBM; and (2) modifying the factor or parameter to improve the efficacy and/or reduce the side effects of the administration of the substituted hexitol derivative such as dianhydrogalactitol for treatment of GBM.

Typically, the factor or parameter is selected from the group consisting of:
(1) dose modification;
(2) route of administration;
(3) schedule of administration;
(4) indications for use;
(5) selection of disease stage;
(6) other indications;
(7) patient selection;
(8) patient/disease phenotype;
(9) patient/disease genotype;
(10) pre/post-treatment preparation;
(11) toxicity management;
(12) pharmacokinetic/pharmacodynamic monitoring;
(13) drug combinations;
(14) chemosensitization;
(15) chemopotentiation;
(16) post-treatment patient management;
(17) alternative medicine/therapeutic support;
(18) bulk drug product improvements;
(19) diluent systems;
(20) solvent systems;
(21) excipients;
(22) dosage forms;
(23) dosage kits and packaging;
(24) drug delivery systems;
(25) drug conjugate forms;
(26) compound analogs;
(27) prodrugs;
(28) multiple drug systems;
(29) biotherapeutic enhancement;
(30) biotherapeutic resistance modulation;
(31) radiation therapy enhancement;
(32) novel mechanisms of action;
(33) selective target cell population therapeutics;
(34) use of an agent that counteracts myelosuppression; and
(35) use of an agent that increases the ability of the substituted hexitol to pass through the blood-brain barrier.

As detailed above, in general, the substituted hexitol derivative usable in methods and compositions according to the present invention include galactitols, substituted galacitols, dulcitols, and substituted dulcitols, including dianhydrogalactitol, diacetyldianhydrogalactitol, dibromodulcitol, and derivatives and analogs thereof. Typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the substituted hexitol derivative is dianhydrogalactitol.

When the improvement made by is dose modification, the dose modification can be, but is not limited to, at least one dose modification selected from the group consisting of:
(a) continuous i.v. infusion for hours to days;
(b) biweekly administration;
(c) doses greater than 5 mg/m$^2$/day;
(d) progressive escalation of dosing from 1 mg/m$^2$/day based on patient tolerance;
(e) use of caffeine to modulate metabolism;
(f) use of isoniazid to modulate metabolism;
(g) selected and intermittent boosting of dosage administration;
(h) administration of single and multiple doses escalating from 5 mg/m$^2$/day via bolus;
(i) oral dosages of below 30 mg/m$^2$;
(j) oral dosages of above 130 mg/m$^2$;
(k) oral dosages up to 40 mg/m$^2$ for 3 days and then a nadir/recovery period of 18-21 days;
(l) dosing at a lower level for an extended period (e.g., 21 days);
(m) dosing at a higher level;
(n) dosing with a nadir/recovery period longer than 21 days;
(o) dosing at a level to achieve a concentration of the substituted hexitol derivative such as dianhydrogalactitol in the cerebrospinal fluid (CSF) of equal to or greater than 5 μM;
(p) dosing at a level to achieve a cytotoxic concentration in the CSF;

(q) the use of a substituted hexitol derivative such as dianhydrogalactitol as a single cytotoxic agent;
(r) administration on a 33-day cycle with a cumulative dose of about 9 mg/m$^2$;
(s) administration on a 33-day cycle with a cumulative dose of about 10 mg/m$^2$;
(t) administration on a 33-day cycle with a cumulative dose of about 20 mg/m$^2$;
(u) administration on a 33-day cycle with a cumulative dose of about 40 mg/m$^2$;
(v) administration on a 33-day cycle with a cumulative dose of about 80 mg/m$^2$;
(w) administration on a 33-day cycle with a cumulative dose of about 160 mg/m$^2$;
(x) administration on a 33-day cycle with a cumulative dose of about 240 mg/m$^2$;
(y) administration so that the plasma half-life is about 1-2 hours;
(xxvi) administration so that the $C_{max}$ is <200 ng/ml; and
(xxvii) administration so that the substituted hexitol derivative has a half-life of >20 hours in the cerebrospinal fluid.

When the improvement is made by route of administration, the route of administration can be, but is not limited to, at least one route of administration selected from the group consisting of:
(a) topical administration;
(b) oral administration;
(c) slow release oral delivery;
(d) intrathecal administration;
(e) intraarterial administration;
(f) continuous infusion;
(g) intermittent infusion;
(h) intravenous administration, such as intravenous administration for 30 minutes;
(i) administration through a longer infusion;
(j) administration through IV push; and
(k) administration to maximize the concentration of the substituted hexitol derivative such as dianhydrogalactitol in the CSF.

When the improvement is made by schedule of administration, the schedule of administration can be, but is not limited to, at least one schedule of administration selected from the group consisting of:
(a) daily administration;
(b) weekly administration;
(c) weekly administration for three weeks;
(d) biweekly administration;
(e) biweekly administration for three weeks with a 1-2 week rest period;
(f) intermittent boost dose administration;
(g) daily administration for one week for multiple weeks; and
(h) administration on days 1, 2, and 3 of a 33-day cycle.

When the improvement is made by selection of disease stage, the selection of disease stage can be, but is not limited to, at least one selection of disease stage selected from the group consisting of:
(a) use in an appropriate disease stage for GBM;
(b) use with an angiogenesis inhibitor to prevent or limit metastatic spread;
(c) use for newly diagnosed disease;
(d) use for recurrent disease;
(e) use for resistant or refractory disease; and
(f) use for childhood glioblastoma.

When the improvement is made by patient selection, the patient selection can be, but is not limited to, a patient selection carried out by a criterion selected from the group consisting of:
(a) selecting patients with a disease condition characterized by a high level of a metabolic enzyme selected from the group consisting of histone deacetylase and ornithine decarboxylase;
(b) selecting patients with a low or high susceptibility to a condition selected from the group consisting of thrombocytopenia and neutropenia;
(c) selecting patients intolerant of GI toxicities;
(d) selecting patients characterized by over- or under-expression of a gene selected from the group consisting of c-Jun, a GPCR, a signal transduction protein, VEGF, a prostate-specific gene, and a protein kinase.
(e) selecting patients characterized by carrying extra copies of the EGFR gene for GBM;
(f) selecting patients characterized by mutations in at least one gene selected from the group consisting of TP53, PDGFRA, IDH1, and NF1 for GBM;
(g) selecting patients characterized by methylation or lack of methylation of the promoter of the MGMT gene;
(h) selecting patients characterized by the existence of an IDH1 mutation;
(i) selecting patients characterized by the presence of IDH1 wild-type gene;
(j) selecting patients characterized by the presence of 1p/19q co-deletion;
(k) selecting patients characterized by the absence of an 1p/19q co-deletion;
(l) selecting patients characterized by an unmethylated promoter region of MGMT (O$^6$-methylguanine methyltransferase);
(m) selecting patients characterized by a methylated promoter region of MGMT;
(n) selecting patients characterized by a high expression of MGMT;
(o) selecting patients characterized by a low expression of MGMT; and
(p) selecting patients characterized by a mutation in EGFR, including, but not limited to EGFR Variant III.

The cellular proto-oncogene c-Jun encodes a protein that, in combination with c-Fos, forms the AP-1 early response transcription factor. This proto-oncogene plays a key role in transcription and interacts with a large number of proteins affecting transcription and gene expression. It is also involved in proliferation and apoptosis of cells that form part of a number of tissues, including cells of the endometrium and glandular epithelial cells. G-protein coupled receptors (GPCRs) are important signal transducing receptors. The superfamily of G protein coupled receptors includes a large number of receptors. These receptors are integral membrane proteins characterized by amino acid sequences that contain seven hydrophobic domains, predicted to represent the transmembrane spanning regions of the proteins. They are found in a wide range of organisms and are involved in the transmission of signals to the interior of cells as a result of their interaction with heterotrimeric G proteins. They respond to a diverse range of agents including lipid analogues, amino acid derivatives, small molecules such as epinephrine and dopamine, and various sensory stimuli. The properties of many known GPCR are summarized in S. Watson & S. Arkinstall, "The G-Protein Linked Receptor Facts Book" (Academic Press, London, 1994), incorporated herein by this reference. GPCR receptors include, but are not limited to, acetylcholine receptors, β-adrenergic receptors, β₃-adrenergic receptors, serotonin (5-hydroxytryptamine) receptors, dopamine receptors, adenosine receptors, angiotensin Type II receptors, bradykinin receptors, calcitonin receptors, calcitonin gene-related receptors, cannabinoid receptors, cholecystokinin receptors, chemokine receptors, cytokine receptors, gastrin receptors, endothelin receptors, γ-aminobutyric acid (GABA) receptors, galanin receptors, glucagon receptors, glutamate receptors, luteinizing hormone receptors, choriogonadotrophin receptors, follicle-stimulating hormone receptors, thyroid-stimulating hormone receptors, gonadotrophin-releasing hormone receptors, leukotriene receptors, Neuropeptide Y receptors, opioid receptors, parathyroid hormone receptors, platelet activating factor receptors, prostanoid (prostaglandin) receptors, somatostatin receptors, thyrotropin-releasing hormone receptors, vasopressin and oxytocin receptors.

EGFR mutations can be associated with sensitivity to therapeutic agents such as gefitinib, as described in J. G. Paez et al., "EGFR Mutations in Lung Cancer: Correlation with Clinical Response to Gefitinib," *Science* 304: 1497-1500 (2004), incorporated herein by this reference. One specific mutation in EGFR that is associated with resistance to tyrosine kinase inhibitors is known as EGFR Variant III, which is described in C. A. Learn et al., "Resistance to Tyrosine Kinase Inhibition by Mutant Epidermal Growth Factor Variant III Contributes to the Neoplastic Phenotype of Glioblastoma Multiforme," *Clin. Cancer Res.* 10: 3216-3224 (2004), incorporated herein by this reference. EGFR Variant III is characterized by a consistent and tumor-specific in-frame deletion of 801 bp from the extracellular domain that splits a codon and produces a novel glycine at the fusion junction. This mutation encodes a protein with a constitutively active thymidine kinase that enhances the tumorigenicity of the cells carrying this mutation. This mutated protein sequence is clonally expressed on a significant proportion of glioblastomas but is absent from normal tissues.

When the improvement is made by analysis of patient or disease phenotype, the analysis of patient or disease phenotype can be, but is not limited to, a method of analysis of patient or disease phenotype carried out by a method selected from the group consisting of:
 (a) use of a diagnostic tool, a diagnostic technique, a diagnostic kit, or a diagnostic assay to confirm a patient's particular phenotype;
 (b) use of a method for measurement of a marker selected from the group consisting of histone deacetylase, ornithine decarboxylase, VEGF, a protein that is a gene product of jun, and a protein kinase;
 (c) surrogate compound dosing; and
 (d) low dose pre-testing for enzymatic status.

When the improvement is made by analysis of patient or disease genotype, the analysis of patient or disease genotype can be, but is not limited to, a method of analysis of patient or disease genotype carried out by a method selected from the group consisting of:
 (a) use of a diagnostic tool, a diagnostic technique, a diagnostic kit, or a diagnostic assay to confirm a patient's particular genotype;
 (b) use of a gene chip;
 (c) use of gene expression analysis;
 (d) use of single nucleotide polymorphism (SNP) analysis;
 (e) measurement of the level of a metabolite or a metabolic enzyme;
 (f) determination of mutation of PDGFRA gene;
 (g) determination of mutation of IDH1 gene;
 (h) determination of mutation of NF1 gene;
 (i) determination of copy number of the EGFR gene;
 (j) determination of status of methylation of promoter of MGMT gene;
 (k) determination of the existence of an IDH1 mutation;
 (l) determination of the existence of IDH1 wild-type;
 (m) determination of the existence of a 1p/19q co-deletion;
 (n) determination of the absence of a 1p/19q co-deletion;
 (o) determination of the existence of an unmethylated promoter region of the MGMT gene;
 (p) determination of the existence of a methylated promoter region of the MGMT gene;
 (q) determination of the existence of high expression of MGMT; and
 (r) determination of the existence of low expression of MGMT.

The use of gene chips is described in A. J. Lee & S. Ramaswamy, "DNA Microarrays in Biological Discovery and Patient Care" in *Essentials of Genomic and Personalized Medicine* (G. S. Ginsburg & H. F. Willard, eds., Academic Press, Amsterdam, 2010), ch. 7, pp. 73-88, incorporated herein by this reference.

When the method is the use of single nucleotide polymorphism (SNP) analysis, the SNP analysis can be carried out on a gene selected from the group consisting of histone deacetylase, ornithine decarboxylase, VEGF, a prostate specific gene, c-Jun, and a protein kinase. The use of SNP analysis is described in S. Levy and Y.-H. Rogers, "DNA Sequencing for the Detection of Human Genome Variation" in *Essentials of Genomic and Personalized Medicine* (G. S. Ginsburg & H. F. Willard, eds., Academic Press, Amsterdam, 2010), ch. 3, pp. 27-37, incorporated herein by this reference.

Still other genomic techniques such as copy number variation analysis and analysis of DNA methylation can be employed. Copy number variation analysis is described in C. Lee et al., "Copy Number Variation and Human Health" in *Essentials of Genomic and Personalized Medicine* (G. S. Ginsburg & H. F. Willard, eds., Academic Press, Amsterdam, 2010), ch. 5, pp. 46-59, incorporated herein by this reference. This is particularly significant for GBM as an increase in copy number of EGFR is associated with particular subtypes of GBM. DNA methylation analysis is described in S. Cottrell et al., "DNA Methylation Analysis: Providing New Insight into Human Disease" in *Essentials of Genomic and Personalized Medicine* (G. S. Ginsburg & H. F. Willard, eds., Academic Press, Amsterdam, 2010), ch. 6, pp. 60-72, incorporated herein by this reference. This is particularly significant for GBM in that the prognosis for GBM varies with the degree of methylation of the promoter of the MGMT gene.

When the improvement is made by pre/post-treatment preparation, the pre/post-treatment preparation can be, but is not limited to, a method of pre/post treatment preparation selected from the group consisting of:
 (a) the use of colchicine or an analog thereof;
 (b) the use of a diuretic;
 (c) the use of a uricosuric;
 (d) the use of uricase;
 (e) the non-oral use of nicotinamide;
 (f) the use of a sustained-release form of nicotinamide;
 (g) the use of an inhibitor of poly-ADP ribose polymerase;
 (h) the use of caffeine;
 (i) the use of leucovorin rescue;
 (j) infection control; and
 (k) the use of an anti-hypertensive agent.

Uricosurics include, but are not limited to, probenecid, benzbromarone, and sulfinpyrazone. A particularly preferred uricosuric is probenecid. Uricosurics, including probenecid, may also have diuretic activity. Other diuretics are well known in the art, and include, but are not limited to, hydrochlorothiazide, carbonic anhydrase inhibitors, furosemide, ethacrynic acid, amiloride, and spironolactone.

Poly-ADP ribose polymerase inhibitors are described in G. J. Southan & C. Szabó, "Poly(ADP-Ribose) Inhibitors," *Curr. Med. Chem.* 10: 321-240 (2003), incorporated herein by this reference, and include nicotinamide, 3-aminobenzamide, substituted 3,4-dihydroisoquinolin-1(2H)-ones and isoquinolin-1(2H)-ones, benzimidazoles, indoles, phthalazin-1(2H)-ones, quinazolinones, isoindolinones, phenanthridinones, and other compounds.

Leucovorin rescue comprises administration of folinic acid (leucovorin) to patients in which methotrexate has been administered. Leucovorin is a reduced form of folic acid that bypasses dihydrofolate reductase and restores hematopoietic function. Leucovorin can be administered either intravenously or orally.

In one alternative, wherein the pre/post treatment is the use of a uricosuric, the uricosuric is probenecid or an analog thereof.

When the improvement is made by toxicity management, the toxicity management can be, but is not limited to, a method of toxicity management selected from the group consisting of:
(a) the use of colchicine or an analog thereof;
(b) the use of a diuretic;
(c) the use of a uricosuric;
(d) the use of uricase;
(e) the non-oral use of nicotinamide;
(f) the use of a sustained-release form of nicotinamide;
(g) the use of an inhibitor of poly-ADP ribose polymerase;
(h) the use of caffeine;
(i) the use of leucovorin rescue;
(j) the use of sustained-release allopurinol;
(k) the non-oral use of allopurinol;
(l) the use of bone marrow transplants;
(m) the use of a blood cell stimulant;
(n) the use of blood or platelet infusions;
(o) the administration of an agent selected from the group consisting of filgrastim, G-CSF, and GM-CSF;
(p) the application of a pain management technique;
(q) the administration of an anti-inflammatory agent;
(r) the administration of fluids;
(s) the administration of a corticosteroid;
(t) the administration of an insulin control medication;
(u) the administration of an antipyretic;
(v) the administration of an anti-nausea treatment;
(w) the administration of an anti-diarrheal treatment;
(x) the administration of N-acetylcysteine; and
(y) the administration of an antihistamine.

Filgrastim is a granulocytic colony-stimulating factor (G-CSF) analog produced by recombinant DNA technology that is used to stimulate the proliferation and differentiation of granulocytes and is used to treat neutropenia; G-CSF can be used in a similar manner. GM-CSF is granulocyte macrophage colony-stimulating factor and stimulates stem cells to produce granulocytes (eosinophils, neutrophils, and basophils) and monocytes; its administration is useful to prevent or treat infection.

Anti-inflammatory agents are well known in the art and include corticosteroids and non-steroidal anti-inflammatory agents (NSAIDs). Corticosteroids with anti-inflammatory activity include, but are not limited to, hydrocortisone, cortisone, beclomethasone dipropionate, betamethasone, dexamethasone, prednisone, methylprednisolone, triamcinolone, fluocinolone acetonide, and fludrocortisone. Non-steroidal anti-inflammatory agents include, but are not limited to, acetylsalicylic acid (aspirin), sodium salicylate, choline magnesium trisalicylate, salsalate, diflunisal, sulfasalazine, olsalazine, acetaminophen, indomethacin, sulindac, tolmetin, diclofenac, ketorolac, ibuprofen, naproxen, flurbiprofen, ketoprofen, fenoprofin, oxaprozin, mefenamic acid, meclofenamic acid, piroxicam, meloxicam, nabumetone, rofecoxib, celecoxib, etodolac, nimesulide, aceclofenac, alclofenac, alminoprofen, amfenac, ampiroxicam, apazone, araprofen, azapropazone, bendazac, benoxaprofen, benzydamine, bermoprofen, benzpiperylon, bromfenac, bucloxic acid, bumadizone, butibufen, carprofen, cimicoxib, cinmetacin, cinnoxicam, clidanac, clofezone, clonixin, clopirac, darbufelone, deracoxib, droxicam, eltenac, enfenamic acid, epirizole, esflurbiprofen, ethenzamide, etofenamate, etoricoxib, felbinac, fenbufen, fenclofenac, fenclozic acid, fenclozine, fendosal, fentiazac, feprazone, filenadol, flobufen, florifenine, flosulide, flubichin methanesulfonate, flufenamic acid, flufenisal, flunixin, flunoxaprofen, fluprofen, fluproquazone, furofenac, ibufenac, imrecoxib, indoprofen, isofezolac, isoxepac, isoxicam, licofelone, lobuprofen, lomoxicam, lonazolac, loxaprofen, lumaricoxib, mabuprofen, miroprofen, mofebutazone, mofezolac, morazone, nepafanac, niflumic acid, nitrofenac, nitroflurbiprofen, nitronaproxen, orpanoxin, oxaceprol, oxindanac, oxpinac, oxyphenbutazone, pamicogrel, parcetasal, parecoxib, parsalmide, pelubiprofen, pemedolac, phenylbutazone, pirazolac, pirprofen, pranoprofen, salicin, salicylamide, salicylsalicylic acid, satigrel, sudoxicam, suprofen, talmetacin, talniflumate, tazofelone, tebufelone, tenidap, tenoxicam, tepoxalin, tiaprofenic acid, tiaramide, tilmacoxib, tinoridine, tiopinac, tioxaprofen, tolfenamic acid, triflusal, tropesin, ursolic acid, valdecoxib, ximoprofen, zaltoprofen, zidometacin, and zomepirac, and the salts, solvates, analogues, congeners, bioisosteres, hydrolysis products, metabolites, precursors, and prodrugs thereof.

The clinical use of corticosteroids is described in B. P. Schimmer & K. L. Parker, "Adrenocorticotropic Hormone; Adrenocortical Steroids and Their Synthetic Analogs; Inhibitors of the Synthesis and Actions of Adrenocortical Hormones" in *Goodman & Gilman's The Pharmacological Basis of Therapeutics* (L. L. Brunton, ed., 11$^{th}$ ed., McGraw-Hill, New York, 2006), ch. 59, pp. 1587-1612, incorporated herein by this reference.

Anti-nausea treatments include, but are not limited to, ondansetron, metoclopramide, promethazine, cyclizine, hyoscine, dronabinol, dimenhydrinate, diphenhydramine, hydroxyzine, medizine, dolasetron, granisetron, palonosetron, ramosetron, domperidone, haloperidol, chlorpromazine, fluphenazine, perphenazine, prochlorperazine, betamethasone, dexamethasone, lorazepam, and thiethylperazine.

Anti-diarrheal treatments include, but are not limited to, diphenoxylate, difenoxin, loperamide, codeine, racecadotril, octreoside, and berberine.

N-acetylcysteine is an antioxidant and mucolytic that also provides biologically accessible sulfur.

Poly-ADP ribose polymerase (PARP) inhibitors include, but are not limited to: (1) derivatives of tetracycline as described in U.S. Pat. No. 8,338,477 to Duncan et al.; (2) 3,4-dihydro-5-methyl-1(2H)-isoquinoline, 3-aminobenzamide, 6-aminonicotinamide, and 8-hydroxy-2-methyl-4 (3H)-quinazolinone, as described in U.S. Pat. No. 8,324,282 by Gerson et al.; (3) 6-(5H)-phenanthridinone and 1,5-isoquinolinediol, as described in U.S. Pat. No. 8,324,262 by Yuan et al.; (4) (R)-3-[2-(2-hydroxymethylpyrrolidin-1-yl) ethyl]-5-methyl-2H-isoquinolin-1-one, as described in U.S. Pat. No. 8,309,573 to Fujio et al.; (5) 6-alkenyl-substituted 2-quinolinones, 6-phenylalkyl-substituted quinolinones, 6-alkenyl-substituted 2-quinoxalinones, 6-phenylalkyl-substituted 2-quinoxalinones, substituted 6-cyclohexylalkyl substituted 2-quinolinones, 6-cyclohexylalkyl substituted 2-quinoxalinones, substituted pyridones, quinazolinone derivatives, phthalazine derivatives, quinazolinedione derivatives, and substituted 2-alkyl quinazolinone derivatives, as described in U.S. Pat. No. 8,299,256 to Vialard et al.; (6) 5-bromoisoquinoline, as described in U.S. Pat. No. 8,299,088 to Mateucci et al.; (7) 5-bis-(2-chloroethyl) amino]-1-methyl-2-benzimidazolebutyric acid, 4-iodo-3-nitrobenzamide, 8-fluoro-5-(4-((methylamino)methyl)phenyl)-3,4-dihydro-2H-azepino[5,4,3-cd]indol-1(6H)-one phosphoric acid, and N-[3-(3,4-dihydro-4-oxo-1-phthalazinyl)phenyl]-4-morpholinebutanamide methanesulfonate, as described in U.S. Pat. No. 8,227,807 to Gallagher et al.; (8) pyridazinone derivatives, as described in U.S. Pat. No. 8,268,827 to Branca et al.; (9) 4-[3-(4-cyclopropanecarbonyl-piperazine-1-carbonyl)-4-fluorobenzyl]-2H-phthalazin-1-one, as described in U.S. Pat. No. 8,247,416 to Menear et al.; (10) tetraaza phenalen-3-one compounds, as described in U.S. Pat. No. 8,236,802 to Xu et al.; (11) 2-substituted-1H-benzimidazole-4-carboxamides, as described in U.S. Pat. No. 8,217,070 to Zhu et al.; (12) substituted 2-alkyl quinazolinones, as described in U.S. Pat. No. 8,188,103 to Van der Aa et al.; (13) 1H-benzimidazole-4-carboxamides, as described in U.S. Pat. No. 8,183,250 to Penning et al.; (14) indenoisoquinolinone analogs, as described in U.S. Pat. No. 8,119,654 to Jagtap et al.; (15) benzoxazole carboxamides, described in U.S. Pat. No. 8,088,760 to Chu et al; (16) diazabenzo[de]anthracen-3-one compounds, described in U.S. Pat. No. 8,058,075 to Xu et al.; (17) dihydropyridophthalazinones, described in U.S. Pat. No. 8,012,976 to Wang et al., (18) substituted azaindoles, described in U.S. Pat. No. 8,008,491 to Jiang et al.; (19) fused tricyclic compounds, described in U.S. Pat. No. 7,956,064 to Chua et al.; (20) substituted 6a,7,8,9-tetrahydropyrido[3,2-e]pyrrolo [1,2-a]pyrazin-6(5H)-ones, described in U.S. Pat. No. 7,928,105 to Gangloff et al.; and (21) thieno[2,3-c]isoquinolines, described in U.S. Pat. No. 7,825,129, all of which patents are incorporated herein by this reference. Other PARP inhibitors are known in the art.

When the improvement is made by pharmacokinetic/pharmacodynamic monitoring, the pharmacokinetic/pharmacodynamic monitoring can be, but is not limited to a method selected from the group consisting of:
  (a) multiple determinations of blood plasma levels; and
  (b) multiple determinations of at least one metabolite in blood or urine.

Typically, determination of blood plasma levels or determination of at least one metabolite in blood or urine is carried out by immunoassays. Methods for performing immunoassays are well known in the art, and include radioimmunoassay, ELISA (enzyme-linked immunosorbent assay), competitive immunoassay, immunoassay employing lateral flow test strips, and other assay methods.

When the improvement is made by drug combination, the drug combination can be, but is not limited to, a drug combination selected from the group consisting of:
  (a) use with topoisomerase inhibitors;
  (b) use with fraudulent nucleosides;
  (c) use with fraudulent nucleotides;
  (d) use with thymidylate synthetase inhibitors;
  (e) use with signal transduction inhibitors;
  (f) use with cisplatin or platinum analogs;
  (g) use with monofunctional alkylating agents;
  (h) use with bifunctional alkylating agents;
  (i) use with alkylating agents that damage DNA at a different place than does dianhydrogalactitol;
  (j) use with anti-tubulin agents;
  (k) use with antimetabolites;
  (l) use with berberine;
  (m) use with apigenin;
  (n) use with amonafide;
  (o) use with colchicine or analogs;
  (p) use with genistein;
  (q) use with etoposide;
  (r) use with cytarabine;
  (s) use with camptothecins;
  (t) use with vinca alkaloids;
  (u) use with 5-fluorouracil;
  (v) use with curcumin;
  (w) use with NF-κB inhibitors;
  (x) use with rosmarinic acid;
  (y) use with mitoguazone;
  (z) use with tetrandrine;
  (aa) use with temozolomide;
  (ab) use with VEGF inhibitors;
  (ac) use with cancer vaccines;
  (ad) use with EGFR inhibitors;
  (ae) use with tyrosine kinase inhibitors; and
  (af) use with poly (ADP-ribose) polymerase (PARP) inhibitors.

Topoisomerase inhibitors include, but are not limited to, irinotecan, topotecan, camptothecin, lamellarin D, amsacrine, etoposide, etoposide phosphate, teniposide, doxorubicin, and ICRF-193.

Fraudulent nucleosides include, but are not limited to, cytosine arabinoside, gemcitabine, and fludarabine; other fraudulent nucleosides are known in the art.

Fraudulent nucleotides include, but are not limited to, tenofovir disoproxil fumarate and adefovir dipivoxil; other fraudulent nucleotides are known in the art.

Thymidylate synthetase inhibitors include, but are not limited to, raltitrexed, pemetrexed, nolatrexed, ZD9331, GS7094L, fluorouracil, and BGC 945.

Signal transduction inhibitors are described in A. V. Lee et al., "New Mechanisms of Signal Transduction Inhibitor Action: Receptor Tyrosine Kinase Down-Regulation and Blockade of Signal Transactivation," *Clin. Cancer Res.* 9: 516s (2003), incorporated herein in its entirety by this reference.

Alkylating agents include, but are not limited to, Shionogi 254-S, aldo-phosphamide analogues, altretamine, anaxirone, Boehringer Mannheim BBR-2207, bendamustine, bestrabucil, budotitane, Wakunaga CA-102, carboplatin, carmustine (BCNU), Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine (CCNU), mafosfamide, melphalan, mitolactol, nimustine (ACNU), Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol, as described in U.S. Pat. No. 7,446,122 by Chao et al., incorporated herein by this reference. Specifically, for treatment of glioblastoma multiforme, alkylating agents such as temozolomide, BCNU, CCNU, and ACNU can be used; these alkylating agents all damage DNA at $O^6$ of guanine, whereas DAG cross-links at $N^7$); one alternative is therefore to use DAG in combination with an alkylating agent that damages DNA at a different place than DAG. The alkylating agent can be a monofunctional alkylating agent or a bifunctional alkylating agent. Monofunctional alkylating agents include, but are not limited to, carmustine lomustine, temozolomide, and dacarbazine, as described in N. Kondo et al., "DNA Damage Induced by Alkylating Agents and Repair Pathways," *J. Nucl. Acids* doi:10.4061/2010/543531 (2010), incorporated herein by this reference; monofunctional alkylating agents also include such agents as methyl methanesulfonate, ethylmethanesulfonate, and N-methyl-N-nitrosoguanidine, as described in J. M. Walling & I. J. Stratford, "Chemosensitization by Monofunctional Alkylating Agents," *Int. J. Radiat. Oncol. Biol. Phys.* 12: 1397-1400 (1986), incorporated herein by this reference. Bifunctional alkylating agents include, but are not limited to, mechlorethamine, chlorambucil, cyclophosphamide, busulfan, nimustine, carmustine, lomustine, fotemustine, and bis-(2-chloroethyl) sulfide (N. Kondo et al. (2010), supra). One significant class of bifunctional alkylating agents includes alkylating agents that target $O^6$ of guanine in DNA.

Anti-tubulin agents include, but are not limited to, vinca alkaloids, taxanes, podophyllotoxin, halichondrin B, and homohalichondrin B.

Antimetabolites include, but are not limited to: methotrexate, pemetrexed, 5-fluorouracil, capecitabine, cytarabine, gemcitabine, 6-mercaptopurine, and pentostatin, alanosine, AG2037 (Pfizer), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrill-Dow DDFC, deazaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

Berberine has antibiotic activity and prevents and suppresses the expression of pro-inflammatory cytokines and E-selectin, as well as increasing adiponectin expression.

Apigenin is a flavone that can reverse the adverse effects of cyclosporine and has chemoprotective activity, either alone or derivatized with a sugar.

Amonafide is a topoisomerase inhibitor and DNA intercalator that has anti-neoplastic activity.

Curcumin is believed to have anti-neoplastic, anti-inflammatory, antioxidant, anti-ischemic, anti-arthritic, and anti-amyloid properties and also has hepatoprotective activity.

NF-κB inhibitors include, but are not limited to, bortezomib.

Rosmarinic acid is a naturally-occurring phenolic antioxidant that also has anti-inflammatory activity.

Mitoguazone is an inhibitor of polyamine biosynthesis through competitive inhibition of S-adenosylmethionine decarboxylase.

Tetrandrine has the chemical structure 6,6',7,12-tetramethoxy-2,2'-dimethyl-1β-berbaman and is a calcium channel blocker that has anti-inflammatory, immunologic, and anti-allergenic effects, as well as an anti-arrhythmic effect similar to that of quinidine. It has been isolated from *Stephania tetranda* and other Asian herbs.

VEGF inhibitors include bevacizumab (Avastin), which is a monoclonal antibody against VEGF, itraconazole, and suramin, as well as batimastat and marimastat, which are matrix metalloproteinase inhibitors, and cannabinoids and derivatives thereof.

Cancer vaccines are being developed. Typically, cancer vaccines are based on an immune response to a protein or proteins occurring in cancer cells that does not occur in normal cells. Cancer vaccines include Provenge for metastatic hormone-refractory prostate cancer, Oncophage for kidney cancer, CimaVax-EGF for lung cancer, MOBILAN, Neuvenge for Her2/neu expressing cancers such as breast cancer, colon cancer, bladder cancer, and ovarian cancer, Stimuvax for breast cancer, and others. Cancer vaccines are described in S. Pejawar-Gaddy & O. Finn, "Cancer Vaccines: Accomplishments and Challenges," *Crit. Rev. Oncol. Hematol.* 67: 93-102 (2008), incorporated herein by this reference.

The epidermal growth factor receptor (EGFR) exists on the cell surface of mammalian cells and is activated by binding of the receptor to its specific ligands, including, but not limited to epidermal growth factor and transforming growth factor α. Upon activation by binding to its growth factor ligands, EGFR undergoes a transition from an inactive monomeric form to an active homodimer, although pre-formed active dimers may exist before ligand binding. In addition to forming active homodimers after ligand binding, EGFR may pair with another member of the ErbB receptor family, such as ErbB2/Her2/neu, to create an activated heterodimer. There is also evidence that clusters of activated EGFRs form, although it is uncertain whether such clustering is important for activation itself or occurs subsequent to activation of individual dimers. EGFR dimerization stimulates its intracellular intrinsic protein-tyrosine kinase activity. As a result, autophosphorylation of several tyrosine residues in the carboxyl-terminal domain of EGFR occurs. These residues include Y992, Y1045, Y1068, Y1148, and Y1171. Such autophosphorylation elicits downstream activation and signaling by several other proteins that associate with the phosphorylated tyrosine residues through their own phosphotyrosine-binding SH2 domains. The signaling of these proteins that associate with the phosphorylated tyrosine residues through their own phosphotyrosine-binding SH2 domains can then initiate several signal transduction cascades and lead to DNA synthesis and cell proliferation. The kinase domain of EGFR can also cross-phosphorylate tyrosine residues of other receptors that it is aggregated with, and can itself be activated in that manner. EGFR is encoded by the c-erbB1 proto-oncogene and has a molecular mass of 170 kDa. It is a transmembrane glycoprotein with a cysteine-rich extracellular region, an intracellular domain containing an uninterrupted tyrosine kinase site, and multiple autophosphorylation sites clustered at the carboxyl-terminal tail as described above. The extracellular portion has been subdivided into four domains: domains I and III, which have 37% sequence identity, are cysteine-poor and conformationally contain the site for ligand (EGF and transforming growing factor α (TGFα) binding. Cysteine-rich domains II and IV contain N-linked glycosylation sites and disulfide bonds, which determine the tertiary conformation of the external domain of the protein molecule. In many human cell lines, TGFα expression has a strong correlation with EGFR overexpression, and therefore TGFα was considered to act in an autocrine manner, stimulating proliferation of the cells in which it is produced via activation of EGFR. Binding of a stimulatory ligand to the EGFR extracellular domain results in receptor dimerization and initiation of intracellular signal transduction, the first step of which is activation of the tyrosine kinase. The earliest consequence of kinase activation is the phosphorylation of its own tyrosine residues (autophosphorylation) as described above. This is followed by association with activation of signal transducers leading to mitogenesis. Mutations that lead to EGFR expression or overactivity have been associated with a number of malignancies, including glioblastoma multiforme. A specific mutation of EGFR known as EGFR Variant III has frequently been observed in glioblastoma (C. T. Kuan et al., "EGF Mutant Receptor VIII as a Molecular Target in Cancer Therapy," *Endocr. Relat. Cancer* 8: 83-96 (2001), incorporated herein by this reference). EGFR is considered an oncogene. Inhibitors of EGFR include, but are not limited to, erlotinib, gefitinib, lapatinib, lapatinib ditosylate, afatinib, canertinib, neratinib, CP-724714, WHI-P154, TAK-285, AST-1306, ARRY-334543, ARRY-380, AG-1478, tyrphostin 9, dacomitinib, desmethylerlotinib, OSI-420, AZD8931, AEE788, pelitinib, CUDC-101, WZ8040, WZ4002, WZ3146, AG-490, XL647, PD153035 HCl, BMS-599626, BIBW 2992, CI 1033, CP 724714, OSI 420, and vandetinib. Particularly preferred EGFR inhibitors include erlotinib, afatinib, and lapatinib.

Tyrosine kinase inhibitors include, but are not limited to, imatinib, gefitinib, erlotinib, sunitinib, sorafenib, foretinib, cederinib, axitinib, carbozantinib, BIBF1120, golvatinib, dovitinib, ZM 306416, ZM 323881 HCl, SAR 131675, semaxinib, telatinib, pazopanib, ponatinib, crenolanib, tivanitib, mubritinib, danusertib, brivanib, fingolimod, saracatinib, rebastinib, quizartinib, tandutinib, amuvatinib, ibrutinib, fostamatinib, crizotinib, and linsitinib. Such tyrosine kinase inhibitors can inhibit tyrosine kinases associated with one or more of the following receptors: VEGFR, EGFR, PDGFR, c-Kit, c-Met, Her-2, FGFR, FLT-3, IGF-1R, ALK, c-RET, and Tie-2. As the activity of epidermal growth factor receptor (EGFR) involves the activity of a tyrosine kinase, the category of tyrosine kinase inhibitors overlaps with the category of EGFR inhibitors. A number of tyrosine kinase inhibitors inhibit the activity of both EGFR and at least one other tyrosine kinase. In general, tyrosine kinase inhibitors can operate by four different mechanisms: competition with adenosine triphosphate (ATP), used by the tyrosine kinase to carry out the phosphorylation reaction; competition with the substrate; competition with both ATP and the substrate; or allosteric inhibition. The activity of these inhibitors is disclosed in P. Yaish et al., "Blocking of EGF-Dependent Cell Proliferation by EGF Receptor Kinase Inhibitors," *Science* 242: 933-935 (1988); A. Gazit et al., "Tyrphostins. 2. Heterocyclic and α-Substituted Benzylidenemalononitrile Tyrphostins as Potent Inhibitors of EGF Receptor and ErbB2/neu Tyrosine Kinases," *J. Med. Chem.* 34: 1896-1907 (1991); N. Osherov et al., "Selective Inhibition of the Epidermal Growth Factor and HER2/neu Receptors by Tyrphostins," *J. Biol. Chem.* 268: 11134-11142 (1993); and A. Levitzki & E. Mishani, "Tyrphostins and Other Tyrosine Kinase Inhibitors," *Annu. Rev. Biochem.* 75: 93-109 (2006), all of which are incorporated herein by this reference.

In one alternative, when the drug combination is use with an alkylating agent, the alkylating agent can be selected from the group consisting of BCNU, BCNU wafers (Gliadel), ACNU, CCNU, bendamustine (Treanda), lomustine, and temozolimide (Temodar).

When the improvement is made by chemosensitization, the chemosensitization can comprise, but is not limited to, the use of a substituted hexitol derivative as a chemosensitizer in combination with an agent selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) amonafide;
(m) colchicine or analogs;
(n) genistein;
(o) etoposide;
(p) cytarabine;
(q) camptothecins;
(r) vinca alkaloids;
(s) topoisomerase inhibitors;
(t) 5-fluorouracil;
(u) curcumin;
(v) NF-κB inhibitors;
(w) rosmarinic acid;
(x) mitoguazone;
(y) tetrandrine;
(z) a tyrosine kinase inhibitor;
(aa) an inhibitor of EGFR; and
(ab) an inhibitor of PARP.

When the improvement is made by chemopotentiation, the chemopotentiation can comprise, but is not limited to, the use of a substituted hexitol derivative as a chemopotentiator in combination with an agent selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) amonafide;
(m) colchicine or analogs;
(n) genistein;
(o) etoposide;
(p) cytarabine;
(q) camptothecins;
(r) vinca alkaloids;
(s) 5-fluorouracil;
(t) curcumin;
(u) NF-κB inhibitors;
(v) rosmarinic acid;
(w) mitoguazone;
(x) tetrandrine;
(y) a tyrosine kinase inhibitor;
(z) an inhibitor of EGFR; and
(aa) an inhibitor of PARP.

In one alternative, when the chemopotentiation involves chemopotentiation of an alkylating agent by the activity of dianhydrogalactitol, the alkylating agent can be selected from the group consisting of BCNU, BCNU wafers (Gliadel), CCNU, bendamustine (Treanda), lomustine, ACNU, and temozolimide (Temodar).

When the improvement is made by post-treatment management, the post-treatment management can be, but is not limited to, a method selected from the group consisting of:
  (a) a therapy associated with pain management;
  (b) administration of an anti-emetic;
  (c) an anti-nausea therapy;
  (d) administration of an anti-inflammatory agent;
  (e) administration of an anti-pyretic agent; and
  (f) administration of an immune stimulant.

When the improvement is made by alternative medicine/post-treatment support, the alternative medicine/post-treatment support can be, but is not limited to, a method selected from the group consisting of:
  (a) hypnosis;
  (b) acupuncture;
  (c) meditation;
  (d) a herbal medication created either synthetically or through extraction; and
  (e) applied kinesiology.

In one alternative, when the method is a herbal medication created either synthetically or through extraction, the herbal medication created either synthetically or through extraction can be selected from the group consisting of:
  (a) a NF-κB inhibitor;
  (b) a natural anti-inflammatory;
  (c) an immunostimulant;
  (d) an antimicrobial; and
  (e) a flavonoid, isoflavone, or flavone.

When the herbal medication created either synthetically or through extraction is a NF-κB inhibitor, the NF-κB inhibitor can be selected from the group consisting of parthenolide, curcumin, and rosmarinic acid. When the herbal medication created either synthetically or through extraction is a natural anti-inflammatory, the natural anti-inflammatory can be selected from the group consisting of rhein and parthenolide. When the herbal medication created either synthetically or through extraction is an immunostimulant, the immunostimulant can be a product found in or isolated from *Echinacea*. When the herbal medication created either synthetically or through extraction is an anti-microbial, the anti-microbial can be berberine. When the herbal medication created either synthetically or through extraction is a flavonoid or flavone, the flavonoid, isoflavone, or flavone can be selected from the group consisting of apigenin, genistein, apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin.

When the improvement is made by a bulk drug product improvement, the bulk drug product improvement can be, but is not limited to, a bulk drug product improvement selected from the group consisting of:
  (a) salt formation;
  (b) preparation as a homogeneous crystal structure;
  (c) preparation as a pure isomer;
  (d) increased purity;
  (e) preparation with lower residual solvent content; and
  (f) preparation with lower residual heavy metal content.

When the improvement is made by use of a diluent, the diluent can be, but is not limited to, a diluent selected from the group consisting of:
  (a) an emulsion;
  (b) dimethylsulfoxide (DMSO);
  (c) N-methylformamide (NMF)
  (d) DMF;
  (e) ethanol;
  (f) benzyl alcohol;
  (g) dextrose-containing water for injection;
  (h) Cremophor;
  (i) cyclodextrin; and
  (j) PEG.

When the improvement is made by use of a solvent system, the solvent system can be, but is not limited to, a solvent system selected from the group consisting of:
  (a) an emulsion;
  (b) dimethylsulfoxide (DMSO);
  (c) N-methylformamide (NMF)
  (d) DMF;
  (e) ethanol;
  (f) benzyl alcohol;
  (g) dextrose-containing water for injection;
  (h) Cremophor;
  (i) cyclodextrin; and
  (j) PEG.

When the improvement is made by use of an excipient, the excipient can be, but is not limited to, an excipient selected from the group consisting of:
  (a) mannitol;
  (b) albumin;
  (c) EDTA;
  (d) sodium bisulfite;
  (e) benzyl alcohol;
  (f) a carbonate buffer; and
  (g) a phosphate buffer.

When the improvement is made by use of a dosage form, the dosage form can be, but is not limited to, a dosage form selected from the group consisting of:
  (a) tablets;
  (b) capsules;
  (c) topical gels;
  (d) topical creams;
  (e) patches;
  (f) suppositories; and
  (g) lyophilized dosage fills.

Formulation of pharmaceutical compositions in tablets, capsules, and topical gels, topical creams or suppositories is well known in the art and is described, for example, in United States Patent Application Publication No. 2004/0023290 by Griffin et al., incorporated herein by this reference.

Formulation of pharmaceutical compositions as patches such as transdermal patches is well known in the art and is described, for example, in U.S. Pat. No. 7,728,042 to Eros et al., incorporated herein by this reference.

Lyophilized dosage fills are also well known in the art. One general method for the preparation of such lyophilized dosage fills, applicable to dianhydrogalactitol and derivatives thereof and to diacetyldianhydrogalactitol and derivatives thereof, comprises the following steps:

(1) Dissolve the drug in water for injection precooled to below 10° C. Dilute to final volume with cold water for injection to yield a 40 mg/mL solution.

(2) Filter the bulk solution through an 0.2-μm filter into a receiving container under aseptic conditions. The formulation and filtration should be completed in 1 hour.

(3) Fill nominal 1.0 mL filtered solution into sterilized glass vials in a controlled target range under aseptic conditions.

(4) After the filling, all vials are placed with rubber stoppers inserted in the "lyophilization position" and loaded in the prechilled lyophilizer. For the lyophilizer, shelf temperature is set at +5° C. and held for 1 hour; shelf temperature is then adjusted to −5° C. and held for one hour, and the condenser, set to −60° C., turned on.

(5) The vials are then frozen to 30° C. or below and held for no less than 3 hours, typically 4 hours.

(6) Vacuum is then turned on, the shelf temperature is adjusted to −5° C., and primary drying is performed for 8 hours; the shelf temperature is again adjusted to −5° C. and drying is carried out for at least 5 hours.

(7) Secondary drying is started after the condenser (set at −60° C.) and vacuum are turned on. In secondary drying, the shelf temperature is controlled at +5° C. for 1 to 3 hours, typically 1.5 hours, then at 25° C. for 1 to 3 hours, typically 1.5 hours, and finally at 35-40° C. for at least 5 hours, typically for 9 hours, or until the product is completely dried.

(8) Break the vacuum with filtered inert gas (e.g., nitrogen). Stopper the vials in the lyophilizer.

(9) Vials are removed from the lyophilizer chamber and sealed with aluminum flip-off seals. All vials are visually inspected and labeled with approved labels.

When the improvement is made by use of dosage kits and packaging, the dosage kits and packaging can be, but are not limited to, dosage kits and packaging selected from the group consisting of the use of amber vials to protect from light and the use of stoppers with specialized coatings to improve shelf-life stability.

When the improvement is made by use of a drug delivery system, the drug delivery system can be, but is not limited to, a drug delivery system selected from the group consisting of:

(a) nanocrystals;
(b) bioerodible polymers;
(c) liposomes;
(d) slow release injectable gels; and
(e) microspheres.

Nanocrystals are described in U.S. Pat. No. 7,101,576 to Hovey et al., incorporated herein by this reference.

Bioerodible polymers are described in U.S. Pat. No. 7,318,931 to Okumu et al., incorporated herein by this reference. A bioerodible polymer decomposes when placed inside an organism, as measured by a decline in the molecular weight of the polymer over time. Polymer molecular weights can be determined by a variety of methods including size exclusion chromatography (SEC), and are generally expressed as weight averages or number averages. A polymer is bioerodible if, when in phosphate buffered saline (PBS) of pH 7.4 and a temperature of 37° C., its weight-average molecular weight is reduced by at least 25% over a period of 6 months as measured by SEC. Useful bioerodible polymers include polyesters, such as poly(caprolactone), poly(glycolic acid), poly(lactic acid), and poly(hydroxybutyrate); polyanhydrides, such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly(alkylene oxalate); poly(alkylene succinate); polyhydroxycellulose; chitin; chitosan; and copolymers and mixtures thereof.

Liposomes are well known as drug delivery vehicles. Liposome preparation is described in European Patent Application Publication No. EP 1332755 by Weng et al., incorporated herein by this reference.

Slow release injectable gels are known in the art and are described, for example, in B. Jeong et al., "Drug Release from Biodegradable Injectable Thermosensitive Hydrogel of PEG-PLGA-PEG Triblock Copolymers," *J. Controlled Release* 63: 155-163 (2000), incorporated herein by this reference.

The use of microspheres for drug delivery is known in the art and is described, for example, in H. Okada & H. Taguchi, "Biodegradable Microspheres in Drug Delivery," *Crit. Rev. Ther. Drug Carrier Sys.* 12: 1-99 (1995), incorporated herein by this reference.

When the improvement is made by use of a drug conjugate form, the drug conjugate form can be, but is not limited to, a drug conjugate form selected from the group consisting of:

(a) a polymer system;
(b) polylactides;
(c) polyglycolides;
(d) amino acids;
(e) peptides; and
(f) multivalent linkers.

Polylactide conjugates are well known in the art and are described, for example, in R. Tong & C. Cheng, "Controlled Synthesis of Camptothecin-Polylactide Conjugates and Nanoconjugates," *Bioconjugate Chem.* 21: 111-121 (2010), incorporated by this reference.

Polyglycolide conjugates are also well known in the art and are described, for example, in PCT Patent Application Publication No. WO 2003/070823 by Elmaleh et al., incorporated herein by this reference.

Multivalent linkers are known in the art and are described, for example, in United States Patent Application Publication No. 2007/0207952 by Silva et al., incorporated herein by this reference. For example, multivalent linkers can contain a thiophilic group for reaction with a reactive cysteine, and multiple nucleophilic groups (such as NH or OH) or electrophilic groups (such as activated esters) that permit attachment of a plurality of biologically active moieties to the linker.

Suitable reagents for cross-linking many combinations of functional groups are known in the art. For example, electrophilic groups can react with many functional groups, including those present in proteins or polypeptides. Various combinations of reactive amino acids and electrophiles are known in the art and can be used. For example, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150, incorporated herein by this reference. The reactivity of the cysteine residues can be optimized by appropriate selection of the neighboring amino acid residues. For example, a histidine residue adjacent to the cysteine residue will increase the reactivity of the cysteine residue. Other combinations of reactive amino acids and electrophilic reagents are known in the art. For example, maleimides can react with amino groups, such as the ε-amino group of the side chain of lysine, particularly at higher pH ranges. Aryl halides can also react with such amino groups. Haloacetyl derivatives can react with the imidazolyl side chain nitrogens of histidine, the thioether group of the side chain of methionine, and the .epsilon.-amino group of the side chain of lysine. Many other electrophilic reagents are known that will react with the ε-amino group of the side chain of lysine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146, incorporated herein by this reference. Additionally, electrophilic reagents are known that will react with carboxylate side chains such as those of aspartate and glutamate, such as diazoalkanes and diazoacetyl compounds, carbonyldiimidazole, and carbodiimides. These are described in G. T. Hermanson, "Bioconjugate Techniques" (Academic Press, San Diego, 1996), pp. 152-154, incorporated herein by this reference. Furthermore, electrophilic reagents are known that will react with hydroxyl groups such as those in the side chains of serine and threonine, including reactive haloalkane derivatives. These are described in G. T. Hermanson, "Bioconjugate Techniques" (Academic Press, San Diego, 1996), pp. 154-158, incorporated herein by this reference. In another alternative embodiment, the relative positions of electrophile and nucleophile (i.e., a molecule reactive with an electrophile) are reversed so that the protein has an amino acid residue with an electrophilic group that is reactive with a nucleophile and the targeting molecule includes therein a nucleophilic group. This includes the reaction of aldehydes (the electrophile) with hydroxylamine (the nucleophile), described above, but is more general than that reaction; other groups can be used as electrophile and nucleophile. Suitable groups are well known in organic chemistry and need not be described further in detail.

Additional combinations of reactive groups for cross-linking are known in the art. For example, amino groups can be reacted with isothiocyanates, isocyanates, acyl azides, N-hydroxysuccinimide (NHS) esters, sulfonyl chlorides, aldehydes, glyoxals, epoxides, oxiranes, carbonates, alkylating agents, imidoesters, carbodiimides, and anhydrides. Thiol groups can be reacted with haloacetyl or alkyl halide derivatives, maleimides, aziridines, acryloyl derivatives, acylating agents, or other thiol groups by way of oxidation and the formation of mixed disulfides. Carboxy groups can be reacted with diazoalkanes, diazoacetyl compounds, carbonyldiimidazole, carbodiimides. Hydroxyl groups can be reacted with epoxides, oxiranes, carbonyldiimidazole, N,N'-disuccinimidyl carbonate, N-hydroxysuccinimidyl chloroformate, periodate (for oxidation), alkyl halogens, or isocyanates. Aldehyde and ketone groups can react with hydrazines, reagents forming Schiff bases, and other groups in reductive amination reactions or Mannich condensation reactions. Still other reactions suitable for cross-linking reactions are known in the art. Such cross-linking reagents and reactions are described in G. T. Hermanson, "Bioconjugate Techniques" (Academic Press, San Diego, 1996), incorporated herein by this reference.

When the improvement is made by use of a prodrug system, the prodrug system can be, but is not limited to, a prodrug system selected from the group consisting of:
    (a) the use of enzyme sensitive esters;
    (b) the use of dimers;
    (c) the use of Schiff bases;
    (d) the use of pyridoxal complexes; and
    (e) the use of caffeine complexes.

The use of prodrug systems is described in T. Jarvinen et al., "Design and Pharmaceutical Applications of Prodrugs" in Drug Discovery Handbook (S. C. Gad, ed., Wiley-Interscience, Hoboken, N.J., 2005), ch. 17, pp. 733-796, incorporated herein by this reference. This publication describes the use of enzyme sensitive esters as prodrugs. The use of dimers as prodrugs is described in U.S. Pat. No. 7,879,896 to Allegretti et al., incorporated herein by this reference. The use of peptides in prodrugs is described in S. Prasad et al., "Delivering Multiple Anticancer Peptides as a Single Prodrug Using Lysyl-Lysine as a Facile Linker," *J. Peptide Sci.* 13: 458-467 (2007), incorporated herein by this reference. The use of Schiff bases as prodrugs is described in U.S. Pat. No. 7,619,005 to Epstein et al., incorporated herein by this reference. The use of caffeine complexes as prodrugs is described in U.S. Pat. No. 6,443,898 to Unger et al., incorporated herein by this reference.

When the improvement is made by use of a multiple drug system, the multiple drug system can be, but is not limited to, a multiple drug system selected from the group consisting of:
    (a) use of multi-drug resistance inhibitors;
    (b) use of specific drug resistance inhibitors;
    (c) use of specific inhibitors of selective enzymes;
    (d) use of signal transduction inhibitors;
    (e) use of repair inhibition; and
    (f) use of topoisomerase inhibitors with non-overlapping side effects.

Multi-drug resistance inhibitors are described in U.S. Pat. No. 6,011,069 to Inomata et al., incorporated herein by this reference.

Specific drug resistance inhibitors are described in T. Hideshima et al., "The Proteasome Inhibitor PS-341 Inhibits Growth, Induces Apoptosis, and Overcomes Drug Resistance in Human Multiple Myeloma Cells," *Cancer Res.* 61: 3071-3076 (2001), incorporated herein by this reference.

Repair inhibition is described in N. M. Martin, "DNA Repair Inhibition and Cancer Therapy," *J. Photochem. Photobiol. B* 63: 162-170 (2001), incorporated herein by this reference.

When the improvement is made by biotherapeutic enhancement, the biotherapeutic enhancement can be performed by use in combination as sensitizers/potentiators with a therapeutic agent or technique that can be, but is not limited to, a therapeutic agent or technique selected from the group consisting of:
    (a) cytokines;
    (b) lymphokines;
    (c) therapeutic antibodies;
    (d) antisense therapies;
    (e) gene therapies;
    (f) ribozymes;
    (g) RNA interference; and
    (h) vaccines.

Antisense therapies are described, for example, in B. Weiss et al., "Antisense RNA Gene Therapy for Studying and Modulating Biological Processes," *Cell. Mol. Life Sci.* 55: 334-358 (1999), incorporated herein by this reference.

Ribozymes are described, for example, in S. Pascolo, "RNA-Based Therapies" in *Drug Discovery Handbook* (S. C. Gad, ed., Wiley-Interscience, Hoboken, N.J., 2005), ch. 27, pp. 1273-1278, incorporated herein by this reference.

RNA interference is described, for example, in S. Pascolo, "RNA-Based Therapies" in *Drug Discovery Handbook* (S. C. Gad, ed., Wiley-Interscience, Hoboken, N.J., 2005), ch. 27, pp. 1278-1283, incorporated herein by this reference.

As described above, typically, cancer vaccines are based on an immune response to a protein or proteins occurring in cancer cells that does not occur in normal cells. Cancer vaccines include Provenge for metastatic hormone-refractory prostate cancer, Oncophage for kidney cancer, CimaVax-EGF for lung cancer, MOBILAN, Neuvenge for Her2/neu expressing cancers such as breast cancer, colon cancer, bladder cancer, and ovarian cancer, Stimuvax for breast cancer, and others. Cancer vaccines are described in S. Pejawar-Gaddy & O. Finn, (2008), supra.

When the biotherapeutic enhancement is use in combination as sensitizers/potentiators with a therapeutic antibody, the therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by use of biotherapeutic resistance modulation, the biotherapeutic resistance modulation can be, but is not limited to, use against glioblastoma multiforme tumors resistant to a therapeutic agent or technique selected from the group consisting of:
(a) biological response modifiers;
(b) cytokines;
(c) lymphokines;
(d) therapeutic antibodies;
(e) antisense therapies;
(f) gene therapies;
(g) ribozymes;
(h) RNA interference; and
(i) vaccines.

When the biotherapeutic resistance modulation is use against tumors resistant to therapeutic antibodies, the therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by radiation therapy enhancement, the radiation therapy enhancement can be, but is not limited to, a radiation therapy enhancement agent or technique selected from the group consisting of:
(a) hypoxic cell sensitizers;
(b) radiation sensitizers/protectors;
(c) photosensitizers;
(d) radiation repair inhibitors;
(e) thiol depleters;
(f) vaso-targeted agents;
(g) DNA repair inhibitors;
(h) radioactive seeds;
(i) radionuclides;
(j) radiolabeled antibodies; and
(k) brachytherapy.

A substituted hexitol derivative such as dianhydrogalactitol can be used in combination with radiation for the treatment of glioblastoma multiforme.

Hypoxic cell sensitizers are described in C. C. Ling et al., "The Effect of Hypoxic Cell Sensitizers at Different Irradiation Dose Rates," *Radiation Res.* 109: 396-406 (1987), incorporated herein by this reference. Radiation sensitizers are described in T. S. Lawrence, "Radiation Sensitizers and Targeted Therapies," *Oncology* 17 (Suppl. 13) 23-28 (2003), incorporated herein by this reference. Radiation protectors are described in S. B. Vuyyuri et al., "Evaluation of D-Methionine as a Novel Oral Radiation Protector for Prevention of Mucositis," *Clin. Cancer Res.* 14: 2161-2170 (2008), incorporated herein by this reference. Photosensitizers are described in R. R. Allison & C. H. Sibata, "Oncologic Photodynamic Therapy Photosensitizers: A Clinical Review," *Photodiagnosis Photodynamic Ther.* 7: 61-75 (2010), incorporated herein by this reference. Radiation repair inhibitors and DNA repair inhibitors are described in M. Hingorani et al., "Evaluation of Repair of Radiation-Induced DNA Damage Enhances Expression from Replication-Defective Adenoviral Vectors," *Cancer Res.* 68: 9771-9778 (2008), incorporated herein by this reference. Thiol depleters are described in K. D. Held et al., "Postirradiation Sensitization of Mammalian Cells by the Thiol-Depleting Agent Dimethyl Fumarate," *Radiation Res.* 127: 75-80 (1991), incorporated herein by this reference. Vaso-targeted agents are described in A. L. Seynhaeve et al., "Tumor Necrosis Factor α Mediates Homogeneous Distribution of Liposomes in Murine Melanoma that Contributes to a Better Tumor Response," *Cancer Res.* 67: 9455-9462 (2007). As described above, radiation therapy is frequently employed for the treatment of GBM, so radiation therapy enhancement is significant for this malignancy.

When the improvement is by use of a novel mechanism of action, the novel mechanism of action can be, but is not limited to, a novel mechanism of action that is a therapeutic interaction with a target or mechanism selected from the group consisting of:
(a) inhibitors of poly-ADP ribose polymerase;
(b) agents that affect vasculature or vasodilation;
(c) oncogenic targeted agents;
(d) signal transduction inhibitors;
(e) EGFR inhibition;
(f) protein kinase C inhibition;
(g) phospholipase C downregulation;
(h) Jun downregulation;
(i) histone genes;
(j) VEGF;
(k) ornithine decarboxylase;
(l) ubiquitin C;
(m) Jun D;
(n) v-Jun;
(o) GPCRs;
(p) protein kinase A;
(q) protein kinases other than protein kinase A;
(r) prostate specific genes;
(s) telomerase;
(t) histone deacetylase; and
(u) tyrosine kinase inhibitors.

EGFR inhibition is described in G. Giaccone & J. A. Rodriguez, "EGFR Inhibitors: What Have We Learned from the Treatment of Lung Cancer," *Nat. Clin. Pract. Oncol.* 11: 554-561 (2005), incorporated herein by this reference. Protein kinase C inhibition is described in H. C. Swannie & S. B. Kaye, "Protein Kinase C Inhibitors," *Curr. Oncol. Rep.* 4: 37-46 (2002), incorporated herein by this reference. Phospholipase C downregulation is described in A. M. Martelli et al., "Phosphoinositide Signaling in Nuclei of Friend Cells: Phospholipase C β Downregulation Is Related to Cell Differentiation," *Cancer Res.* 54: 2536-2540 (1994), incorporated herein by this reference. Downregulation of Jun (specifically, c-Jun) is described in A. A. P. Zada et al., "Downregulation of c-Jun Expression and Cell Cycle Regulatory Molecules in Acute Myeloid Leukemia Cells Upon CD44 Ligation," *Oncogene* 22: 2296-2308 (2003), incorporated herein by this reference. The role of histone genes as a target for therapeutic intervention is described in B. Calabretta et al., "Altered Expression of G1-Specific Genes in Human Malignant Myeloid Cells," *Proc. Natl. Acad. Sci. USA* 83: 1495-1498 (1986). The role of VEGF as a target for therapeutic intervention is described in A. Zielke et al., "VEGF-Mediated Angiogenesis of Human Pheochromocytomas Is Associated to Malignancy and Inhibited by anti-VEGF Antibodies in Experimental Tumors," *Surgery* 132: 1056-1063 (2002), incorporated herein by this reference. The role of ornithine decarboxylase as a target for therapeutic intervention is described in J. A. Nilsson et al., "Targeting Ornithine Decarboxylase in Myc-Induced Lymphomagenesis Prevents Tumor Formation," *Cancer Cell* 7:

433-444 (2005), incorporated herein by this reference. The role of ubiquitin C as a target for therapeutic intervention is described in C. Aghajanian et al., "A Phase I Trial of the Novel Proteasome Inhibitor PS341 in Advanced Solid Tumor Malignancies," *Clin. Cancer Res.* 8: 2505-2511 (2002), incorporated herein by this reference. The role of Jun D as a target for therapeutic intervention is described in M. M. Caffarel et al., "JunD Is Involved in the Antiproliferative Effect of Δ$^9$-Tetrahydrocannibinol on Human Breast Cancer Cells," *Oncogene* 27: 5033-5044 (2008), incorporated herein by this reference. The role of v-Jun as a target for therapeutic intervention is described in M. Gao et al., "Differential and Antagonistic Effects of v-Jun and c-Jun," *Cancer Res.* 56: 4229-4235 (1996), incorporated herein by this reference. The role of protein kinase A as a target for therapeutic intervention is described in P. C. Gordge et al., "Elevation of Protein Kinase A and Protein Kinase C in Malignant as Compared With Normal Breast Tissue," *Eur. J. Cancer* 12: 2120-2126 (1996), incorporated herein by this reference. The role of telomerase as a target for therapeutic intervention is described in E. K. Parkinson et al., "Telomerase as a Novel and Potentially Selective Target for Cancer Chemotherapy," *Ann. Med.* 35: 466-475 (2003), incorporated herein by this reference. The role of histone deacetylase as a target for therapeutic intervention is described in A. Melnick & J. D. Licht, "Histone Deacetylases as Therapeutic Targets in Hematologic Malignancies," *Curr. Opin. Hematol.* 9: 322-332 (2002), incorporated herein by this reference.

When the improvement is made by use of selective target cell population therapeutics, the use of selective target cell population therapeutics can be, but is not limited to, a use selected from the group consisting of:

(a) use against radiation sensitive cells;
(b) use against radiation resistant cells; and
(c) use against energy depleted cells.

The improvement can also be made by use of dianhydrogalactitol in combination with ionizing radiation.

When the improvement is made by use of an agent that counteracts myelosuppression, the agent that counteracts myelosuppression can be, but is not limited to, a dithiocarbamate.

U.S. Pat. No. 5,035,878 to Borch et al., incorporated herein by this reference, discloses dithiocarbamates for treatment of myelosuppression; the dithiocarbamates are compounds of the formula $R^1R^2NCS(S)M$ or $R^1R^2NCSS—SC(S)NR^3R^4$, wherein $R^1$, $R^2$, $R^3$, and $R^4$ are the same or different, and $R^1$, $R^2$, $R^3$, and $R^4$ are aliphatic, cycloaliphatic, or heterocycloaliphatic groups that are unsubstituted or substituted by hydroxyl; or wherein one of $R^1$ and $R^2$ and one of $R^3$ and $R^4$ can be hydrogen; or wherein $R^1$, $R^2$, $R^3$, and $R^4$ taken together with the nitrogen atom upon which the pair of R groups is substituted, can be a 5-membered or 6-membered N-heterocyclic ring which is aliphatic or aliphatic interrupted by a ring oxygen or a second ring nitrogen, and M is hydrogen or one equivalent or a pharmaceutically acceptable cation, in which case the rest of the molecule is negatively charged.

U.S. Pat. No. 5,294,430 to Borch et al., incorporated herein by this reference, discloses additional dithiocarbamates for treatment of myelosuppression. In general, these are compounds of Formula (D-I):

(D-I)

wherein:
(i) $R^1$ and $R^2$ are the same or different $C_1$-$C_6$ alkyl groups, $C_3$-$C_6$ cycloalkyl groups, or $C_5$-$C_6$ heterocycloalkyl groups; or
(ii) one of $R^1$ and $R^2$, but not both, can be H; or
(iii) $R^1$ and $R^2$ taken together with the nitrogen atom can be a 5-membered or 6-membered N-heterocyclic ring which is aliphatic or aliphatic interrupted by a ring oxygen or a second ring nitrogen; and
(iv) M is hydrogen or one equivalent of a pharmaceutically acceptable cation, in which case the rest of the molecule is negatively charged; or
(v) M is a moiety of Formula (D-II):

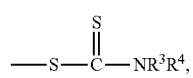
(D-II)

wherein $R^3$ and $R^4$ are defined in the same manner as $R^1$ and $R^2$. Where the group defined by Formula (D-I) is an anion, the cation can be an ammonium cation or can be derived from a monovalent or divalent metal such as an alkali metal or an alkaline earth metal, such as $Na^+$, $K^+$, or $Zn^{+2}$. In the case of the dithiocarbamic acids, the group defined by Formula (D-I) is linked to an ionizable hydrogen atom; typically, the hydrogen atom will dissociate at a pH above about 5.0. Among dithiocarbamates that can be used are: N-methyl,N-ethyldithiocarbamates, hexamethylenedithiocarbamic acid, sodium di(β-hydroxyethyl)dithiocarbamate, various dipropyl, dibutyl and diamyl dithiocarbamates, sodium N-methyl,N-cyclobutylmethyl dithiocarbamate, sodium N-allyl-N-cyclopropylmethyldithiocarbamate, cyclohexylamyldithiocarbamates, dibenzyl-dithiocarbamates, sodium dimethylene-dithiocarbamate, various pentamethylene dithiocarbamate salts, sodium pyrrolidine-N-carbodithioate, sodium piperidine-N-carbodithioate, sodium morpholine-N-carbo-dithioate, α-furfuryl dithiocarbamates and imidazoline dithiocarbamates. Another alternative is a compound where $R^1$ of Formula (D-I) is a hydroxy-substituted or, preferably, a (bis to penta) polyhydroxy-substituted lower alkyl group having up to 6 carbon atoms. For example, $R^1$ can be HO—$CH_2$—CHOH—CHOH—CHOH—CHOH—$CH_2$—. In such compounds, $R^2$ can be H or lower alkyl (unsubstituted or substituted with one or more hydroxyl groups). Steric problems can be minimized when $R^2$ is H, methyl, or ethyl. Accordingly, a particularly preferred compound of this type is an N-methyl-glucamine dithiocarbamate salt, the most preferred cations of these salts being sodium or potassium. Other preferred dithiocarbamates include the alkali or alkaline earth metal salts wherein the anion is di-n-butyldithiocarbamate, di-n-propyldithiocarbamate, pentamethylenedithiocarbamate, or tetramethylene dithiocarbamate.

When the improvement is made by use with an agent that increases the ability of the substituted hexitol to pass through the blood-brain barrier, the agent that increases the ability of the substituted hexitol to pass through the blood-brain barrier can be, but is not limited to:

(a) a chimeric peptide of the structure of Formula (D-III):

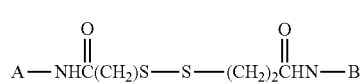
(D-III)

wherein: (A) A is somatostatin, thyrotropin releasing hormone (TRH), vasopressin, alpha interferon, endorphin, muramyl dipeptide or ACTH 4-9 analogue; and (B) B is insulin, IGF-I, IGF-II, transferrin, cationized (basic) albumin or prolactin; or a chimeric peptide of the structure of Formula (D-III) wherein the disulfide conjugating bridge between A and B is replaced with a bridge of Subformula (D-III(a)):

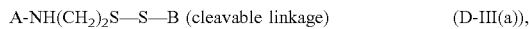

A-NH(CH₂)₂S—S—B (cleavable linkage)        (D-III(a)), wherein the bridge is formed using cysteamine and EDAC as the bridge reagents; or a chimeric peptide of the structure of Formula (D-III) wherein the disulfide conjugating bridge between A and B is replaced with a bridge of Subformula (D-III(b)):

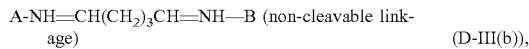

A-NH=CH(CH₂)₃CH=NH—B (non-cleavable linkage)        (D-III(b)), wherein the bridge is formed using glutaraldehyde as the bridge reagent;

(b) a composition comprising either avidin or an avidin fusion protein bonded to a biotinylated substituted hexitol derivative to form an avidin-biotin-agent complex including therein a protein selected from the group consisting of insulin, transferrin, an anti-receptor monoclonal antibody, a cationized protein, and a lectin;

(c) a neutral liposome that is pegylated and incorporates the substituted hexitol derivative, wherein the polyethylene glycol strands are conjugated to at least one transportable peptide or targeting agent;

(d) a humanized murine antibody that binds to the human insulin receptor linked to the substituted hexitol derivative through an avidin-biotin linkage; and (e) a fusion protein comprising a first segment and a second segment: the first segment comprising a variable region of an antibody that recognizes an antigen on the surface of a cell that after binding to the variable region of the antibody undergoes antibody-receptor-mediated endocytosis, and, optionally, further comprises at least one domain of a constant region of an antibody; and the second segment comprising a protein domain selected from the group consisting of avidin, an avidin mutein, a chemically modified avidin derivative, streptavidin, a streptavidin mutein, and a chemically modified streptavidin derivative, wherein the fusion protein is linked to the substituted hexitol by a covalent link to biotin.

Agents that improve penetration of the blood-brain barrier are disclosed in W. M. Pardridge, "The Blood-Brain Barrier: Bottleneck in Brain Drug Development," *NeuroRx* 2: 3-14 (2005), incorporated herein by this reference.

One class of these agents is disclosed in U.S. Pat. No. 4,801,575 to Pardridge, incorporated herein by this reference, which discloses chimeric peptides for delivery of agents across the blood-brain barrier. These chimeric peptides include peptides of the general structure of Formula (D-IV):

wherein:

(i) A is somatostatin, thyrotropin releasing hormone (TRH), vasopressin, alpha interferon, endorphin, muramyl dipeptide or ACTH 4-9 analogue; and (ii) B is insulin, IGF-I, IGF-II, transferrin, cationized (basic) albumin or prolactin. In another alternative, the disulfide conjugating bridge between A and B is replaced with a bridge of Subformula (D-IV(a)):

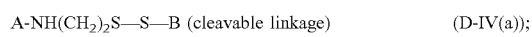

A-NH(CH₂)₂S—S—B (cleavable linkage)        (D-IV(a));

the bridge of Subformula (D-III(a)) is formed when cysteamine and EDAC are employed as the bridge reagents. In yet another alternative, the disulfide conjugating bridge between A and B is replaced with a bridge of Subformula (D-IV(b)):

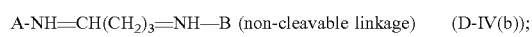

A-NH=CH(CH₂)₃=NH—B (non-cleavable linkage)        (D-IV(b));

the bridge of Subformula (D-III(b)) is formed when glutaraldehyde is employed as the bridge reagent.

U.S. Pat. No. 6,287,792 to Pardridge et al., incorporated herein by this reference, discloses methods and compositions for delivery of agents across the blood-brain barrier comprising either avidin or an avidin fusion protein bonded to a biotinylated agent to form an avidin-biotin-agent complex. The avidin fusion protein can include the amino acid sequences of proteins such as insulin or transferrin, an anti-receptor monoclonal antibody, a cationized protein, or a lectin.

U.S. Pat. No. 6,372,250 to Pardridge, incorporated herein by this reference, discloses methods and compositions for delivery of agents across the blood-brain barrier employing liposomes. The liposomes are neutral liposomes. The surface of the neutral liposomes is pegylated. The polyethylene glycol strands are conjugated to transportable peptides or other targeting agents. Suitable targeting agents include insulin, transferrin, insulin-like growth factor, or leptin. Alternatively, the surface of the liposome could be conjugated with 2 different transportable peptides, one peptide targeting an endogenous BBB receptor and the other targeting an endogenous BCM (brain cell plasma membrane) peptide. The latter could be specific for particular cells within the brain, such as neurons, glial cells, pericytes, smooth muscle cells, or microglia. Targeting peptides may be endogenous peptide ligands of the receptors, analogues of the endogenous ligand, or peptidomimetic MAbs that bind the same receptor of the endogenous ligand. Transferrin receptor-specific peptidomimetic monoclonal antibodies can be used as transportable peptides. Monoclonal antibodies to the human insulin receptor can be used as transportable peptides. The conjugation agents which are used to conjugate the blood-barrier targeting agents to the surface of the liposome can be any of the well-known polymeric conjugation agents such as sphingomyelin, polyethylene glycol (PEG) or other organic polymers, with PEG preferred. The liposomes preferably have diameters of less than 200 nanometers. Liposomes having diameters of between 50 and 150 nanometers are preferred. Especially preferred are liposomes or other nanocontainers having external diameters of about 80 nanometers. Suitable types of liposomes are made with neutral phospholipids such as 1-palmitoyl-2-oleoyl-sn-glycerol-3-phosphocholine (POPC), diphosphatidyl phosphocholine, distearoylphosphatidylethanolamine (DSPE), or cholesterol. The transportable peptide is linked to the liposome as follows: A transportable peptide such as insulin or an HIRMAb is thiolated and conjugated to a maleimide group on the tip of a small fraction of the PEG strands; or, surface carboxyl groups on a transportable peptide such as transferrin or a TfRMAb are conjugated to a hydrazide (Hz) moiety on the tip of the PEG strand with a carboxyl activator group such as N-methyl-N'-3(dimethylaminopropyl)carbodiimide hydrochloride (EDAC); a transportable peptide is thiolated and conjugated via a disulfide linker to the liposome that has been reacted with N-succinimidyl 3-(2-pyridylthio)propionate (SPDP); or a transportable peptide is conjugated to the surface of the liposome with avidin-biotin technology, e.g., the transportable peptide is mono-biotinylated and is bound to avidin or streptavidin (SA), which is attached to the surface of the PEG strand.

U.S. Pat. No. 7,388,079 to Pardridge et al., incorporated herein by this reference, discloses the use of a humanized murine antibody that binds to the human insulin receptor; the humanized murine antibody can be linked to the agent to be delivered through an avidin-biotin linkage.

U.S. Pat. No. 8,124,095 to Pardridge et al., incorporated herein by this reference, discloses monoclonal antibodies that are capable of binding to an endogenous blood-brain barrier receptor-mediated transport system and are thus capable of serving as a vector for transport of a therapeutic agent across the BBB. The monoclonal antibody can be, for example, an antibody specifically binding the human insulin receptor on the human BBB.

United States Patent Application Publication No. 2005/0085419 by Morrison et al., incorporated herein by this reference, discloses a fusion protein for delivery of a wide variety of agents to a cell via antibody-receptor-mediated endocytosis comprises a first segment and a second segment: the first segment comprising a variable region of an antibody that recognizes an antigen on the surface of a cell that after binding to the variable region of the antibody undergoes antibody-receptor-mediated endocytosis, and, optionally, further comprises at least one domain of a constant region of an antibody; and the second segment comprising a protein domain selected from the group consisting of avidin, an avidin mutein, a chemically modified avidin derivative, streptavidin, a streptavidin mutein, and a chemically modified streptavidin derivative. Typically, the antigen is a protein. Typically, the protein antigen on the surface of the cell is a receptor such as a transferrin receptor- or an insulin receptor. The invention also includes an antibody construct incorporating the fusion protein that is either a heavy chain or a light chain together with a complementary light chain or heavy chain to form an intact antibody molecule. The therapeutic agent can be a non-protein molecule and can be linked covalently to biotin.

Another aspect of the present invention is a composition to improve the efficacy and/or reduce the side effects of suboptimally administered drug therapy employing a substituted hexitol derivative for the treatment of GBM comprising an alternative selected from the group consisting of:

(i) a therapeutically effective quantity of a modified substituted hexitol derivative or a derivative, analog, or prodrug of a substituted hexitol derivative or a modified substituted hexitol derivative, wherein the modified substituted hexitol derivative or the derivative, analog or prodrug of the substituted hexitol derivative or modified substituted hexitol derivative possesses increased therapeutic efficacy or reduced side effects for treatment of GBM as compared with an unmodified substituted hexitol derivative;

(ii) a composition comprising:
  (a) a therapeutically effective quantity of a substituted hexitol derivative, a modified substituted hexitol derivative, or a derivative, analog, or prodrug of a substituted hexitol derivative or a modified substituted hexitol derivative; and
  (b) at least one additional therapeutic agent, therapeutic agent subject to chemosensitization, therapeutic agent subject to chemopotentiation, diluent, excipient, solvent system, drug delivery system, agent to counteract myelosuppression, or agent that increases the ability of the substituted hexitol to pass through the blood-brain barrier, wherein the composition possesses increased therapeutic efficacy or reduced side effects for treatment of GBM as compared with an unmodified substituted hexitol derivative;

(iii) a therapeutically effective quantity of a substituted hexitol derivative, a modified substituted hexitol derivative or a derivative, analog, or prodrug of a substituted hexitol derivative or a modified substituted hexitol derivative that is incorporated into a dosage form, wherein the substituted hexitol derivative, the modified substituted hexitol derivative or the derivative, analog, or prodrug of a substituted hexitol derivative or a modified substituted hexitol derivative incorporated into the dosage form possesses increased therapeutic efficacy or reduced side effects for treatment of GBM as compared with an unmodified substituted hexitol derivative;

(iv) a therapeutically effective quantity of a substituted hexitol derivative, a modified substituted hexitol derivative or a derivative, analog, or prodrug of a substituted hexitol derivative or a modified substituted hexitol derivative that is incorporated into a dosage kit and packaging, wherein the substituted hexitol derivative, the modified substituted hexitol derivative or the derivative, analog, or prodrug of a substituted hexitol derivative or a modified substituted hexitol derivative incorporated into the dosage kit and packaging possesses increased therapeutic efficacy or reduced side effects for treatment of GBM as compared with an unmodified substituted hexitol derivative; and (v) a therapeutically effective quantity of a substituted hexitol derivative, a modified substituted hexitol derivative or a derivative, analog, or prodrug of a substituted hexitol derivative or a modified substituted hexitol derivative that is subjected to a bulk drug product improvement, wherein substituted hexitol derivative, a modified substituted hexitol derivative or a derivative, analog, or prodrug of a substituted hexitol derivative or a modified substituted hexitol derivative subjected to the bulk drug product improvement possesses increased therapeutic efficacy or reduced side effects for treatment of GBM as compared with an unmodified substituted hexitol derivative.

As detailed above, typically the unmodified substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the unmodified substituted hexitol derivative is dianhydrogalactitol.

In one alternative, the composition comprises a drug combination comprising:
  (i) a substituted hexitol derivative; and
  (ii) an additional therapeutic agent selected from the group consisting of:
    (a) topoisomerase inhibitors;
    (b) fraudulent nucleosides;
    (c) fraudulent nucleotides;
    (d) thymidylate synthetase inhibitors;
    (e) signal transduction inhibitors;
    (f) cisplatin or platinum analogs;
    (g) monofunctional alkylating agents;
    (h) bifunctional alkylating agents;
    (i) alkylating agents that damage DNA at a different place than does dianhydrogalactitol;
    (j) anti-tubulin agents;
    (k) antimetabolites;
    (l) berberine;

(m) apigenin;
(n) amonafide;
(o) colchicine or analogs;
(p) genistein;
(q) etoposide;
(r) cytarabine;
(s) camptothecins;
(t) vinca alkaloids;
(u) 5-fluorouracil;
(v) curcumin;
(w) NF-κB inhibitors;
(x) rosmarinic acid;
(y) mitoguazone;
(z) tetrandrine;
(aa) temozolomide;
(ab) VEGF inhibitors;
(ac) cancer vaccines;
(ad) EGFR inhibitors;
(ae) tyrosine kinase inhibitors; and
(af) poly (ADP-ribose) polymerase (PARP) inhibitors.

In these alternatives, when the additional therapeutic agent is an alkylating agent, the alkylating agent can be, but is not limited to, an alkylating agent selected from the group consisting of BCNU, BCNU wafers, CCNU, bendamustine (Treanda), and temozolimide (Temodar).

In another alternative, the composition comprises:
(i) a substituted hexitol derivative; and
(ii) a therapeutic agent subject to chemosensitization selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) amonafide;
(m) colchicine or analogs;
(n) genistein;
(o) etoposide;
(p) cytarabine;
(q) camptothecins;
(r) vinca alkaloids;
(s) topoisomerase inhibitors;
(t) 5-fluorouracil;
(u) curcumin;
(v) NF-κB inhibitors;
(w) rosmarinic acid;
(x) mitoguazone;
(y) tetrandrine;
(z) a tyrosine kinase inhibitor;
(aa) an inhibitor of EGFR; and
(ab) an inhibitor of PARP;
wherein the substituted hexitol derivative acts as a chemosensitizer.

In still another alternative, the composition comprises:
(i) a substituted hexitol derivative; and
(ii) a therapeutic agent subject to chemopotentiation selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) amonafide;
(m) colchicine or analogs;
(n) genistein;
(o) etoposide;
(p) cytarabine;
(q) camptothecins;
(r) vinca alkaloids;
(s) 5-fluorouracil;
(t) curcumin;
(u) NF-κB inhibitors;
(v) rosmarinic acid;
(w) mitoguazone;
(x) tetrandrine;
(y) a tyrosine kinase inhibitor;
(z) an inhibitor of EGFR; and
(aa) an inhibitor of PARP;
wherein the substituted hexitol derivative acts as a chemopotentiator.

In these alternatives, wherein the additional therapeutic agent is a biotherapeutic, the biotherapeutic can be, but is not limited to, a biotherapeutic selected from the group consisting of Avastin, Herceptin, Rituxan, and Erbitux.

In yet another alternative, the substituted hexitol derivative is subjected to a bulk drug product improvement, wherein the bulk drug product improvement is selected from the group consisting of:
(a) salt formation;
(b) preparation as a homogeneous crystal structure;
(c) preparation as a pure isomer;
(d) increased purity;
(e) preparation with lower residual solvent content; and
(f) preparation with lower residual heavy metal content.

In still another alternative, the composition comprises a substituted hexitol derivative and a diluent, wherein the diluent is selected from the group consisting of:
(a) an emulsion;
(b) dimethylsulfoxide (DMSO);
(c) N-methylformamide (NMF)
(d) DMF;
(e) ethanol;
(f) benzyl alcohol;
(g) dextrose-containing water for injection;
(h) Cremophor;
(i) cyclodextrin; and
(j) PEG.

In still another alternative, the composition comprises a substituted hexitol derivative and a solvent system, wherein the solvent system is selected from the group consisting of:
(a) an emulsion;
(b) dimethylsulfoxide (DMSO);
(c) N-methylformamide (NMF)
(d) DMF;
(e) ethanol;
(f) benzyl alcohol;
(g) dextrose-containing water for injection;
(h) Cremophor;
(i) cyclodextrin; and
(j) PEG.

In yet another alternative, the composition comprises a substituted hexitol derivative and an excipient, wherein the excipient is selected from the group consisting of:
(a) mannitol;
(b) albumin;
(c) EDTA;
(d) sodium bisulfite;
(e) benzyl alcohol;
(f) a carbonate buffer; and
(g) a phosphate buffer.

In still another alternative, the substituted hexitol derivative is incorporated into a dosage form selected from the group consisting of:
(a) tablets;
(b) capsules;
(c) topical gels;
(d) topical creams;
(e) patches;
(f) suppositories; and
(g) lyophilized dosage fills.

In yet another alternative, the dianhydrogalactitol is incorporated into a dosage kit and packaging selected from the group consisting of amber vials to protect from light and stoppers with specialized coatings to improve shelf-life stability.

In still another alternative, the composition comprises dianhydrogalactitol and a drug delivery system selected from the group consisting of:
(a) nanocrystals;
(b) bioerodible polymers;
(c) liposomes;
(d) slow release injectable gels; and
(e) microspheres.

In still another alternative, the substituted hexitol derivative is present in the composition in a drug conjugate form selected from the group consisting of:
(a) a polymer system;
(b) polylactides;
(c) polyglycolides;
(d) amino acids;
(e) peptides; and
(f) multivalent linkers.

In yet another alternative, the therapeutic agent is a modified substituted hexitol derivative and the modification is selected from the group consisting of:
(a) alteration of side chains to increase or decrease lipophilicity;
(b) addition of an additional chemical functionality to alter a property selected from the group consisting of reactivity, electron affinity, and binding capacity; and
(c) alteration of salt form.

In still another alternative, the substituted hexitol derivative is in the form of a prodrug system, wherein the prodrug system is selected from the group consisting of:
(a) the use of enzyme sensitive esters;
(b) the use of dimers;
(c) the use of Schiff bases;
(d) the use of pyridoxal complexes; and
(e) the use of caffeine complexes.

In yet another alternative, the composition comprises a substituted hexitol derivative and at least one additional therapeutic agent to form a multiple drug system, wherein the at least one additional therapeutic agent is selected from the group consisting of:
(a) an inhibitor of multi-drug resistance;
(b) a specific drug resistance inhibitor;
(c) a specific inhibitor of a selective enzyme;
(d) a signal transduction inhibitor;
(e) an inhibitor of a repair enzyme; and
(f) a topoisomerase inhibitor with non-overlapping side effects.

When a pharmaceutical composition according to the present invention includes a prodrug, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992).

When the pharmacologically active compound in a pharmaceutical composition according to the present invention possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, β-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

The amount of a given pharmacologically active agent, such as a substituted hexitol derivative such as dianhydrogalactitol or an analog or derivative of dianhydrogalactitol as described above, that is included in a unit dose of a pharmaceutical composition according to the present invention will vary depending upon factors such as the particular compound, disease condition and its severity, the identity (e.g., weight) of the subject in need of treatment, but can nevertheless be routinely determined by one skilled in the art. Typically, such pharmaceutical compositions include a therapeutically effective quantity of the pharmacologically active agent and an inert pharmaceutically acceptable carrier or diluent. Typically, these compositions are prepared in unit dosage form appropriate for the chosen route of administration, such as oral administration or parenteral administration. A pharmacologically active agent as described above can be administered in conventional dosage form prepared by combining a therapeutically effective amount of such a pharmacologically active agent as an active ingredient with appropriate pharmaceutical carriers or diluents according to conventional procedures. These procedures may involve mixing, granulating and compressing or dissolving the ingredients as appropriate to the desired preparation. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of a pharmacologically active agent as described above is dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease and/or condition being treated. Actual dosage levels of the active ingredients in the pharmaceutical compositions of the present invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular therapeutic agent, the route of administration, the time of administration, the rate of excretion of the particular compound being employed, the severity of the condition, other health considerations affecting the subject, and the status of liver and kidney function of the subject. It also depends on the duration of the treatment, other drugs, compounds and/or materials used in combination with the particular therapeutic agent employed, as well as the age, weight, condition, general health and prior medical history of the subject being treated, and like factors. Methods for determining optimal dosages are described in the art, e.g., Remington: *The Science and Practice of Pharmacy*, Mack Publishing Co., $20^{th}$ ed., 2000. Optimal dosages for a given set of conditions can be ascertained by those skilled in the art using conventional dosage-determination tests in view of the experimental data for an agent. For oral administration, an exemplary daily dose generally employed is from about 0.001 to about 3000 mg/kg of body weight, with courses of treatment repeated at appropriate intervals. In some embodiments, the daily dose is from about 1 to 3000 mg/kg of body weight.

Typical daily doses in a patient may be anywhere between about 500 mg to about 3000 mg, given once or twice daily, e.g., 3000 mg can be given twice daily for a total dose of 6000 mg. In one embodiment, the dose is between about 1000 to about 3000 mg. In another embodiment, the dose is between about 1500 to about 2800 mg. In other embodiments, the dose is between about 2000 to about 3000 mg. Typically, doses are from about 1 mg/m$^2$ to about 40 mg/m$^2$. Preferably, doses are from about 5 mg/m$^2$ to about 25 mg/m$^2$. Additional alternatives for dosages are as described above with respect to schedules of administration and dose modification. Dosages can be varied according to the therapeutic response.

Plasma concentrations in the subjects may be between about 100 µM to about 1000 µM. In some embodiments, the plasma concentration may be between about 200 µM to about 800 µM. In other embodiments, the concentration is about 300 µM to about 600 µM. In still other embodiments the plasma concentration may be between about 400 to about 800 µM. In another alternative, the plasma concentration can be between about 0.5 µM to about 20 µM, typically 1 µM to about 10 µM. Administration of prodrugs is typically dosed at weight levels, which are chemically equivalent to the weight levels of the fully active form.

The compositions of the invention may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations, which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, solutions, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Pharmaceutical formulations for parenteral administration can include aqueous solutions or suspensions. Suitable lipophilic solvents or vehicles include fatty oils such as sesame oil or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or modulators which increase the solubility or dispersibility of the composition to allow for the preparation of highly concentrated solutions, or can contain suspending or dispersing agents. Pharmaceutical preparations for oral use can be obtained by combining the pharmacologically active agent with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating modulators may be added, such as the cross-linked polyvinyl pyrrolidone, agar, or alginic acid or a salt thereof such as sodium alginate.

Other ingredients such as stabilizers, for example, antioxidants such as sodium citrate, ascorbyl palmitate, propyl gallate, reducing agents, ascorbic acid, vitamin E, sodium bisulfite, butylated hydroxytoluene, BHA, acetylcysteine, monothioglycerol, phenyl-$\alpha$-naphthylamine, or lecithin can be used. Also, chelators such as EDTA can be used. Other ingredients that are conventional in the area of pharmaceutical compositions and formulations, such as lubricants in tablets or pills, coloring agents, or flavoring agents, can be used. Also, conventional pharmaceutical excipients or carriers can be used. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agents, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, particularly as described above. For administration of any of the compounds used in the present invention, preparations should meet sterility, pyrogenicity, general safety, and purity standards as required by the FDA Office of Biologics Standards or by other regulatory organizations regulating drugs.

For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days; in other alternatives, depending on the therapeutic agent and the formulation employed, release may occur over hours, days, weeks, or months. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

A pharmaceutical composition can be administered by a variety of methods known in the art. The routes and/or modes of administration vary depending upon the desired results. Depending on the route of administration, the pharmacologically active agent may be coated in a material to protect the targeting composition or other therapeutic agent from the action of acids and other compounds that may inactivate the agent. Conventional pharmaceutical practice can be employed to provide suitable formulations or compositions for the administration of such pharmaceutical compositions to subjects. Any appropriate route of administration can be employed, for example, but not limited to, intravenous, parenteral, intraperitoneal, intravenous, transcutaneous, subcutaneous, intramuscular, intraurethral, or oral administration. Depending on the severity of the malignancy or other disease, disorder, or condition to be treated, as well as other conditions affecting the subject to be treated, either systemic or localized delivery of the pharmaceutical composition can be used in the course of treatment. The pharmaceutical composition as described above can be administered together with additional therapeutic agents intended to treat a particular disease or condition, which may be the same disease or condition that the pharmaceutical composition is intended to treat, which may be a related disease or condition, or which even may be an unrelated disease or condition.

Pharmaceutical compositions according to the present invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymers, lactide/glycolide copolymers, or polyoxyethylene-polyoxypropylene copolymers may be used to control the release of the compounds. Other potentially useful parenteral delivery systems for molecules of the invention include ethylene-vinyl acetate copolymer particles, osmotic pumps, and implantable infusion systems. Formulations for inhalation may contain excipients, for example, lactose, or may be aqueous solutions containing, e.g., polyoxyethylene-9-lauryl ether, glycocholate and deoxycholate, or can be oily solutions for administration or gels.

Pharmaceutical compositions according to the present invention are usually administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

For the purposes of the present application, treatment can be monitored by observing one or more of the improving symptoms associated with the disease, disorder, or condition being treated, or by observing one or more of the improving clinical parameters associated with the disease, disorder, or condition being treated. In the case of glioblastoma multiforme, the clinical parameters can include, but are not limited to, reduction in tumor burden, reduction in pain, reduction in edema of the brain, reduction in frequency or severity of seizures, reduction in frequency or severity of vomiting, reduction of frequency or severity of headache, reduction in memory deficit, reduction in neurological deficit, and reduction in occurrence of tumor spread or metastasis. As used herein, the terms "treatment," "treating," or equivalent terminology are not intended to imply a permanent cure for the disease, disorder, or condition being treated. Compositions and methods according to the present invention are not limited to treatment of humans, but are applicable to treatment of socially or economically important animals, such as dogs, cats, horses, cows, sheep, goats, pigs, and other animal species of social or economic importance. Unless specifically stated, compositions and methods according to the present invention are not limited to the treatment of humans.

Sustained-release formulations or controlled-release formulations are well-known in the art. For example, the sustained-release or controlled-release formulation can be (1) an oral matrix sustained-release or controlled-release formulation; (2) an oral multilayered sustained-release or controlled-release tablet formulation; (3) an oral multiparticulate sustained-release or controlled-release formulation; (4) an oral osmotic sustained-release or controlled-release formulation; (5) an oral chewable sustained-release or controlled-release formulation; or (6) a dermal sustained-release or controlled-release patch formulation.

The pharmacokinetic principles of controlled drug delivery are described, for example, in B. M. Silber et al., "Pharmacokinetic/Pharmacodynamic Basis of Controlled Drug Delivery" in *Controlled Drug Delivery: Fundamentals and Applications* (J. R. Robinson & V. H. L. Lee, eds, 2d ed., Marcel Dekker, New York, 1987), ch. 5, pp. 213-251, incorporated herein by this reference.

One of ordinary skill in the art can readily prepare formulations for controlled release or sustained release comprising a pharmacologically active agent according to the present invention by modifying the formulations described above, such as according to principles disclosed in V. H. K. Li et al, "Influence of Drug Properties and Routes of Drug Administration on the Design of Sustained and Controlled Release Systems" in *Controlled Drug Delivery: Fundamentals and Applications* (J. R. Robinson & V. H. L. Lee, eds, 2d ed., Marcel Dekker, New York, 1987), ch. 1, pp. 3-94, incorporated herein by this reference. This process of preparation typically takes into account physicochemical properties of the pharmacologically active agent, such as aqueous solubility, partition coefficient, molecular size, stability, and nonspecific binding to proteins and other biological macromolecules. This process of preparation also takes into account biological factors, such as absorption, distribution, metabolism, duration of action, the possible existence of side effects, and margin of safety, for the pharmacologically active agent. Accordingly, one of ordinary skill in the art could modify the formulations into a formulation having the desirable properties described above for a particular application.

U.S. Pat. No. 6,573,292 by Nardella, U.S. Pat. No. 6,921,722 by Nardella, U.S. Pat. No. 7,314,886 to Chao et al., and U.S. Pat. No. 7,446,122 by Chao et al., which disclose methods of use of various pharmacologically active agents and pharmaceutical compositions in treating a number of diseases and conditions, including cancer, and methods of determining the therapeutic effectiveness of such pharmacologically active agents and pharmaceutical compositions, are all incorporated herein by this reference.

In view of the results reported in the Example below, another aspect of the present invention is a method of treating glioblastoma multiforme comprising the step of administering a therapeutically effective quantity of a substituted hexitol derivative such as dianhydrogalactitol to a patient suffering from the malignancy.

Typically, when the substituted hexitol derivative is dianhydrogalactitol, the therapeutically effective quantity of dianhydrogalactitol is from about 1 mg/m$^2$ to about 40 mg/m$^2$. Preferably, the therapeutically effective quantity of dianhydrogalactitol is from about 5 mg/m$^2$ to about 25 mg/m$^2$. Therapeutically active quantities of substituted hexitol derivatives other than dianhydrogalactitol can be determined by one of ordinary skill in the art by using the molecular weight of the particular substituted hexitol derivative and the activity of the particular substituted hexitol derivative, such as the in vitro activity of the substituted hexitol derivative against a standard cell line. Other suitable dosages are described in the Examples.

Typically, the substituted hexitol derivative such as dianhydrogalactitol is administered by a route selected from the group consisting of intravenous and oral. Preferably, the substituted hexitol derivative such as dianhydrogalactitol is administered intravenously.

The method can further comprise the step of administering a therapeutically effective dose of ionizing radiation. The method can further comprise the step of administering a therapeutically effective quantity of temozolomide, bevacizumab, or a corticosteroid. In another alternative, the method can further comprise the step of administering a therapeutically effective quantity of at least one chemotherapeutic agent selected from the group consisting of lomustine, cisplatin, carboplatin, vincristine, and cyclophosphamide. Suitable methods for administration of these agents and suitable dosages are well known in the art.

Typically, the substituted hexitol derivative such as dianhydrogalactitol substantially suppresses the growth of cancer stem cells (CSCs). Typically, the suppression of the growth of cancer stem cells is at least 50%. Preferably, the suppression of the growth of cancer stem cells is at least 99%.

Typically, the substituted hexitol derivative such as dianhydrogalactitol is effective in suppressing the growth of cancer cells possessing O$^6$-methylguanine-DNA methyltransferase (MGMT)-driven drug resistance. Typically, the substituted hexitol derivative such as dianhydrogalactitol is also effective in suppressing the growth of cancer cells resistant to temozolomide.

The method can further comprise the administration of a therapeutically effective quantity of a tyrosine kinase inhibitor as described above.

The method can further comprise the administration of a therapeutically effective quantity of an epidermal growth factor receptor (EGFR) inhibitor as described above. The EGFR inhibitor can affect either wild-type binding sites or mutated binding sites, including EGFR Variant III, as described above.

The invention is illustrated by the following Examples. These Examples are included for illustrative purposes only, and are not intended to limit the invention.

Example 1

Use of Dianhydrogalactitol to Inhibit Growth of Glioblastoma Multiforme and Medulloblastoma Cells Materials and Methods:
Cell Lines and Culture Conditions:

All cells were cultured in DMEM (Dulbecco's Modified Eagle's medium; Invitrogen/Gibco) with 10% FBS (fetal bovine serum; Invitrogen/Gibco) at 37° C. with 5% $CO_2$, and subcultured twice weekly during the experimental period.

Drugs:

Temozolomide (TMZ) was purchased from Sigma Aldrich and dissolved in dimethyl sulfoxide (DMSO) (Sigma-Aldrich). A stock solution of 100 mM was kept at −20° C. before use. Dianhydrogalactitol (DAG; results with DAG are shown as "VAL" in the figures) was provided by Del Mar Pharmaceuticals Ltd. A stock solution of 100 mM was prepared by dissolving the lyophilized powder in the injection vial in sterile phosphate buffered saline (PBS) and kept at 20° C. before use.

Growth Assays:

Each cell line used was seeded at 3000 cells/well in 100 μL medium in a 96-well plate (BD Falcon) and incubated overnight. Cells were then treated with TMZ or DAG at concentrations of 0.1-100 μM in fresh medium for 72 hours. The cells were fixed in 2% paraformaldehyde (Sigma-Aldrich) with nuclear dye Hoechst 33342 (1 μg/mL) (Sigma-Aldrich). After gentle washing with PBS, the cells were kept in fresh PBS and the plates were kept at 4° C. in the dark before HCS (high content screening (ThermoFisher Scientific) analysis. Twenty view fields per well were scanned and analyzed. Growth inhibition was calculated as a percentage of the control without the solvent and the drug; the samples treated with solvent alone served as a reference. There were three replicates for each treatment and the experiments were repeated once.

Results

FIG. 1 is a chart showing three GBM cell lines used and showing their degree of temozolomide (TMZ) resistance and the status of methylation of the promoter of the $O^6$-methylguanine-DNA methyltransferase (MGMT) gene. In general, an increase of methylation of the MGMT promoter is associated with improved outcome in GBM.

FIG. 2A is a graph showing the inhibition of growth of the GBM cell line SF188 with increasing concentrations of TMZ and dianhydrogalactitol (DAG; shown as "VAL" in the figures) (two experiments each). In FIG. 2A, (♦) represents TMZ results and (■) represents DAG results. FIG. 2A clearly shows that dianhydrogalactitol is a more efficient inhibitor of growth of the GBM cell line SF188 than TMZ.

FIG. 2B is a graph showing the inhibition of growth of the GBM cell line U251 with increasing concentrations of TMZ and DAG (two experiments each). In FIG. 2B, (♦) represents TMZ results and (■) represents DAG results. FIG. 2B clearly shows that dianhydrogalactitol is a more efficient inhibitor of growth of the GBM cell line U251 than TMZ.

FIG. 2C is a graph showing the inhibition of growth of the GBM cell line T98G with increasing concentrations of TMZ and DAG (two experiments each). In FIG. 2C, (♦) represents TMZ results and (■) represents DAG results. FIG. 2C clearly shows that dianhydrogalactitol is a more efficient inhibitor of growth of the GBM cell line T98G than TMZ.

FIG. 3 is a chart showing the three cell lines used in FIGS. 2A, 2B, and 2C, indicating TMZ resistance and MGMT status.

Figure 4:
FIG. 4 is a photograph showing that DAG at 5 μM inhibits colony formation by the GBM cell line SF188 by more than 95% after 7 days.

FIG. 4 is a photograph showing that DAG at 5 μM inhibits colony formation by the GBM cell line SF188 by more than 95% after 7 days.

Figure 5:
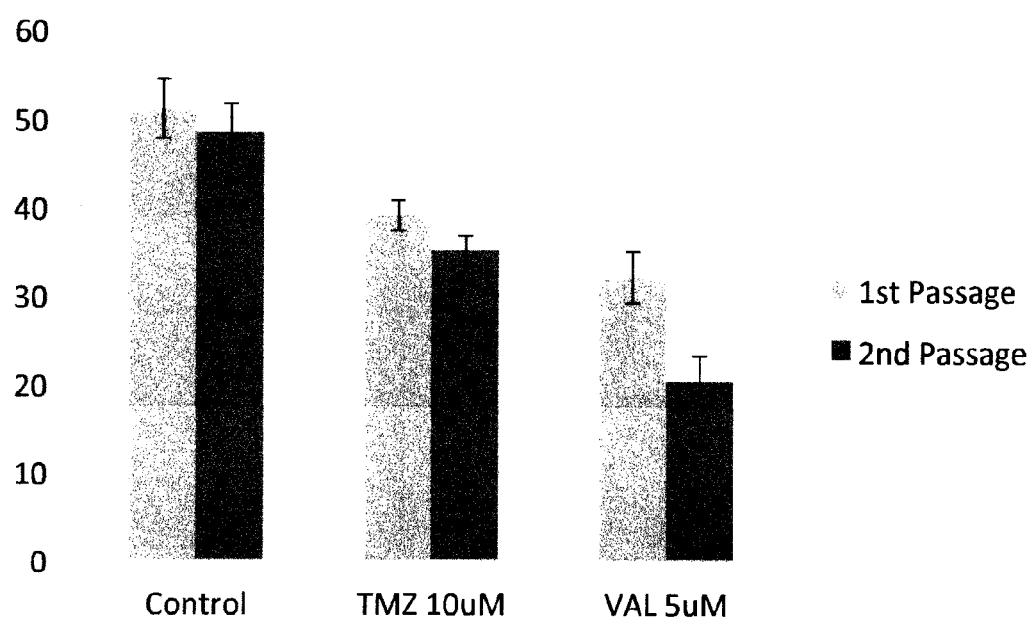
FIG. 5 is a graph showing that DAG inhibits the growth of SF188 cells more effectively than TMZ, particularly in secondary sphere formation.

FIG. 5 is a graph showing that DAG inhibits the growth of SF188 cells more effectively than TMZ, particularly in secondary sphere formation. BT74 cells are notably TMZ resistant; therefore, the activity of DAG in this setting illustrates activity in otherwise insensitive cells.

Figure 6:
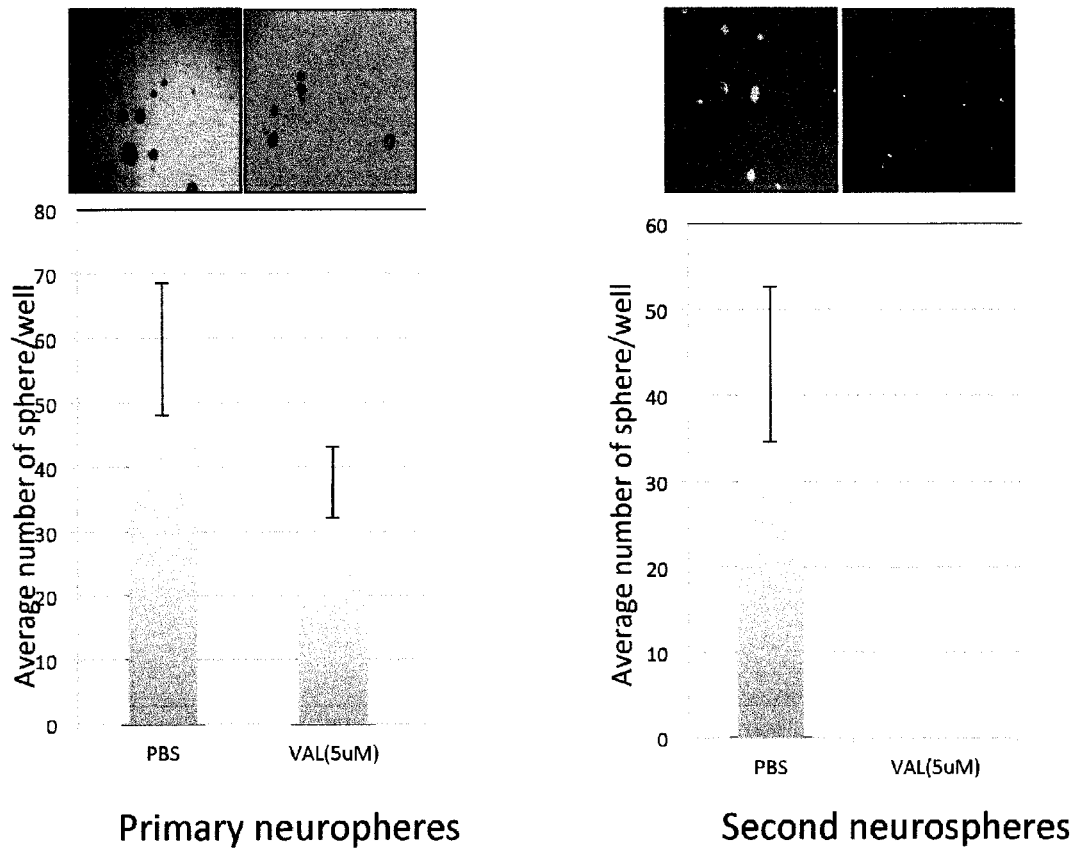
FIG. 6 shows that DAG completely inhibits secondary neurosphere formation by BT74 cancer stem cells and substantially inhibits primary neurosphere formation; photomicrographs are shown at the top, and graphs showing the extent of inhibition are shown under the photomicrographs.

FIG. 6 shows that DAG completely inhibits secondary neurosphere formation by BT74 cancer stem cells and substantially inhibits primary neurosphere formation; photomicrographs are shown at the top, and graphs showing the extent of inhibition are shown under the photomicrographs.

Figure 7:
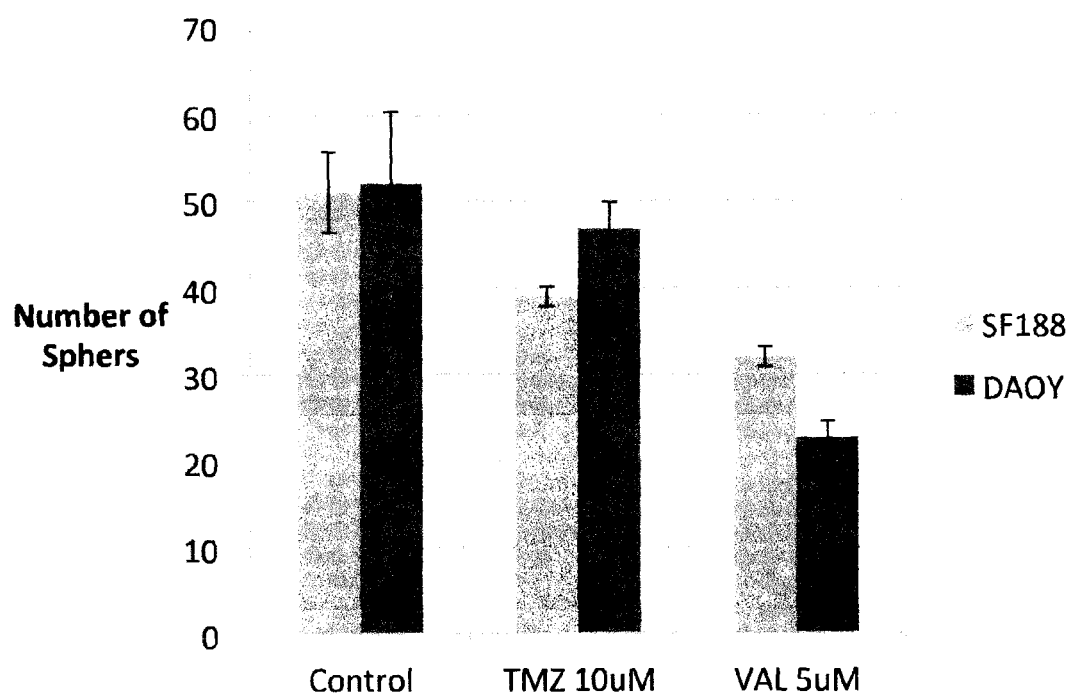
FIG. 7 is a graph showing that DAG is more efficient at inhibiting primary neurosphere formation than TMZ for SF188 and DAOY cell lines. DAOY is a medulloblastoma cell line.

FIG. 7 is a graph showing that DAG is more efficient at inhibiting primary neurosphere formation than TMZ for SF188 and DAOY cell lines. DAOY is a medulloblastoma cell line.

Figure 8:
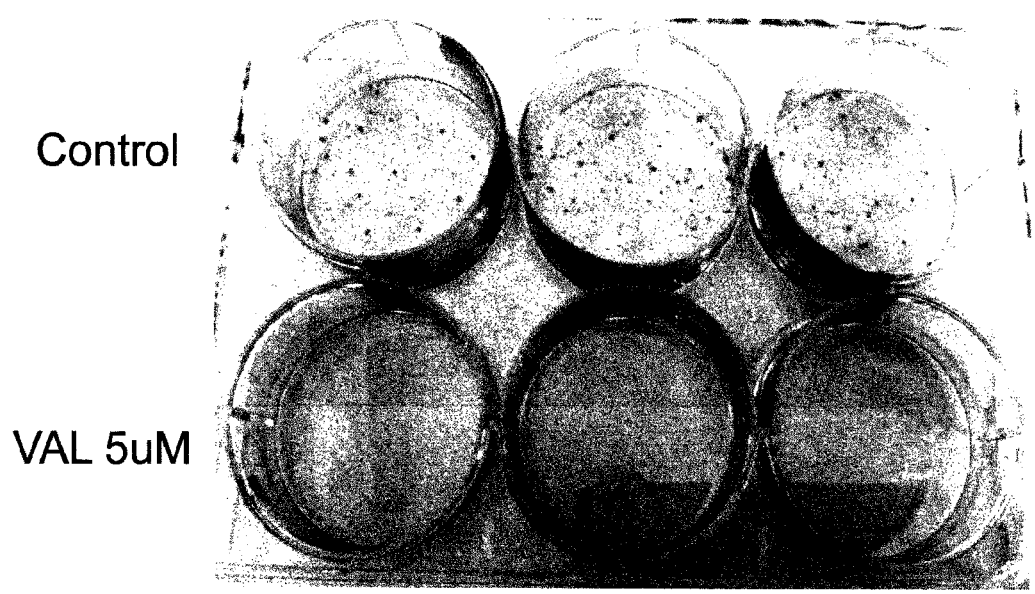
FIG. 8 is a photograph showing that DAG at 5 μM completely inhibits colony formation by the medulloblastoma cell line DAOY after 7 days.

FIG. 8 is a photograph showing that DAG at 5 μM completely inhibits colony formation by the medulloblastoma cell line DAOY after 7 days.

Figure 9:
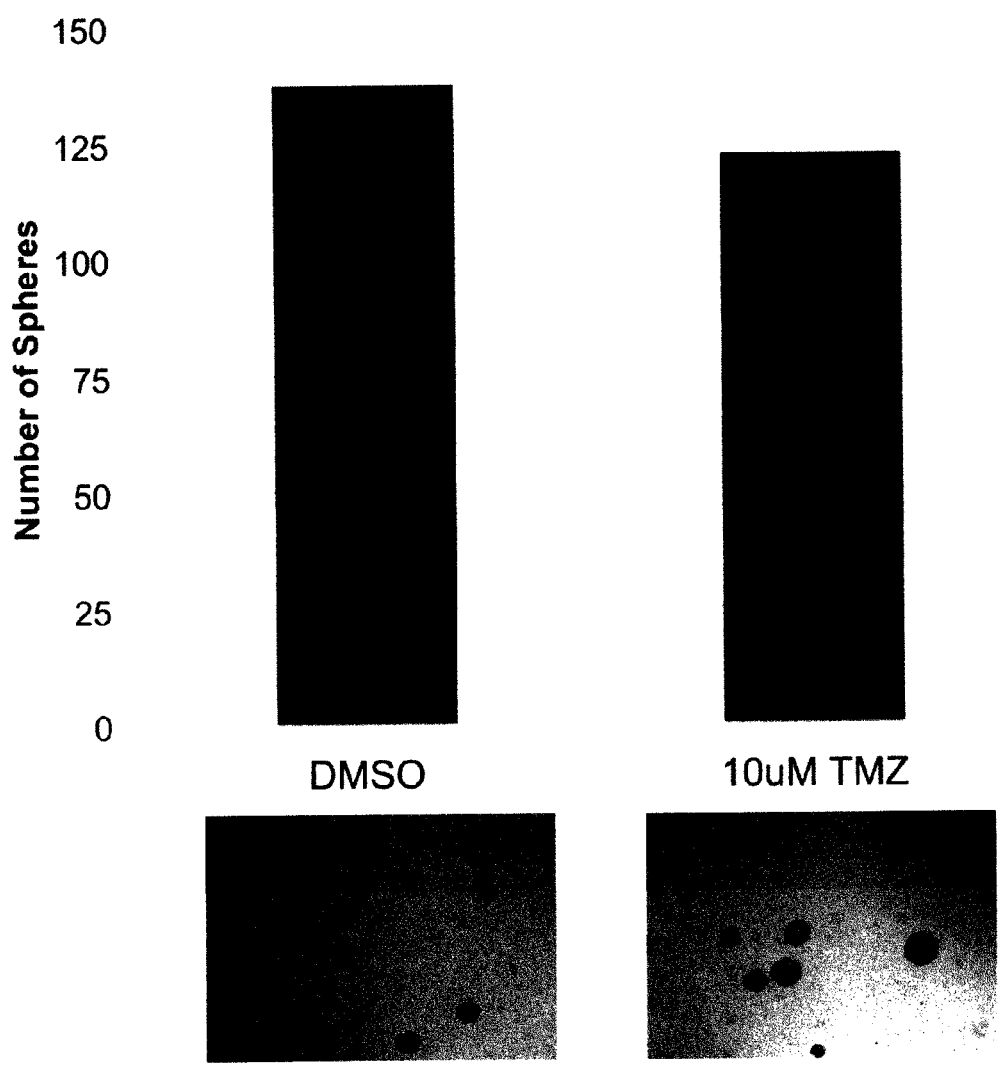
FIG. 9 is a graph and comparative photomicrographs showing that BT74 cells do not show significant sensitivity to TMZ.

FIG. 9 is a graph and comparative photomicrographs showing that BT74 cells do not show significant sensitivity to TMZ.

Figure 10:
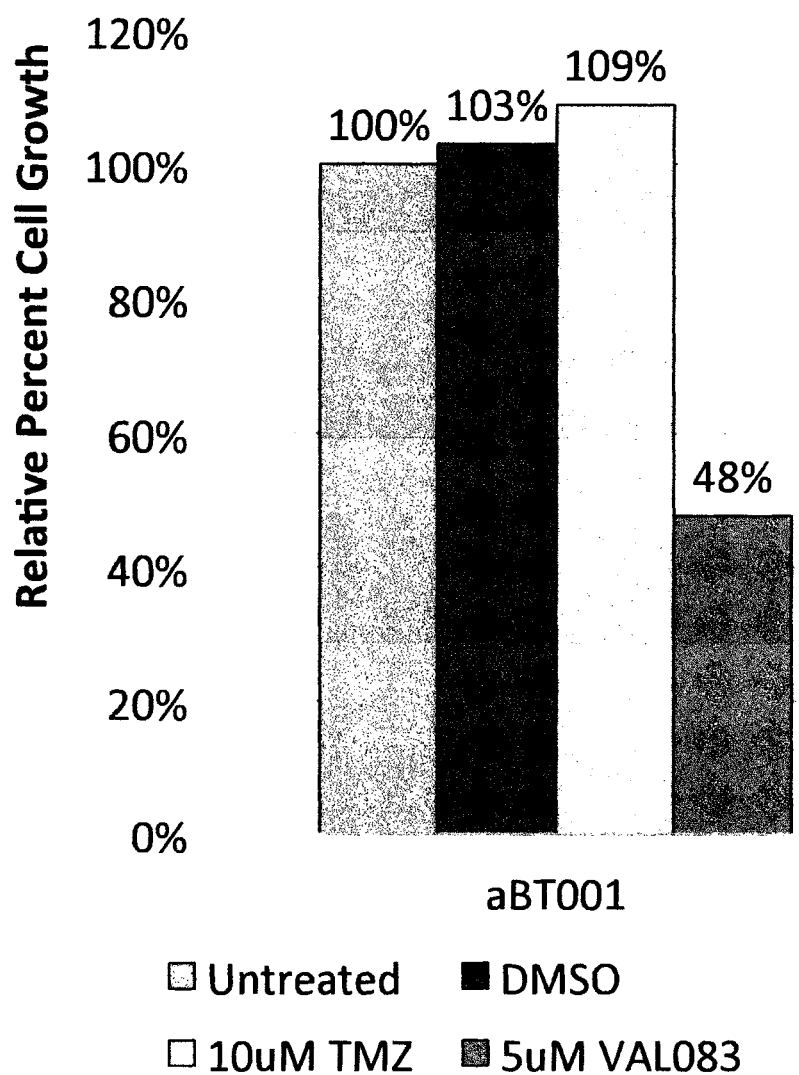
FIG. 10 is a graph showing the effect of DAG on primary adult GBM cells isolated fresh from BCCH, showing a substantial degree of inhibition; TMZ essentially has no effect on these cells.

FIG. 10 is a graph showing the effect of DAG on primary adult GBM cells isolated fresh from BCCH, showing a substantial degree of inhibition; TMZ essentially has no effect on these cells.

Figure 11:
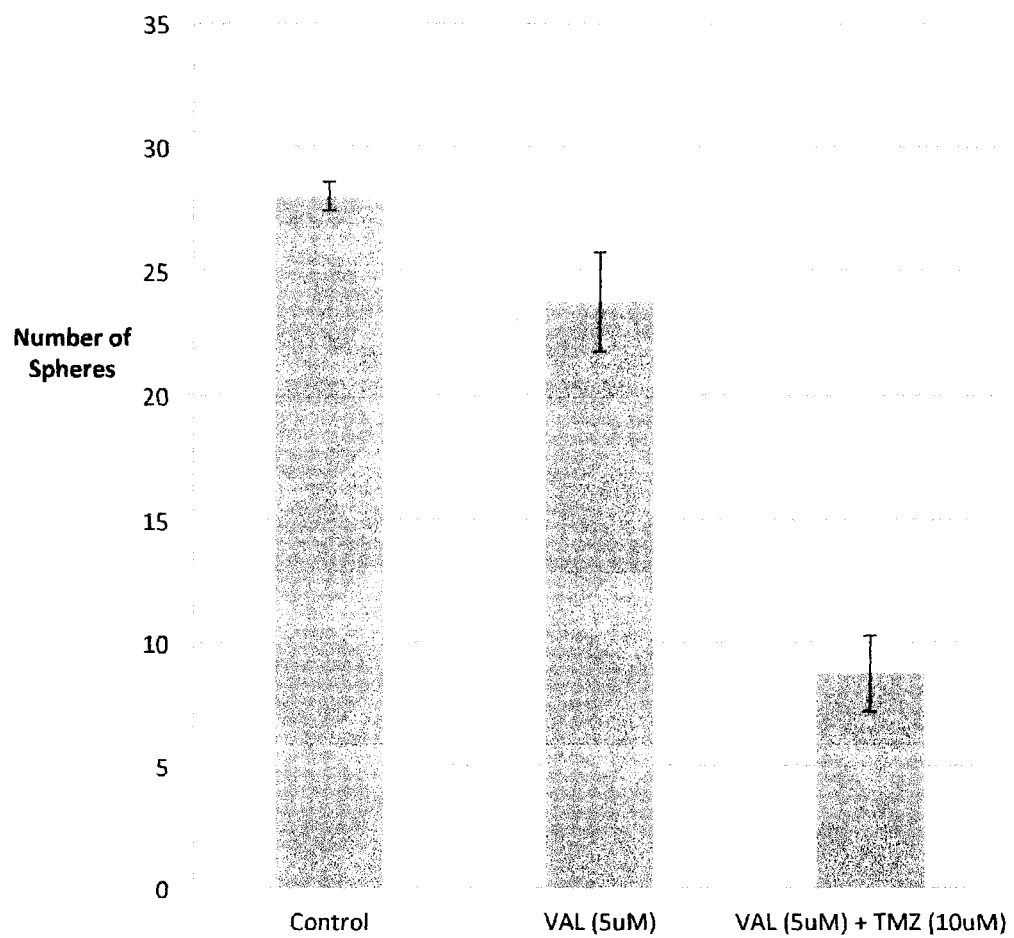
FIG. 11 is a set of graphs showing effect of combination treatments with TMZ and DAG on SF188 cells, showing inhibition of neurosphere formation; the combination of TMZ plus DAG provided the greatest degree of inhibition.

FIG. 11 is a set of graphs showing effect of combination treatments with TMZ and DAG on SF188 cells, showing inhibition of neurosphere formation; the combination of TMZ plus DAG provided the greatest degree of inhibition.

Figure 12:
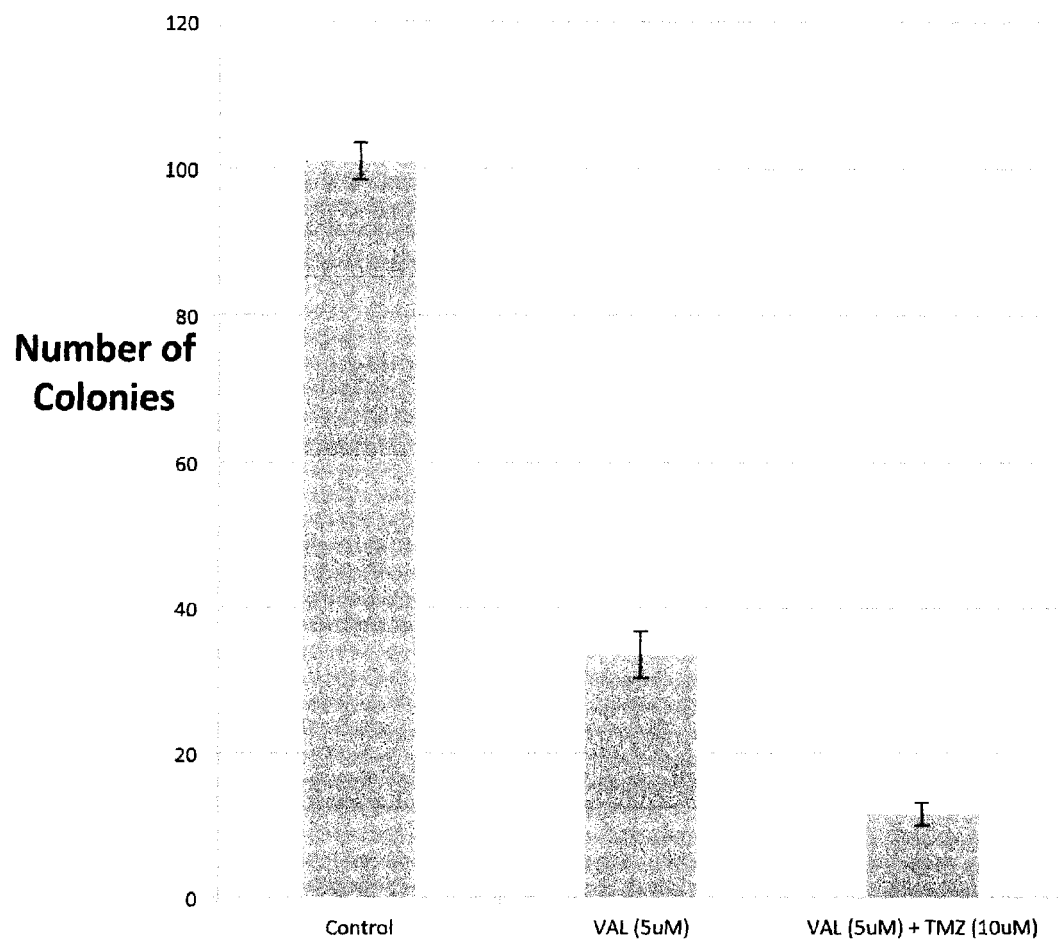
FIG. 12 is a set of graphs showing effect of combination treatments with TMZ and DAG on SF188 cells, showing inhibition of colony formation; the combination of TMZ plus DAG provided the greatest degree of inhibition.

FIG. 12 is a set of graphs showing effect of combination treatments with TMZ and DAG on SF188 cells, showing inhibition of colony formation; the combination of TMZ plus DAG provided the greatest degree of inhibition.

Conclusions:

Glioblastoma (GBM) remains one of the most difficult tumors to treat in part because many new agents fail to cross the blood brain barrier (BBB) and secondly due to intrinsic drug resistance. Temozolomide (TMZ) is a front-line therapy for the treatment of GBM, however, it is often ineffective due to drug inactivation by $O^6$-methylguanine-DNA methyltransferase (MGMT). Cancer stem cells (CSC) are a subpopulation of the tumor that resist therapy and give rise to relapse. Here we described dianhydrogalactitol (DAG), a novel alkylating agent that creates $N^7$ methylation on DNA, which was initially intriguing because it crosses the BBB. We addressed how it compared to TMZ, whether it could be used to overcome MGMT-driven drug resistance and if has activity against CSCs. Addressing these questions provides further preclinical support for DAG, which is currently undergoing human clinical trials in the USA against refractory GBM.

DAG inhibited U251 and SF188 cell growth in monolayer and as neurospheres more effectively than TMZ and caused apoptosis after 72 hrs. In a 10-day colony formation assay, DAG (5 μM) suppressed SF188 growth by ~95%. T98G cells are classically TMZ resistant and express MGMT yet DAG inhibited their growth in monolayer after 72 hrs in a dose-dependent manner (IC50=5 μM). DAG also significantly inhibited the growth of primary glioblastoma multiforme cells that were completely resistant to TMZ. DAG also inhibited the growth of CSCs by 100% in neurosphere growth assays. In summary, DAG has better in vitro efficacy than TMZ against brain tumor cells, can overcome resistance associated with MGMT, and targets brain tumor CSCs, demonstrating that it has the potential to surpass the current standard of care. DAG is also extremely effective in combination with TMZ, showing efficient inhibition of neurosphere formation and secondary colony formation in combination with that drug.

In conclusion, dianhydrogalactitol shows substantially more activity in inhibiting the growth of glioblastoma multiforme cell lines than does the conventionally accepted gold standard for glioblastoma multiforme chemotherapy, temozolomide. Dianhydrogalactitol also suppresses colony formation and proliferation by cancer stem cells. Dianhydrogalactitol also is an effective growth inhibitor of a medulloblastoma cell line.

The data of this Example demonstrates that dianhydrogalactitol is active against tumors that are refractory to temozolomide. The data of this Example also demonstrates that dianhydrogalactitol acts independently of the $O^6$-methylguanine-DNA methyltransferase (MGMT) repair mechanism. The activity of dianhydrogalactitol was also demonstrated in medulloblastoma and in childhood, as well as adult, glioblastoma multiforme. Importantly, dianhydrogalactitol has demonstrated activity against cancer stem cells, as demonstrated by the neurosphere data. Additionally dianhydrogalactitol can be combined with TMZ for improved therapeutic efficiency.

The results of this Example show that dianhydrogalactitol has substantial activity against both glioblastoma multiforme and medulloblastoma cell lines under conditions in which the activity would appear to correlate well with in vivo effectiveness of a chemotherapeutic agent in treating these malignancies.

Example 2

Study of Dianhydrogalactitol in Patients with Recurrent Glioblastoma Multiforme

Median survival for patients with recurrent glioblastoma multiforme (GBM) is less than 6 months. Front-line systemic therapy is temozolomide (TMZ), but chemo-resistance due to $O^6$-methylguanine-DNA-methyltransferase (MGMT) activity has been implicated in poor outcomes. Dianhydrogalactitol is a structurally unique bifunctional DNA alkylating small molecule drug that crosses the blood-brain barrier and accumulates in brain tumor tissue. In preclinical in vitro studies, dianhydrogalactitol demonstrated activity in a wide range of cancer cell lines, including pediatric and adult GBM cell lines and GBM stem cells. Notably, dianhydrogalactitol overcomes chemo-resistance induced by MGMT in vitro. A new clinical study has been initiated with the primary objective of establishing the maximum tolerated dose (MTD) and identifying a dose and dosing regimen for further study. Dose-limiting toxicity is expected to be myelosuppression, the management of which has improved in recent years. Initially, a cumulative dose of 150 mg/m² repeated each month was recommended as a safe and effective starting dose (R. T. Eagan et al., "Phase I Study of a Five-Day Intermittent Schedule for 1,2:5,6-Dianhydrogalactitol (NSC-132313)," *J. Natl. Cancer Inst.* 56: 179-181 (1976); C. D. Haas et al., "Phase I Evaluation of Dianhydrogalactitol (NSC-132313)," *Cancer Treat. Rep.* 60: 611-614 (1976), both of which are incorporated herein by this reference) and a cumulative dose of 125 mg/m² delivered in a 33-day cycle in combination with radiation was demonstrated to be superior to radiation alone (R. T. Eagan et al., "Dianhydrogalactitol and Radiation Therapy. Treatment of Supratentorial Glioma," *J. Am. Med. Assoc.* 241: 2046-2050 (1979), incorporated herein by this reference). In the study reported in this Example, the cumulative dose in a 33-day cycle ranges from 9 mg/m² (cohort 1) to 240 mg/m² (cohort 7). Five dose cohorts, with the highest cumulative dose in a 33-day cycle of 120 mg/m², have completed the trial successfully with no drug-related serious adverse events (SAEs) and a maximum tolerated dose (MTD) had not been reached. The methods of the study reported in this Example were as follows: The study was an open-label, single-arm Phase I/II dose-escalation study in patients with histologically-confirmed initial diagnosis of malignant GBM. The study utilized a 3+3 dose-escalation design. Patients received dianhydrogalactitol on days 1, 2, and 3 of a 21-day cycle. The GBM patients have previously been treated with surgery and/or radiation, if appropriate, and must have failed both temozolomide and bevacizumab, unless contraindicated.

Pharmacokinetic analyses show dose-dependent increase in exposure with a short 1-2 hour plasma half-life and a $C_{max}$ of <200 ng/ml at 10 mg/m². Historical data suggests a long life in the CSF (>20 hours) with preferential accumulation to brain tumor tissue.

Advantages of the Invention

The present invention provides improved methods and compositions employing dianhydrogalactitol for the treatment of glioblastoma multiforme, a type of malignant brain tumor that has proven resistant to chemotherapy by conventional means.

The use of dianhydrogalactitol to treat glioblastoma multiforme is expected to be well tolerated and not to result in additional side effects, an important consideration when many of the treatment modalities currently in use for this brain malignancy result in cognitive and physical impairments. Dianhydrogalactitol can be used together with radiation or other chemotherapeutic agents.

Methods according to the present invention possess industrial applicability for the preparation of a medicament for the treatment of glioblastoma multiforme. Compositions according to the present invention possess industrial applicability as pharmaceutical compositions.

The method claims of the present invention provide specific method steps that are more than general applications of laws of nature and require that those practicing the method steps employ steps other than those conventionally known in the art, in addition to the specific applications of laws of nature recited or implied in the claims, and thus confine the scope of the claims to the specific applications recited therein. In some contexts, these claims are directed to new ways of using an existing drug.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. A method to improve the efficacy and/or reduce the side effects of the administration of a substituted hexitol derivative selected from the group consisting of dianhydrogalactitol, diacetyldianhydrogalactitol, dibromodulcitol, a conjugate of dianhydrogalactitol, a conjugate of diacetyldianhydrogalactitol, a conjugate of dibromodulcitol, a prodrug of dianhydrogalactitol, a prodrug of diacetyldianhydrogalactitol, and a prodrug of dibromodulcitol for treatment of glioblastoma multiforme (GBM) comprising the steps of:
   (a) identifying at least one factor or parameter associated with the efficacy and/or occurrence of side effects of the administration of the substituted hexitol derivative for treatment of GBM; and
   (b) modifying the factor or parameter to improve the efficacy and/or reduce the side effects of the administration of the substituted hexitol derivative for treatment of GBM.

2. The method of claim 1 wherein the substituted hexitol derivative is dianhydrogalactitol.

3. The method of claim 1 wherein the factor or parameter is selected from the group consisting of:
   (a) dose modification;
   (b) route of administration;
   (c) schedule of administration;
   (d) administration to promote preferential accumulation in brain tissue;
   (e) selection of disease stage;
   (f) patient selection;
   (g) patient/disease phenotype;
   (h) patient/disease genotype;
   (i) pre/post-treatment preparation
   (j) toxicity management;
   (k) pharmacokinetic/pharmacodynamic monitoring;
   (l) drug combinations;
   (m) chemosensitization;
   (n) chemopotentiation;
   (o) post-treatment patient management;
   (p) alternative medicine/therapeutic support;
   (q) bulk drug product improvements;
   (r) diluent systems;
   (s) solvent systems;
   (t) excipients;
   (u) dosage forms;
   (v) dosage kits and packaging;
   (w) drug delivery systems;
   (x) drug conjugate forms;
   (y) compound analogs;
   (z) prodrugs;
   (aa) multiple drug systems;
   (ab) biotherapeutic enhancement;
   (ac) biotherapeutic resistance modulation;
   (ad) radiation therapy enhancement;
   (ae) novel mechanisms of action;
   (af) selective target cell population therapeutics;
   (ag) use with ionizing radiation;
   (ah) use with an agent that counteracts myelosuppression; and
   (aj) use with an agent that increases the ability of the substituted hexitol to pass through the blood-brain barrier.

4. The method of claim 3 wherein the substituted hexitol derivative is dianhydrogalactitol.

5. The method of claim 3 wherein the improvement is made by dose modification and the dose modification is at least one dose modification selected from the group consisting of:
   (i) continuous i.v. infusion for hours to days;
   (ii) biweekly administration;
   (iii) doses greater than 5 mg/m$^2$/day;
   (iv) progressive escalation of dosing from 1 mg/m$^2$/day based on patient tolerance;
   (v) use of caffeine to modulate metabolism;
   (vi) use of isoniazid to modulate metabolism;
   (vii) selected and intermittent boosting of dosage administration;
   (viii) administration of single and multiple doses escalating from 5 mg/m$^2$/day via bolus;
   (ix) oral dosages of below 30 mg/m$^2$;
   (x) oral dosages of above 130 mg/m$^2$;
   (xi) oral dosages up to 40 mg/m$^2$ for 3 days and then a nadir/recovery period of 18-21 days;
   (xii) dosing at a lower level for an extended period;
   (xiii) dosing at a higher level;
   (xiv) dosing with a nadir/recovery period longer than 21 days;
   (xv) dosing at a level to achieve a concentration of the substituted hexitol derivative in the cerebrospinal fluid (CSF) of equal to or greater than 5 μM;
   (xvi) dosing at a level to achieve a cytotoxic concentration in the CSF;
   (xvii) the use of the substituted hexitol derivative as a single cytotoxic agent;
   (xviii) administration on a 33-day cycle with a cumulative dose of about 9 mg/m$^2$;
   (xix) administration on a 33-day cycle with a cumulative dose of about 10 mg/m$^2$;
   (xx) administration on a 33-day cycle with a cumulative dose of about 20 mg/m$^2$;
   (xxi) administration on a 33-day cycle with a cumulative dose of about 40 mg/m$^2$;
   (xxii) administration on a 33-day cycle with a cumulative dose of about 80 mg/m$^2$;
   (xxiii) administration on a 33-day cycle with a cumulative dose of about 160 mg/m$^2$;

(xxiv) administration on a 33-day cycle with a cumulative dose of about 240 mg/m²;
(xxv) administration so that the plasma half-life is about 1-2 hours;
(xxvi) administration so that the $C_{max}$ is <200 ng/ml; and
(xxvii) administration so that the substituted hexitol derivative has a half-life of >20 hours in the cerebrospinal fluid.

6. The method of claim 3 wherein the improvement is made by route of administration and the route of administration is at least one route of administration selected from the group consisting of:
   (i) topical administration;
   (ii) oral administration;
   (iii) slow release oral delivery;
   (iv) intrathecal administration;
   (v) intraarterial administration;
   (vi) continuous infusion;
   (vii) intermittent infusion;
   (viii) intravenous administration;
   (ix) administration through a longer infusion;
   (x) administration through IV push; and
   (xi) administration to maximize the concentration of the substituted hexitol derivative in the CSF.

7. The method of claim 6 wherein the route of administration is intravenous administration and the intravenous administration is intravenous administration for 30 minutes.

8. The method of claim 3 wherein the improvement is made by schedule of administration and the schedule of administration is at least one schedule of administration selected from the group consisting of:
   (i) daily administration;
   (ii) weekly administration;
   (iii) weekly administration for three weeks;
   (iv) biweekly administration;
   (v) biweekly administration for three weeks with a 1-2 week rest period;
   (vi) intermittent boost dose administration;
   (vii) daily administration for one week for multiple weeks; and
   (viii) administration on days 1, 2, and 3 of a 33-day cycle.

9. The method of claim 3 wherein the improvement is made by selection of disease stage and wherein the selection of disease stage is at least one selection of disease stage selected from the group consisting of:
   (i) use in an appropriate disease stage for GBM;
   (ii) use with an angiogenesis inhibitor to prevent or limit metastatic spread;
   (iii) use for newly diagnosed GBM;
   (iv) use for recurrent GBM
   (v) use for resistant or refractory GBM; and
   (vi) use for childhood GBM.

10. The method of claim 3 wherein the improvement is made by patient selection and wherein the patient selection is at least one patient selection carried out by a criterion selected from the group consisting of:
    (i) selecting patients with a disease condition characterized by a high level of a metabolic enzyme selected from the group consisting of histone deacetylase and ornithine decarboxylase;
    (ii) selecting patients with a low or high susceptibility to a condition selected from the group consisting of thrombocytopenia and neutropenia;
    (iii) selecting patients intolerant of GI toxicities;
    (iv) selecting patients characterized by over- or under-expression of a gene selected from the group consisting of c-Jun, a GPCR, a signal transduction protein, VEGF, a prostate-specific gene, and a protein kinase;
    (v) selecting patients characterized by carrying extra copies of the EGFR gene for GBM;
    (vi) selecting patients characterized by mutations in at least one gene selected from the group consisting of TP53, PDGFRA, IDH1, and NF1 for GBM;
    (vii) selecting patients characterized by methylation or lack of methylation of the promoter of the MGMT gene;
    (viii) selecting patients characterized by the existence of an IDH1 mutation;
    (ix) selecting patients characterized by the presence of IDH1 wild-type gene;
    (x) selecting patients characterized by the presence of 1p/19q co-deletion;
    (xi) selecting patients characterized by the absence of an 1p/19q co-deletion;
    (xii) selecting patients characterized by an unmethylated promoter region of MGMT ($O^6$-methylguanine methyltransferase);
    (xiii) selecting patients characterized by a methylated promoter region of MGMT;
    (xiv) selecting patients characterized by a high expression of MGMT;
    (xv) selecting patients characterized by a low expression of MGMT; and
    (xvi) selecting patients characterized by a mutation in EGFR.

11. The method of claim 10 wherein the patient selection is selecting patients characterized by a mutation in EGFR and the mutation in EGFR is EGFR Variant III.

12. The method of claim 3 wherein the improvement is made by analysis of patient or disease phenotype and wherein the analysis of patient or disease phenotype is a method of analysis of patient or disease phenotype carried out by a method selected from the group consisting of:
    (i) use of a diagnostic tool, a diagnostic technique, a diagnostic kit, or a diagnostic assay to confirm a patient's particular phenotype;
    (ii) use of a method for measurement of a marker selected from the group consisting of histone deacetylase, ornithine decarboxylase, VEGF, a protein that is a gene product of jun, and a protein kinase;
    (iii) surrogate compound dosing; and
    (iv) low dose pre-testing for enzymatic status.

13. The method of claim 3 wherein the improvement is made by analysis of patient or disease genotype and the analysis of patient or disease genotype is a method of analysis of patient or disease genotype carried out by a method selected from the group consisting of:
    (i) use of a diagnostic tool, a diagnostic technique, a diagnostic kit, or a diagnostic assay to confirm a patient's particular genotype;
    (ii) use of a gene chip;
    (iii) use of gene expression analysis;
    (iv) use of single nucleotide polymorphism (SNP) analysis;
    (v) measurement of the level of a metabolite or a metabolic enzyme;
    (vi) determination of mutation of PDGFRA gene;
    (vii) determination of mutation of IDH1 gene;
    (viii) determination of mutation of NF1 gene;
    (ix) determination of copy number of the EGFR gene;
    (x) determination of status of methylation of promoter of MGMT gene;
    (xi) determination of the existence of an IDH1 mutation;

(xii) determination of the existence of IDH1 wild-type;
(xiii) determination of the existence of a 1p/19q co-deletion;
(xiv) determination of the absence of a 1p/19q co-deletion;
(xv) determination of the existence of an unmethylated promoter region of the MGMT gene;
(xvi) determination of the existence of a methylated promoter region of the MGMT gene;
(xvii) determination of the existence of high expression of MGMT; and
(xviii) determination of the existence of low expression of MGMT.

14. The method of claim 13 wherein the method determines a parameter selected from: (i) the copy number of the EGFR gene and (ii) the methylation status of the promoter of the MGMT gene.

15. The method of claim 3 wherein the improvement is made by pre/post treatment preparation and the pre/post-treatment preparation is a method of pre/post treatment preparation selected from the group consisting of:
(i) the use of colchicine or an analog thereof;
(ii) the use of a diuretic;
(iii) the use of a uricosuric;
(iv) the use of uricase;
(v) the non-oral use of nicotinamide;
(vi) the use of a sustained-release form of nicotinamide;
(vii) the use of an inhibitor of poly-ADP ribose polymerase;
(viii) the use of caffeine;
(ix) the use of leucovorin rescue;
(x) infection control; and
(xi) the use of an anti-hypertensive agent.

16. The method of claim 3 wherein the improvement is made by toxicity management and the toxicity management is a method of toxicity management selected from the group consisting of:
(i) the use of colchicine or an analog thereof;
(ii) the use of a diuretic;
(iii) the use of a uricosuric;
(iv) the use of uricase;
(v) the non-oral use of nicotinamide;
(vi) the use of a sustained-release form of nicotinamide;
(vii) the use of an inhibitor of poly-ADP ribose polymerase;
(viii) the use of caffeine;
(ix) the use of leucovorin rescue;
(x) the use of sustained-release allopurinol;
(xi) the non-oral use of allopurinol;
(xii) the use of bone marrow transplants;
(xiii) the use of a blood cell stimulant;
(xiv) the use of blood or platelet infusions;
(xv) the administration of an agent selected from the group consisting of filgrastim, G-CSF, and GM-CSF;
(xvi) the application of a pain management technique;
(xvii) the administration of an anti-inflammatory agent;
(xviii) the administration of fluids;
(xix) the administration of a corticosteroid;
(xx) the administration of an insulin control medication;
(xxi) the administration of an antipyretic;
(xxii) the administration of an anti-nausea treatment;
(xxiii) the administration of an anti-diarrheal treatment;
(xxiv) the administration of N-acetylcysteine; and
(xxv) the administration of an antihistamine.

17. The method of claim 3 wherein the improvement is made by pharmacokinetic/pharmacodynamic monitoring and the pharmacokinetic/pharmacodynamic monitoring is a method selected from the group consisting of:
(i) multiple determinations of blood plasma levels; and
(ii) multiple determinations of at least one metabolite in blood or urine.

18. The method of claim 3 wherein the improvement is made by drug combination and the drug combination is a drug combination selected from the group consisting of:
(i) use with topoisomerase inhibitors;
(ii) use with fraudulent nucleosides;
(iii) use with fraudulent nucleotides;
(iv) use with thymidylate synthetase inhibitors;
(v) use with signal transduction inhibitors;
(vi) use with cisplatin or platinum analogs;
(vii) use with monofunctional alkylating agents;
(viii) use with bifunctional alkylating agents;
(ix) use with alkylating agents that damage DNA at a different place than does dianhydrogalactitol;
(x) use with anti-tubulin agents;
(xi) use with antimetabolites;
(xii) use with berberine;
(xiii) use with apigenin;
(xiv) use with amonafide;
(xv) use with colchicine or analogs;
(xvi) use with genistein;
(xvii) use with etoposide;
(xviii) use with cytarabine;
(xix) use with camptothecins;
(xx) use with vinca alkaloids;
(xxi) use with 5-fluorouracil;
(xxii) use with curcumin;
(xxiii) use with NF-κB inhibitors;
(xxiv) use with rosmarinic acid;
(xxv) use with mitoguazone;
(xxvi) use with tetrandrine;
(xxvii) use with temozolomide;
(xxviii) use with VEGF inhibitors;
(xxix) use with cancer vaccines;
(xxx) use with EGFR inhibitors;
(xxxi) use with tyrosine kinase inhibitors; and
(xxxii) use with poly (ADP-ribose) polymerase (PARP) inhibitors.

19. The method of claim 18 wherein the drug combination is use with a class of agent selected from the group consisting of: (i) EGFR inhibitors; (ii) tyrosine kinase inhibitors; (iii) PARP inhibitors; and (iv) an alkylating agent, wherein the alkylating agent is an alkylating agent selected from the group consisting of BCNU, BCNU wafers (Gliadel), ACNU, CCNU, bendamustine (Treanda), lomustine, and temozolomide (Temodar).

20. The method of claim 18 wherein the drug combination is use with an alkylating agent selected from the group consisting of:
(a) a monofunctional alkylating agent;
(b) a bifunctional alkylating agent; and
(c) an alkylating agent that damages DNA at a different place than dianhydrogalactitol.

21. The method of claim 3 wherein the improvement is made by chemosensitization and the chemosensitization comprises the use of a substituted hexitol derivative as a chemosensitizer in combination with an agent selected from the group consisting of:
(i) topoisomerase inhibitors;
(ii) fraudulent nucleosides;
(iii) fraudulent nucleotides;
(iv) thymidylate synthetase inhibitors;
(v) signal transduction inhibitors;

(vi) cisplatin or platinum analogs;
(vii) alkylating agents;
(viii) anti-tubulin agents;
(ix) antimetabolites;
(x) berberine;
(xi) apigenin;
(xii) amonafide;
(xiii) colchicine or analogs;
(xiv) genistein;
(xv) etoposide;
(xvi) cytarabine;
(xvii) camptothecins;
(xviii) vinca alkaloids;
(xix) topoisomerase inhibitors;
(xx) 5-fluorouracil;
(xxi) curcumin;
(xxii) NF-κB inhibitors;
(xxiii) rosmarinic acid;
(xxiv) mitoguazone;
(xxv) tetrandrine;
(xxvi) a tyrosine kinase inhibitor;
(xxvii) an inhibitor of EGFR; and
(xxviii) an inhibitor of PARP.

22. The method of claim 3 wherein the improvement is made by chemopotentiation and the chemopotentiation comprises the use of a substituted hexitol derivative as a chemopotentiator in combination with an agent selected from the group consisting of:
(i) topoisomerase inhibitors;
(ii) fraudulent nucleosides;
(iii) fraudulent nucleotides;
(iv) thymidylate synthetase inhibitors;
(v) signal transduction inhibitors;
(vi) cisplatin or platinum analogs;
(vii) alkylating agents;
(viii) anti-tubulin agents;
(ix) antimetabolites;
(x) berberine;
(xi) apigenin;
(xii) amonafide;
(xiii) colchicine or analogs;
(xiv) genistein;
(xv) etoposide;
(xvi) cytarabine;
(xvii) camptothecins;
(xviii) vinca alkaloids;
(xix) 5-fluorouracil;
(xx) curcumin;
(xxi) NF-κB inhibitors;
(xxii) rosmarinic acid;
(xxiii) mitoguazone;
(xxiv) tetrandrine;
(xxv) a tyrosine kinase inhibitor;
(xxvi) an inhibitor of EGFR; and
(xxvii) an inhibitor of PARP.

23. The method of claim 3 wherein the improvement is made by post-treatment management and the post-treatment management is a method selected from the group consisting of:
(i) a therapy associated with pain management;
(ii) administration of an anti-emetic;
(iii) an anti-nausea therapy;
(iv) administration of an anti-inflammatory agent;
(v) administration of an anti-pyretic agent; and
(vi) administration of an immune stimulant.

24. The method of claim 3 wherein the improvement is made by a bulk drug product improvement and the bulk drug product improvement is a bulk drug product improvement selected from the group consisting of:
(i) salt formation;
(ii) preparation as a homogeneous crystal structure;
(iii) preparation as a pure isomer;
(iv) increased purity;
(v) preparation with lower residual solvent content; and
(vi) preparation with lower residual heavy metal content.

25. The method of claim 3 wherein the improvement is made by use of a diluent and the diluent is selected from the group consisting of:
(i) an emulsion;
(ii) dimethyl sulfoxide (DMSO);
(iii) N-methylformamide (NMF)
(iv) DMF;
(v) ethanol;
(vi) benzyl alcohol;
(vii) dextrose-containing water for injection;
(viii) Cremophor;
(ix) cyclodextrin; and
(x) PEG.

26. The method of claim 3 wherein the improvement is made by use of a solvent system and the solvent system is selected from the group consisting of:
(i) an emulsion;
(ii) dimethylsulfoxide (DMSO);
(iii) N-methylformamide (NMF)
(iv) DMF;
(v) ethanol;
(vi) benzyl alcohol;
(vii) dextrose-containing water for injection;
(viii) Cremophor;
(ix) cyclodextrin; and
(x) PEG.

27. The method of claim 3 wherein the improvement is made by use of an excipient and the excipient is an excipient selected from the group consisting of:
(i) mannitol;
(ii) albumin;
(iii) EDTA;
(iv) sodium bisulfate;
(v) benzyl alcohol;
(vi) a carbonate buffer; and
(g) a phosphate buffer.

28. The method of claim 3 wherein the improvement is made by a dosage form and the dosage form is a dosage form selected from the group consisting of:
(i) tablets;
(ii) capsules;
(iii) topical gels;
(iv) topical creams;
(v) patches;
(vi) suppositories; and
(vii) lyophilized dosage fills.

29. The method of claim 3 wherein the improvement is made by use of a drug delivery system and the drug delivery system is a drug delivery system selected from the group consisting of:
(i) nanocrystals;
(ii) bioerodible polymers;
(iii) liposomes;
(iv) slow release injectable gels; and
(v) microspheres.

30. The method of claim 3 wherein the improvement is made by use of a drug conjugate form and the drug conjugate form is a drug conjugate form selected from the group consisting of:

(i) a polymer system;
(ii) polylactides;
(iii) polyglycolides;
(iv) amino acids;
(v) peptides; and
(vi) multivalent linkers.

31. The method of claim 3 wherein the improvement is made by use of a prodrug system and the prodrug system is selected from the group consisting of:
(i) the use of enzyme sensitive esters;
(ii) the use of dimers;
(iii) the use of Schiff bases;
(iv) the use of pyridoxal complexes; and
(v) the use of caffeine complexes.

32. The method of claim 3 wherein the improvement is made by use of a multiple drug system and the multiple drug system is selected from the group consisting of:
(i) use of multi-drug resistance inhibitors;
(ii) use of specific drug resistance inhibitors;
(iii) use of specific inhibitors of selective enzymes;
(iv) use of signal transduction inhibitors;
(v) use of repair inhibition; and
(vi) use of topoisomerase inhibitors with non-overlapping side effects.

33. The method of claim 3 wherein the improvement is made by biotherapeutic enhancement and the biotherapeutic enhancement is performed by use in combination as sensitizers/potentiators with a therapeutic agent or technique that is selected from the group consisting of:
(i) cytokines;
(ii) lymphokines;
(iii) therapeutic antibodies;
(iv) antisense therapies;
(v) gene therapies;
(vi) ribozymes;
(vii) RNA interference; and
(viii) vaccines.

34. The method of claim 3 wherein the improvement is made by use of biotherapeutic resistance modulation and the biotherapeutic resistance modulation is use against glioblastoma multiforme tumors resistant to a therapeutic agent or technique selected from the group consisting of:
(i) biological response modifiers;
(ii) cytokines;
(iii) lymphokines;
(iv) therapeutic antibodies;
(v) antisense therapies;
(vi) gene therapies;
(vii) ribozymes;
(viii) RNA interference; and
(ix) vaccines.

35. The method of claim 3 wherein the improvement is made by radiation therapy enhancement and the radiation therapy enhancement is a radiation therapy enhancement agent or technique selected from the group consisting of:
(i) hypoxic cell sensitizers;
(ii) radiation sensitizers/protectors;
(iii) photosensitizers;
(iv) radiation repair inhibitors;
(v) thiol depleters;
(vi) vaso-targeted agents;
(vii) DNA repair inhibitors;
(viii) radioactive seeds;
(ix) radionuclides;
(x) radiolabeled antibodies; and
(xi) brachytherapy.

36. The method of claim 3 wherein the improvement is by use of a novel mechanism of action and the novel mechanism of action is a therapeutic interaction with a target or mechanism selected from the group consisting of:
(i) inhibitors of poly-ADP ribose polymerase;
(ii) agents that affect vasculature or vasodilation;
(iii) oncogenic targeted agents;
(iv) signal transduction inhibitors;
(v) EGFR inhibition;
(vi) protein kinase C inhibition;
(vii) phospholipase C downregulation;
(viii) Jun downregulation;
(ix) histone genes;
(x) VEGF;
(xi) ornithine decarboxylase;
(xii) ubiquitin C;
(xiii) Jun D;
(xiv) v-Jun;
(xv) GPCRs;
(xvi) protein kinase A;
(xvii) protein kinases other than protein kinase A;
(xviii) prostate specific genes;
(xix) telomerase;
(xx) histone deacetylase; and
(xxi) tyrosine kinase inhibitors.

37. The method of claim 3 wherein the improvement is made by use of selective target cell population therapeutics and the use of selective target cell population therapeutics is a use selected from the group consisting of:
(i) use against radiation sensitive cells;
(ii) use against radiation resistant cells; and
(iii) use against energy depleted cells.

38. The method of claim 3 wherein the improvement is made by use of a substituted hexitol derivative together with ionizing radiation.

39. The method of claim 3 wherein the improvement is made by use of an agent that counteracts myelosuppression.

40. The method of claim 39 wherein the agent that counteracts myelosuppression is a dithiocarbamate.

41. The method of claim 3 wherein the improvement is made by use with an agent that increases the ability of the substituted hexitol to pass through the blood-brain barrier.

42. The method of claim 41 wherein the agent that increases the ability of the substituted hexitol to pass through the blood-brain barrier is selected from the group consisting of:
(i) a chimeric peptide of the structure of Formula (D-III):

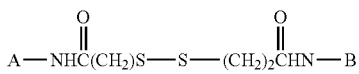

(D-III)

wherein: (A) A is somatostatin, thyrotropin releasing hormone (TRH), vasopressin, alpha interferon, endorphin, muramyl dipeptide or ACTH 4-9 analogue; and (B) B is insulin, IGF-I, IGF-II, transferrin, cationized (basic) albumin or prolactin; or a chimeric peptide of the structure of Formula (D-III) wherein the disulfide conjugating bridge between A and B is replaced with a bridge of Subformula (D-III(a)):

A-NH(CH$_2$)$_2$S—S—B (cleavable linkage)   (D-III(a)), wherein the bridge is formed using cysteamine and EDAC as the bridge reagents; or a chimeric peptide of the structure of Formula (D-III) wherein the disulfide conjugating bridge between A and B is replaced with a bridge of Subformula (D-III(b)):
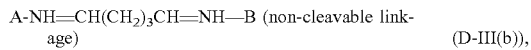
A-NH=